(12) United States Patent
Leong et al.

(10) Patent No.: US 7,732,409 B2
(45) Date of Patent: Jun. 8, 2010

(54) ESPF$_U$ NUCLEIC ACIDS AND PROTEINS AND USES THEREOF

(75) Inventors: John M. Leong, Newton, MA (US); Kenneth G. Campellone, Worcester, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 11/782,479

(22) Filed: Jul. 24, 2007

(65) Prior Publication Data

US 2008/0241104 A1 Oct. 2, 2008

Related U.S. Application Data

(62) Division of application No. 11/134,563, filed on May 20, 2005, now Pat. No. 7,250,261.

(60) Provisional application No. 60/573,600, filed on May 20, 2004.

(51) Int. Cl.
*A61K 38/00* (2006.01)
*C07K 1/00* (2006.01)
(52) U.S. Cl. .......................... 514/12; 530/350
(58) Field of Classification Search ................. 530/350; 514/12
See application file for complete search history.

(56) References Cited

U.S. PATENT DOCUMENTS 6,365,723 B1 * 4/2002 Blattner et al. ............. 536/23.1
2003/0023075 A1 1/2003 Blattner et al.

FOREIGN PATENT DOCUMENTS

JP 355074 * 12/2002

OTHER PUBLICATIONS

Perna et al., UniProt Database, accession No. Q8X482, Mar. 2002.*
Bladt et al., "The murine Nck SH2/SH3 adaptors are important for the development of mesoderm-derived embryonic structures and for regulating the cellular actin network," Mol. Cell Biol. 23:4586-97 (2003).
Campellone and Leong, "Tails of two Tirs: actin pedestal formation by enteropathogenic *E. coli* and enterohemorrhagic *E. coli* O157:H7," Curr. Opin. Microbiol. 6:82-90 (2003).
Campellone et al., "A tyrosine-phosphorylated 12-amino-acid sequence of enteropathogenic *Escherichia coli* Tir binds the host adaptor protein Nck and is required for Nck localization to actin pedestals," Mol. Microbiol. 43:1227-41 (2002).
Campellone et al., "Clustering of Nck by a 12-residue Tir phosphopeptide is sufficient to trigger localized actin assembly," J. Cell Biol. 164:407-16 (2004).
Campellone et al., "EspF$_U$ is a translocated EHEC effector that interacts with Tir and N-WASP and promotes Nck-independent actin assembly," Dev. Cell 7:217-28 (2004).
Celli et al., "Enteropathogenic *Escherichia coli* (EPEC) attachment to epithelial cells: exploiting the host cell cytoskeleton from the outside," Cell Microbiol. 2:1-9 (2000).
Court et al., "Genetic engineering using homologous recombination," Annu. Rev. Genet. 36:361-88 (2002).
Crane et al., "Role of EspF in host cell death induced by enteropathogenic *Escherichia coli*," Cell. Microbiol. 3:197-211 (2001).
de Grado et al., "Identification of the intimin-binding domain of Tir of enteropathogenic *Escherichia coli*," Cell. Microbiol. 1:7-17 (1999).
Deibel et al., "EspE, a novel secreted protein of attaching and effacing bacteria, is directly translocated into infected host cells, where it appears as a tyrosine-phosphorylated 90 kDa protein," Mol. Microbiol. 28:463-74 (1998).
Desai et al., "The use of *Xenopus* egg extracts to study mitotic spindle assembly and function in vitro," Methods Cell. Biol. 61:385-412 (1999).
DeVinney et al., "Enterohaemorrhagic and enteropathogenic *Escherichia coli* use a different Tir-based mechanism for pedestal formation," Mol. Microbiol. 41:1445-58 (2001).
DeVinney et al., "Enterohemorrhagic *Escherichia coli* O157:H7 produces Tir, which is translocated to the host cell membrane but is not tyrosine phosphorylated," Infect. Immun. 67:2389-98 (1999).
Donnenberg and Whittam, "Pathogenesis and evolution of virulence in enteropathogenic and enterohemorrhagic *Escherichia coli*," J. Clin. Invest. 107:539-48 (2001).
Frankel et al., "Enteropathogenic and enterohaemorrhagic *Escherichia coli*: more subversive elements," Mol. Microbiol. 30:911-21(1998).
Goosney et al., "Recruitment of cytoskeletal and signaling proteins to enteropathogenic and enterohemorrhagic *Escherichia coli* pedestals," Infect. Immun. 69:3315-22 (2001).
Gruenheid et al., "Enteropathogenic *E. coli* Tir binds Nck to initiate actin pedestal formation in host cells," Nat. Cell. Biol. 3:856-9 (2001).
Hartland et al., "Binding of intimin from enteropathogenic *Escherichia coli* to Tir and to host cells," Mol. Microbiol. 32:151-8 (1999).
Heng and Cao, "Making cell-permeable antibodies (Transbody) through fusion of protein transduction domains (PTD) with single chain variable fragment (scFv) antibodies: potential advantages over antibodies expressed within the intracellular environment (Intrabody)," Med. Hypotheses 64:1105-8 (2005).
Ho et al., "Toca-1 mediates Cdc42-dependent actin nucleation by activating the N-WASP-WIP complex," Cell 118:203-16 (2004).
Hudson and Souriau, "Engineered antibodies," Nat. Med. 9:129-34 (2003).

(Continued)

*Primary Examiner*—Maryam Monshipouri
(74) *Attorney, Agent, or Firm*—Fish & Richardson P.C.

(57) ABSTRACT

Disclosed are EspF$_U$ (EspF-like polypeptide encoded by a gene of the cryptic prophage CP-933U of enterohemorrhagic *E. coli*) polypeptides, fragments thereof, nucleic acids that encode EspF$_U$ polypeptides, or fragments thereof, and cells including the polypeptides, fragments, and/or nucleic acids. Also disclosed are model systems, kits, and methods for screening that use, for example, EspF$_U$ polypeptides and nucleic acids. Also included are pharmaceutical and diagnostic compositions and methods of diagnosis and treatment of EHEC infections.

15 Claims, 21 Drawing Sheets

OTHER PUBLICATIONS

Kenny et al., "Enteropathogenic *E. coli* (EPEC) transfers its receptor for intimate adherence into mammalian cells," Cell 91:511-20 (1997).

Kenny, "Phosphorylation of tyrosine 474 of the enteropathogenic *Escherichia coli* (EPEC) Tir receptor molecule is essential for actin nucleating activity and is preceded by additional host modifications," Mol. Microbiol. 31:1229-41 (1999).

Kenny, "The enterohaemorrhagic *Escherichia coli* (serotype O157:H7) Tir molecule is not functionally interchangeable for its enteropathogenic *E. coli* (serotype O127:H6) homologue," Cell. Microbiol. 3:499-510 (2001).

Liu et al., "Point mutants of EHEC intimin that diminish Tir recognition and actin pedestal formation highlight a putative Tir binding pocket," Mol. Microbiol. 45:1557-73 (2002).

Lommel et al., "Actin pedestal formation by enteropathogenic *Escherichia coli* and intracellular motility of *Shigella flexneri* are abolished in N-WASP-defective cells," EMBO Rep. 2:850-7 (2001).

Lommel et al., "Enterohaemorrhagic and enteropathogenic *Escherichia coli* use different mechanisms for actin pedestal formation that converge on N-WASP," Cell. Microbiol. 6:243-54 (2004).

McNamara et al., "Translocated EspF protein from enteropathogenic *Escherichia coli* disrupts host intestinal barrier function," J. Clin. Invest. 107:621-9 (2001).

Mundt et al., "Intrabodies—Valuable tools for target validation," EBR Winter 2001, ESBA Tech Ed. Jan. 10, 2002.

Murphy and Campellone, "Lambda Red-mediated recombinogenic engineering of enterohemorrhagic and enteropathogenic *E. coli*," BMC Mol. Biol. 4:11(2003).

Murphy et al., "PCR-mediated gene replacement in *Escherichia coli*," Gene 246:321-30 (2000).

Nataro and Kaper, "Diarrheagenic *Escherichia coli*," Clin. Microbiol. Rev. 11:142-201(1998).

Perna et al., "Molecular evolution of a pathogenicity island from enterohemorrhagic *Escherichia coli* O157:H7," Infect. Immun. 66:3810-7 (1998).

Peterson et al., "A chemical inhibitor of N-WASP reveals a new mechanism for targeting protein interactions," Proc. Natl. Acad. Sci. USA 98:10624-9 (2001).

Ritchie et al., "Critical roles for $stx_2$, *eae*, and *tir* in enterohemorrhagic *Escherichia coli*-induced diarrhea and intestinal inflammation in infant rabbits," Infect. Immun. 71:7129-39 (2003).

Rohatgi et al., "Nck and phosphatidylinositol 4,5-bisphosphate synergistically activate actin polymerization through the N-WASP-Arp2/3 pathway," J. Biol. Chem. 276:26448-52 (2001).

Tzipori et al., "The role of the *eaeA* gene in diarrhea and neurological complications in a gnotobiotic piglet model of enterohemorrhagic *Escherichia coli* infection," Infect. Immun. 63:3621-7 (1995).

Viswanathan et al., "Comparative analysis of EspF from enteropathogenic and enterohemorrhagic *Escherichia coli* in alteration of epithelial barrier function," Infect. Immun. 72:3218-27 (2004).

Viswanathan et al., "Microbes and their products—physiological effects upon mammalian mucosa," Adv. Drug Deliv. Rev. 56:727-62 (2004).

Wagner and Waldor, "Bacteriophage control of bacterial virulence," Infect. Immun. 70:3985-93 (2002).

Restriction Requirement, in U.S. Appl. No. 11/134,563, mailed Nov. 24, 2006 (10 pages).

Fish & Richardson P.C., Response to Restriction Requirement, in U.S. Appl. No. 11/134,563, filed Dec. 22, 2006 (1 page).

Notice of Allowance, in U.S. Appl. No. 11/134,563, mailed Apr. 4, 2007 (14 pages).

Fish & Richardson P.C., Response to Notice of Allowance, in U.S. Appl. No. 11/134,563, filed Jun. 25, 2007 (2 pages).

\* cited by examiner

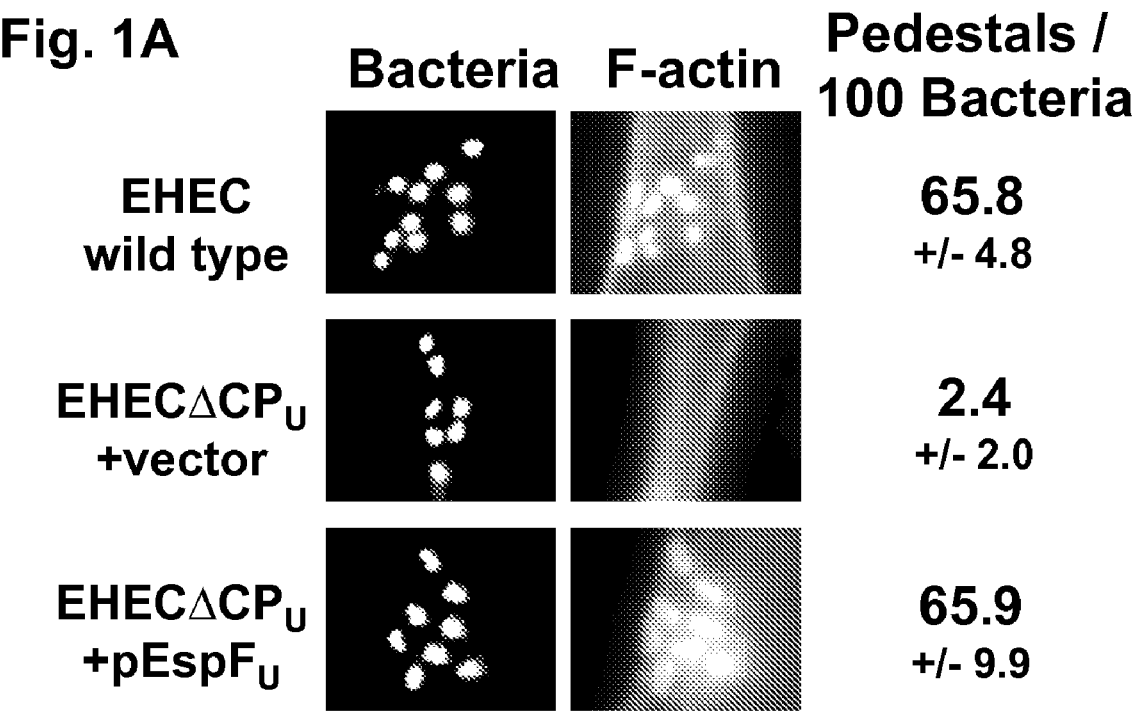
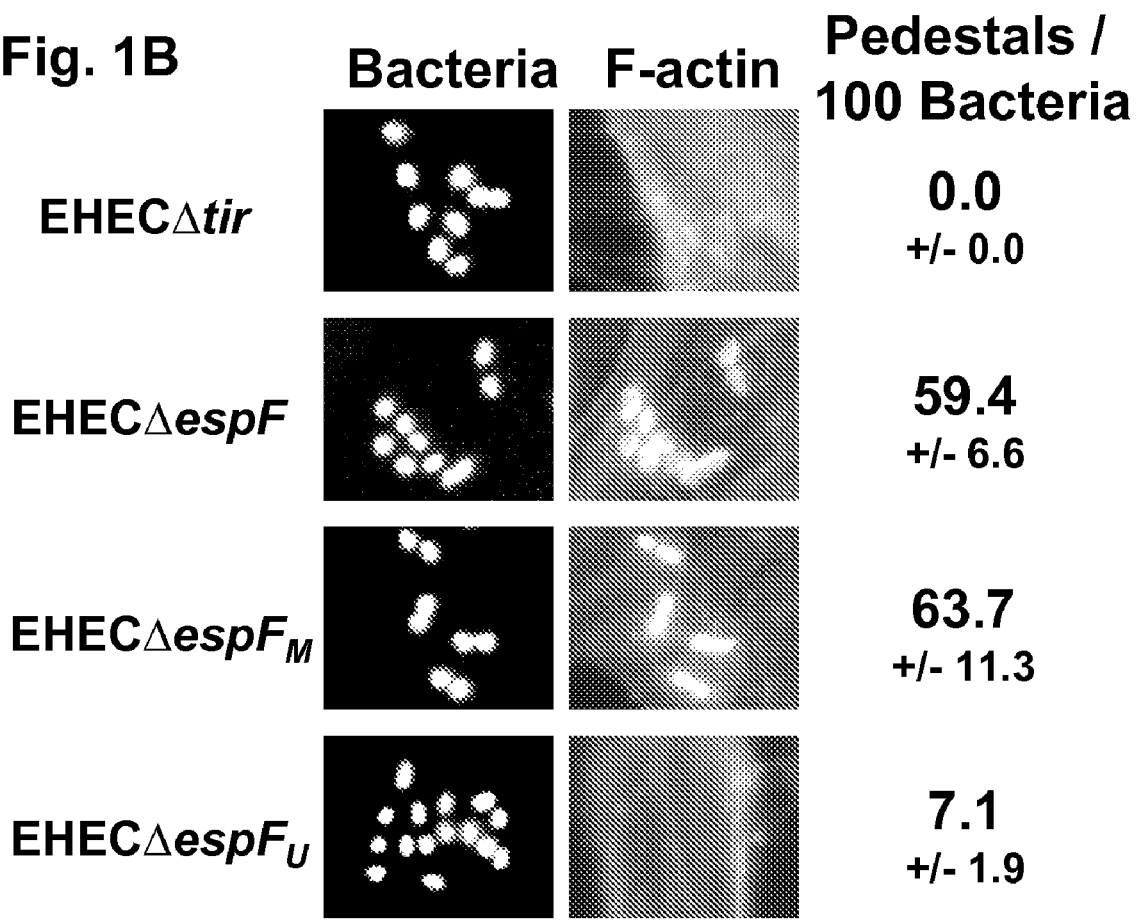

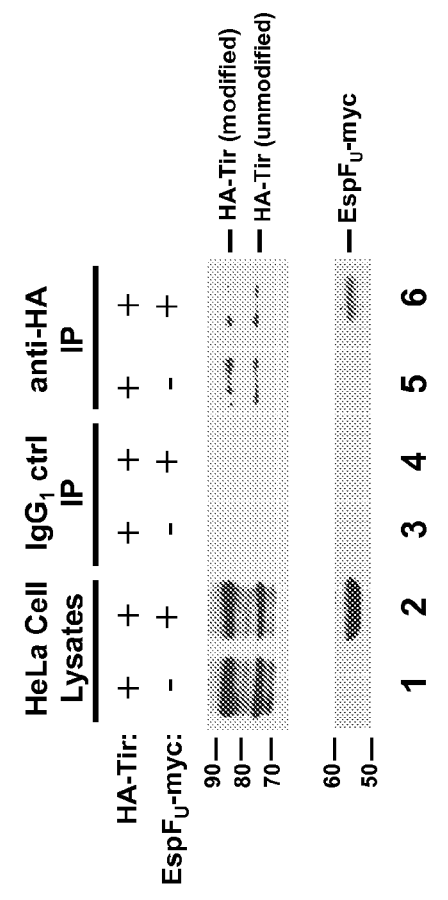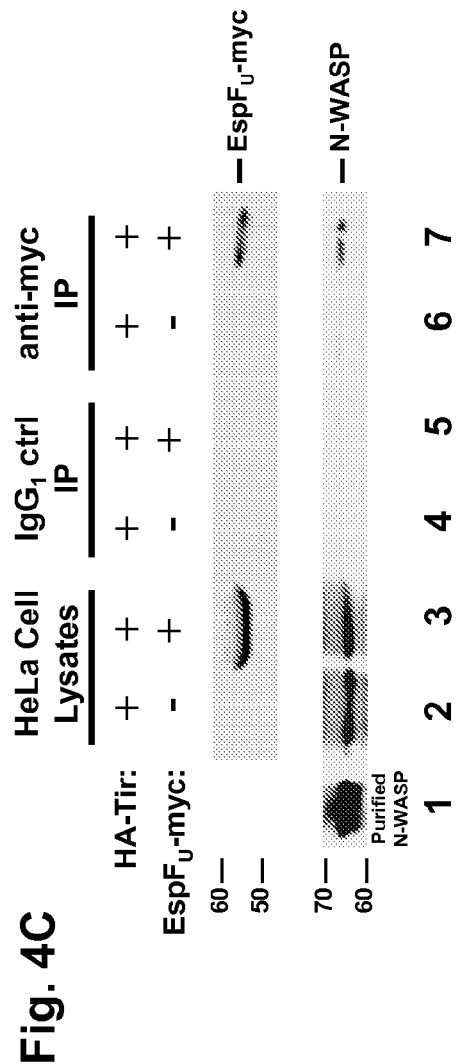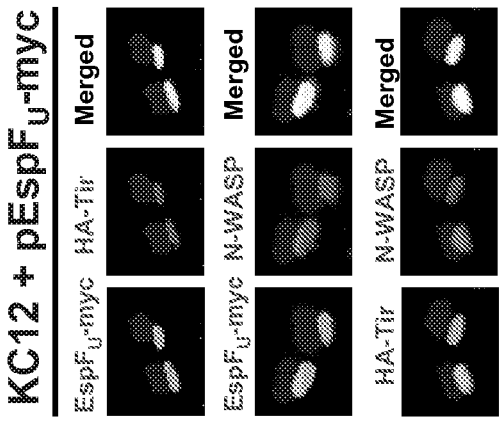
Fig. 4A
Fig. 4B
Fig. 4C

Fig. 5A

ATGATTAACAATGTTTCTTCACTTTTTCCAACCGTCAACCGCAATATTACAGCTGTATAT
AAAAAAGCAGCTTCTCTGTATCACCACAGAGAAAATCACATTAAATCCTGTAAAAATCAGC
TCACCTTTTCACCAAGCAGTAGCTCCATCGACAACTCTCTTTCGAGCCCCAAAC
GCCCATTCGGCATCATTTCATCGACAGTCTACTGCTGAAAGTTCGTTACATCAACAACTT
CCTAATGTGAGGCAGCCCTGATACAACATCTTGCAGAGCATGGCATTAAACCTGCCCGG
AGTATGGCTGAACATCAAGACCCTGAACCAGCCCAGTACAAACCGCCAGTACAA
AATGAACAATCAGCCATTCAACCGCCACCTGCGCCCCGGAATATGGCTGCAGAG
CATGGCATTCAACCACTGCCAGCATCTTCAACCGCCACCTGCGCCCCGGAATATGGCTGCA
GCGCCACCACTGCCAGCATCTTGCAGAGCATGGCATTCAACCGCCACCTGCGCCCCAGTA
CTGGTGCAGCATCTTGCAGAGCATGGCATTCAACCGCCACCTGCGCCCCAGTACAAAATGAA
CCTCCGGCACCTGCGCCCCAGTACAAAATGAACAATCAAGACCCTGAACATATGGCTGCA
CTGCCTGATGTGGCTCAGCGTCTGATGTGGCTCAGCGTCTGATGTGGCTCAGCGTCTGATGTGGCTCAGCGTCTGATGTGGCTCAGCGT
CGGAGTATGAACAATCAAGACCCTGAACATATGGCTGCAGCGTCTGATGTGGCTCAGCGT
CAAAATGAACAATCAAGACCCTGAACATATGGCTGCAGCGTCTGATGTGGCTCAGCATCTTGCA
GAGCATGGCATTCAACCGCCACCTGCGCCCCAGTACAAAATGAACAATCAAGA
CCTGCGCCAACGCGCCAGTACAAAATGAACAATCAAGACCCTGAACATATGGCTCAG
CGTCTGATGCAGCCCGGAATATGAACAATCAAGACCCTGAACATATGGCTGAACAT
ATTCCTCCGGCACCTGCGCCCCAGTACAAAATGAACAATCAAGAAGA
CCTTTGCCTGATGTGGCTCAGCGTCTGATGCAGCCATCTTGCAGAGCATGGCATTAATACA
TCTAAGCGCTCGTGA (SEQ ID NO:1)

Fig. 5B

MINNVSSLEPTVNRNITAVYKKSSFSVSPQKITLNPVKISSPFSPSSSISATTL
FRAPNAHSASFHRQSTAESSLHQQLPNVRQRLIQHLAEHGIKPARSMAEHIPPAP
NWPAPPPVQNEQSRPLPDVAQRLVQHLAEHGIQPARNMAEHIPPAPNWPAPPLP
VQNEQSRPLPDVAQRLVQHLAEHGIQPARSMAEHIPPAPNWPAPPPVQNEQSRP
LPDVAQRLVQHLAEHGIQPARNMAEHIPPAPNWPAPPPVQNEQSRPLPDVAQRL
MQHLAEHGIQPARSMAEHIPPAPNWPAPTPPVQNEQSRPLPDVAQRLMQHLAEHG
IQPARNMAEHIPPAPNWPAPTPPVQNEQSRPLPDVAQRLMQHLAEHGINTSKRS
(SEQ ID NO:2)

Fig. 6A

CTTCCTAATGTGAGGCAGGCCCTGATACAACATCTTGCAGAGACATGGCATTAAACCTGCCCGGAGTAT
GGCTGAACATATTCCTCCGGCACCTAACTGGCCTGCGCCACCACCGCCAGTACAAAATGAACAATCAA
GACCTCTGCCTGATGTGGCTCAGCGTCTGGTGCAGCATCTTGCAGAGCATGGCATTCAACCAGCCCGG
AATATGGCTGAACATATTCCTGCCGCACCTAACTGGCCTGCGCCACTGCCAGTACAAAATGAACA
ATCAAGACCTCTGCCTGATGTGGCTGAACATATTCCTGCCTGAACTGGCTGTGCAGCATCTTGCAACCAG
CCCGGAGTATGGCTGAACATATTCCTCCGGCACCTAACTGGCCTGTGCAGCGTCTGGTGCAGCATTCA
GAACAATCAAGACCCCGGAGTATGGCTGAACATATTCCTGCCTGAACTGGCTGCACCTAACTGGCCTGCACCACCGCCAGTAC
AAAATGAACAATCAAGACCTCTGCCTGATGTGGCTCAGCGTCTGATGCAGCATCTTGCCGCCAGCATGGC
ATTCAACCAGCCCGGAATATGGCTGAACATCAAGACCTTTGCCTGAACTGGCTCTGATGCAGCATCTTGC
AGTACAAAATGAACAATCCGGAATAATCAAGACCCCGGAATACAATCAAGACCCCAACG
ATGGCATTCAACCAGCCCGGAATACAATCTAAGCGCTCGTGA (SEQ ID NO:3)

Fig. 6B

LPNVRQRLIQHLAEHGIKPARSMAEHIPPAPNWPAPPPVQNEQSRPLPDVAQR
LVQHLAEHGIQPARNMAEHIPPAPNWPAPPLPVQNEQSRPLPDVAQRLVQHLAE
HGIQPARSMAEHIPPAPNWPAPPPVQNEQSRPLPDVAQRLVQHLAEHGIQPAR
SMAEHIPPAPNWPAPPPVQNEQSRPLPDVAQRLMQHLAEHGIQPARNMAEHIP
PAPNWPAPTPPVQNEQSRPLPDVAQRLMQHLAEHGINTSKR (SEQ ID NO:4)

Fig. 7A

ATGAGCTCCGTCCAGCAGCAGCCGCCGCGGGAGGGTCACCAACGTGGGTCCCTGTTGCTCACC
CCGCAGGAGAACGAGTCCCTCTTCACTTTCCTCCGGCAAGAAATGTGTGACTATGTCTTCAGCAGTGGTG
CAGTTATATGCAGCAGATCTTATTTTTAAGAATATTTGACATTAAGGATGGAAACTATTGTGGGAACAA
GACAATCCACAGAGATCTTATTTTTAAGAATATTTGACATTAAGGATGGAAACTATTGTGGGAACAA
GAGCTATACAATAACTTTGTATATAATAGTCCTAGAGGATATTTCATACCTTTGCTGAGATACTTGT
CAAGTTGCTCTTAATTTTGCCAATGAAGAAGCAAAAAAATTCGAAAAGCAGTTACAGACCTTTG
GGCCGTCGACAAAGGAAATCTGAGAAAAGACGAGATCCCCAAATGGTCCTAATCTACCATGGCTACA
GTTGATATAAAAATCACAACAGAGAAATCACAACAGATTTTATGGTCAAGTCAGATATAGGAACACTCCCAT
ACCAAAGAAAAGAAGGGAAAAGCTAAAAAGAGATTAACCACAGGCTTTGATCTGAATAATTTGGATCCA
AATTTCCAGCACATTGGACATGTTGGTTGGGATCCAAATACACAGGCTTTGATCTGAATAATTTGGATCCA
GAATTGAAGAATCTTTCGATATGTGTGAATACAGAGGTGTTGAAGCTGTTAAAAATGAACTTAAAGACAGAGAAACATCAAAA
GTTATATATGACTTTTATTGAAAAAAACAGGGGAGGGCCACCTCCTCCCCCCACACAACTCAGGTCCT
CCACCACCTCCACCACCATCAAGGGAGGGCCACCTCCTCCCCCCACACAACTCAGGTCCT
CCTCCTCCTCCTGCTAGGGACCTCCCAAGTGTAGCACCTTCCACCACCGCCAAATAGGATGTACCCTCCT
CCACCACCGCCAGCCCTTCCCTCCCCAGCACCTTCAGGCTCCCATCTGTGTTGGGGTA
CCACCTCCAGCCCTTCCCTCCCCAGCACCTTCAGGCTCCCATCTGTGTTGGGGTA
GGGCCAGTGGGACCATCCAGGTTCCAACTACTGCAGGAGCAGAACAGTCTCTTTAGATCAAATTAGA
CCTTCTGATGGGACCATCCAGGTTCCAACTACTGCAGGAGCAGAACAGTCTCTTTAGATCAAATTAGA
GAGGGTGCTCAGTCAGAGGGTATCCAACTAAAATCGACAGGGTCTCCTGATGGCCAAGAGTCTACACCAACA
TTAGACCAGATACGACAGGGTATCCAACTAAAATCGACAGGGTCTCCTGATGGCCAAGAGTCTACACCAACA
CCTGCACCCACTTCAGGGAATTGTGGGTGCATTAATGAAGTGATGCAGAAAAGGAGCAAAGCCATTCAT
TCTTCAGATGAAGATGAAGATGAAGAAGATTTGAGGATGATGAGTGAGTGGGAAGACTGA
(SEQ ID NO:5)

Fig. 7B

MSSVQQQPPPPRRVTNVGSLLLTPQENESLFTFLGKKCVTMSSAVVQLYAADRNCMWSK
KCSGVACLVKDNPQRSYFLRIFDIKDGKLLWEQELYNNFVYNSPRGYFHTFAGDTCQVA
LNFANEEEAKKFRKAVTDLLGRRQRKSEKRRDPPNGPNLPMATVDIKNPEITTNRFYGP
QVNNISHTKEKKKGKAKKKRLTKADIGTPSNFQHIGHVGWDPNTGFDLNNLDPELKNLF
DMCGISEAQLKDRETSKVIYDFIEKTGGVEAVKNELRRQAPPPPPSRGGPPPPPPPH
NSGPPPPPARGRGAPPPPPSRAPTAAPPPPPPPPPPPGPPPPPGLPSDGDHQVPTTAGNKAALLDQI
PSGPPPPPSVLGVGPVAPPPPPPPPPPGLPSDGDHQVPTTAGNKAALLDQI
REGAQLKKVEQNSRPVSCSGRDALLDQIRQGIQLKSVADGQESTPPTPAPTSGIVGALM
EVMQKRSKAIHSSDEDEDEEDEEDFEDDEWED (SEQ ID NO: 6)

Fig. 8A

ATGAGCTCGGCCAGCAGCCCCCGCGGAGGGTCACCAACGTGGGCTCCCTGCTCACCCCGCAAG
AAAACGAGTCTCTTTCTCCTTCCTCGGCAAGAATGTGTGACTATGTCTTCAGCAGTGGTGCAGTT
ATATGCAGCTGATCGGAACTGTATGTGGTCAAAGAAGTGCAGTGGTGGTTGCTTGTCTTGTTAAGGAC
AATCCTCAGAGATCTTATTTTTAAGAATATTGACATTAAGGATGGGAAATTACTGTGGAACAAG
AGCTATACAATAACTTTGTATATAATAGTCCTAGAGGATATTTTCATACCTTTGCTGGAGATACTTG
TCAAGTAGCTCTTAATTTGCCAATGAAGAAGCAAAAAAGTTCCGAAAAGCAGTACAGACCTG
TTGGGTCGACACAAAGGAAATCTGAAAAAAAGACGAGATGCTCCAAATGTCTACCCATGG
CTACAGTTGACATAAAAATCCAGATAAAGAAAAGCTAAAAAGAGATTAACCAAGGCAGATATTGGA
CTCCCACCAAAGTAATTTCCAGCACATTGGACATGTTGGTTGGGATCCAAATACAGGTTTTGATCTAAATA
ACACCAAGTAATTTCCAGCACATTGGACATGTTGGTTGGGATCCAAATACAGGTTTTGATCTAAATA
ATTTGGATCCAGAATGTCTTTTGACTTTATTGAAAAAACAGGAGGTGTAGAAGCTTAAAAATGAA
AGAAACATCAAAAGTTATTTATGACTTTATTGAAAAAACAGGAGGTGTAGAAGCTTAAAAATGAA
CTCCGAAGGCAAGCACCACCCCTCCTCCACCTCCTCCCCCGTGAAGGAGGACCCCTCCCCCTC
CTCACAGCTCAGGGGCTCAGGCCCTGCCCCACCTCCTGCCCCGTGAAGGGGGCTCCTGGTGTCCTTGTTCCTCCACCTCCT
AGCTCCTACTGCTGCACCTCTGCACCTCCACCACCTCCTAGAGCCTTCCTCAGCCACCCTTCAGCCCCACCACCAC
CCAAACAGGATGTACCCCTCCACCACCACCTCCTCCTAGAGCCCTTCCTCAGCCACCCTTCAGCCCCACCACCAC
CTCCGCCTCTGTCTATGGCAGGGGTCCACCAGGTCGCCTTGACGTGACCATCAAGTTCCAGCTTCTTCAGGAAACAAA
GCCACCACCTCCCCCTGGCCTGCCTTCTGATGGTGACCAGAGGGTGCTCTAGACCAGATACGGCCAGCATTCAGTTGGGTGCGTGTC
GCAGCTCTTTTGGATCAAATTAGAGAGGGATGCACTTCTAGACCAGATACGGCCAGCATTCAGTTGGGTGCGTGTC
TGTCCTGCTCAGGAAGAGTCCACCACCAAAGGAGCAAAGCCATTCCTCAGATGAAGATGATGAAGAAG
TGATGGCCAGAGAGTCCACCACCAAAGGAGCAAAGCCATTCCTCAGATGAAGATGATGAAGAAG
GTGATGCAGAAGAAGGAGCAAAGCCATTCCTCAGATGAAGATGATGAAGAAG
ATTTGAGGATGATGATGAGTGGGAAGACTGA (SEQ ID NO:7)

Fig. 8B

MSSGQQPPRRVTNVGSLLLTPQENESLFSFLGKKCVTMSSAVVQLYA
ADRNCMWSKKCSGVACLVKDNPQRSYFLRIFDIKDGKLLWEQELYNN
FVYNSPRGYFHTFAGDTCQVALNFANEEEAKKFRKAVTDLLGRRQRK
SEKRRDAPNGPNLPMATVDIKNPEITTNRFYSSQVNNISHTKEKKKG
KAKKKRLTKADIGTPSNFQHIGHVGWDPNTGFDLNNLDPELKNLFDM
CGISEAQLKDRETSKVIYDFIEKTGGVEAVKNELRRQAPPPPPSRG
GPPPPPPHSSGPPPPARGRGAPPPPPSRAPTAAPPPPPPSRPGV
VVPPPPNRMYPPPPPALPSSAPSGPPPPPLSMAGSTAPPPPPPP
PPPGPPPPPGLPSDGDHQVPASSGNKAALLDQIREGAQLKKVEQNSR
PVSCSGRDALLDQIRQGIQLKSVSDGQESTPPTPAPTSGIVGALMEV
MQKRSKAIHSSDEDEDDDDEEDFQDDDEWED (SEQ ID NO:8)

Fig. 9A

GGTCCCAATCTACCCCATGGCTACAGTTGACATAAAAATCCAGAA
ATCACAACAAACAGGTTTATAGTTCACAAGTCAACAACATCTCC
CACACCAAAGAAAAGAAGAAAGCTAAAAGAAGAGATTA
ACCAAGGCAGATATTGGAACCACCAAGTAATTCCAGCACATTGGA
CATGTTGGTTGGGATCCAAATACAGGTTTTGATCTAAATAATTTG
GATCCAGAATTGAAGAATCTTTTGATATGTGTGGGATCTCTGAG
GCCCAGCTTAAAGACACAGAGAAACATCAAAAGTTATTTATGACTTT
ATTGAAAAAAACAGGAGGTGTAGAAGCTGTTAAAAAATGAACTCCGA
AGGCAAGCA (SEQ ID NO:9)

Fig. 9B

GPNLPMATVDIKNPEITTNRFYSSQVNNISHTKEKKKGKAKKRLTK
ADIGTPSNFQHIGHVGWDPNTGFDLNNLDPELKNLFDMCGISEAQLK
DRETSKVIYDFIEKTGGVEAVKNELRRQA (SEQ ID NO:10)

Fig. 10A

ATGCCTATTGGTAACCTTGGTCATAATCCCAATGTGAATAATTCAATTCCTCCTGCACCTCCATTACCT
TCACAAACCGACGGTGCAGGGGGCGTGGTCAGCTCATTAACTCTACGGGGCCCGTTGGGATCTCGTGCG
CTATTTACGCCTGTAAGGAATTCTATGGCGGCGTCTGATTCTGATCGTGCCAGTGATGATGTTCCTGACTT
CCTGTAAATCCGATGCGCCTGGCGGCGTCTGAGATAACACTGAATGATGGATTTGAAGTTCTTCATGAT
CATGGTCCGCTCGATACATTGCTGTCGGTCTTAACAGGCAGAATGGCTCTCGGTATTCGAGTTGAAACTCAGGAAGAT
GGTAAACATATTGCTGTCGGTCAGAGGAATGGTGTTGAGACCCTCTGTGTTTAAGTGATCAAGAGTAC
GCTCGCTTGCAGTCATTGATCCGTTGCTTCAGATATCACGGAAGCCCGCAAAGGATACTGGAGCTGTTAGAG
GGGCATGCTATGCACCGTTGCTTCAGATATCACGGAAGCCCGCAAAGGATACTGGAGCTGTTAGAG
CCCAAAGGACCGGGAGTCCAAAAGCGTTGGGAGTCAACTTCCAGCCCTTCGTTCAGATCCTAAA
AGCGGTGCCGAAAACACCAGAGAAACTCAACTTCCAGCCCTTCGTTCAGATCCTAAA
CTTTGGTTGCCTTGGGACTCGTTGCTACAGGTTGGCGGCCGACCCTGATGCCAAGTCAACTGAA
CTTGCATTGACGCCCGGACATCAGTTAACGAAAGAAGCGTTCCAGAACCCAGATAATCAAAAAGTTAATATCGAT
ACTGCGACAAGAGATCAGTTAACGAAAGAAGCGTTCCAGAACCCAGATAATCAAAAAGTTAATATCGAT
GAGCTCGACACCTCGCTGATTCCGTCAGGGCTATTGTTGCGAATAATGCTCAGGCGCAAAAAATATGAT
AAAGCAGCAGGCGAAGAGCCAAAACAGCCATTGAAAATAATGCTCAGGCGCAAAAAATATGAT
GAACAACAAGCTAAAACGGGGGAATTGGTGTTGCCGTGCGCTTCATCGACGTAGAAATCAGCCGGTAGAA
TTGATTCTTGGTGGGAATTGGTGTTGCCGTGCGCTTCATCGACGTAGAAATCAGCCGGTAGAA
CAAACAACAACTGCACAGGCAATGTAGAATACCCCTGGTCAGAACATAGGAGACCGTAGCTCG
AATACACCTGCACAGGCAATGTAGAATACCCCTGGTCAGAACATAGGAGACCGTAGCTCG
ATGGCTAGCACCTCGCTGATTCGACTTTCTTTGACACTTGCCAGGTCCGCAGATTCGTCAGAATCCGTATGCTGAT
GTTAAAACATTCTGCTGTATATAGCCACCTTCAAACATCCCCGGATACTACTGATAACGGCGCACGG
AATACAGATTCTGTTGTATATAGCCACCTTCAAACATCCCCGGATACTACTGATAACGGCGCACGG
TTATTAGGAAATCAAGTGGGGGATTCAAGATAATAACGGGGGGGAGTAATAGCGCTGTGAATACTTCGAATAACCCCAGCGCCG
CATGACATGGGAGGATTAACGGGGGGGGAGTAATAGCGCTGTGAATACTTCGAATAACCCCAGCGCCG
GGATCCCATCGTTTCGTCTAA (SEQ ID NO:11)

Fig. 10B

MPIGNLGHNPNVNNSIPPAPPLPSQTDGAGGRGQLINSTGPLGSRALFTPVRNSMADSG
DNRASDVPGLPVNPMRLAASEITLNDGFEVLHDHGPLDTLNRQIGSSVFRVETQEDGKH
IAVGQRNGVETSVVLSDQEYARLQSIDPEGKDKFVFTGGRGGAGHAMVTVASDITEARQ
RILELLEPKGTGESKGAGESKGVGELRESNSGAENTTETQTSTSTSSLRSDPKLWLALG
TVATGLIGLAATGIVQALALTPEPDSPTTTDPDAAASATETATRDQLTKEAFQNPDNQK
VNIDELGNAIPSGVLKDDVVANIEEQAKAAGEEAKQQAIENNAQKKYDEQQAKRQEE
LKVSSGAGYGLSGALILGGGIGVAVTAALHRKNQPVEQTTTTTTTTSARTVENKPA
NNTPAQGNVDTPGSEDTMESRRSSMASTSSTFFDTSSIGTVQNPYADVKTSLHDSQVPT
SNSNTSVQNMGNTDSVVYSTIQHPPRDTTDNGARLLGNPSAGIQSTYARLALSGGLRHD
MGGLTGGSNSAVNTSNNPPAPGSHRFV    (SEQ ID NO:12)

Fig. 11A

```
ATGAGCTGGGGCACGGAGCTGTGGGATCAGTTCGACAGCTTAGACAAGCATACACAATGGGAATTGA
CTTCTTGGAAAGATATGCCAAATTTGTTAAAGAGAGGATAGAAATTGAACAGAACTATGCGAAACAT
TGAGAAATCTGGTTAAGAAGTACTGCCCCCAAACGTTCATCCAAAGATGAAGAGCCACGTTACCTCG
TGTGTAGCCTTTTTTAATATCCTTAATGAGTTAAATGACTATGCAGGACAGCGAGAAGTTGTAGCAGA
AGAAATGGCGCACAGAAGGACGAAAAGCTCAACAATATCTTGACATGTGCTGGAAACAGATGGATAATAGT
TGCATCTGCAAGAAGGACGAAAAGCTCAACAATATCTTGACATGTGCTGGAAACAGATGGATAATAGT
AAAAAGAAGTTTGAAAGAGAATGTAGAGGCAGAAATGTTGAAAAGGCCAAAACAGCAGTTATGAAAGATTGGATAA
TGATACTAATGCAACCAAGGCAGATGTTGCACAAATTTAATGGAGAACAACATAAACATTTT
CCGATGAAAATAAAAATGAATATGCTCAGATTCCTCAGAGAATTGGACGAAGGACTATTAAACTCAG
TATGTAGTGATTCCTCAGAGGATTGCTGACTCAGAACGCAAAGTTATTCCCATCATTCAAAATGTTGGAAG
GAATGATTCTTGAACCTCCAGGAGACTTTCCATTGAAGATTACAGTCAACATATATAGAACCATTTC
TCTGGTTTTTGAACCTCCAGGAGACTTTCCATTGAAGATTACAGTCAACATATATAGAACCATTTC
TGATGGACTATCAGTGCCATCCAAACAGGAGAGTGGAAGATGCCAAAGGCCACTAGAAGATTCAGTCATCTG
CCAAGGGCAAATTGTGGCTCTTTGGAAAAGAAGCCAAAAGGGCCAGCACTAGAACTTAACAGAACTACACAGAAAGA
CCACCAGAACAGACGTAAAAAAACTCAACAAAATGAAAAGATGTATATGAAGAATCCACAAATGGGGGATC
ATCAGACCAAAAAGATCCACTCAAATAGCAGAACCATGAATAACAATTGACCGCCTACGAATGGAAATCCAT
CAGGGAGTTGCAGCCTAAATTAGCAGAACCATGAATAACAATTGACCGCCTACGAATGGAAATCCAT
AAGAATGAGGCTTGGCTCTCTGAAGTCGAAGGCGAGAAGTCCTGAGGGAAGTTACACTGATGATGCAAACC
TGACATAAATCATCTTGTAACACAGGACACTGCAAAGCTATCTGCCCTTTTGATGGACATAATGAAGGTACTCT
AGGAAGTCCGTGGGCCTATTGGACACCCCCGAAGTGAAGTTCTCTACATTATAGAGGACAAAAGGTGACGAAGAGCTC
GATCCCTTGCCCTGCTATTGGACACCCCCGAAGTGAAGTTCTCTACATTATAGAGGACAAAAGGTGACGAAGAGCTC
AGCAATGAAAGAACGGTGAAGAAGGCTACGTTCCCACGTCATACATAGATGTAACTCTAGAGAAAAACAGT
GGAGACAGAACGGTGAAGAAGGCTACGTTCCCACGTCATACATAGATGTAACTCTAGAGAAAAACAGT
AAAGGTTCCTGA (SEQ ID NO:13)
```

Fig. 11B

MSWGTELWDQFDSLDKHTQWGIDFLERYAKFVKERIEIEQNYAKQLRNLVKKYCPKRS
SKDEEPRFTSCVAFFNILNELNDYAGQREVVAEEMAHRVYGELMRYAHDLKTERKMHL
QEGRKAQQYLDMCWKQMDNSKKFERECREAEKAQQSYERLDNDTNATKADVEKAKQQ
LNLRTHMADENKNEYAAQLQNFNGEQHKHFYVVIPQIYKQLQEMDERRTIKLSECYRG
FADSERKVIPIISKCLEGMILAAKSVDERRDSQMVDSFKSGFEPPGDFPFEDYSQHI
YRTISDGTISASKQESGKMDAKTTVGKAKGKLWLFGKKPKGPALEDFSHLPPEQRRKK
LQQRIDELNRELQKESDQKDALNKMKDVYEKNPQMGDPGSLQPKLAETMNNIDRLRME
IHKNEAWLSEVEGKTGGRGDRRHSSDINHLVTQGRESPEGSYTDDANQEVRGPPQQHG
HHNEFDDEFEDDDPLPAIGHCKAIYPFDGHNEGTLAMKEGEVLYIEEDKGDGWTRAR
RQNGEEGYVPTSYIDVTLEKNSKGS (SEQ ID NO:14)

Fig. 12A

```
ATGTCAAATAACGGCCTAGACATTCAAGACAAACCCCAGCCCCTCCGATGAGAAATACCAGCACTA
TGATTGGAGCCGGCAGCAAAGATGCTGGAACCCTAAACCATGGTTCTAAACCTCTGCCTCCAAACC
AGAGGAGAAGAAAAGAAGGACCGATTTTACCTCCCTTCAGATTTGAACACAATTCATGTCGGTTTG
AAAGAGAAAGAGCGGCCAGAGTTTACGGGAGTTTACGGGAATGCCAGAGCAGTGGGCCCGCTTGCTTCAGACATCAAATAT
CACTAAGTCGTCACAGGGAGTTTACGGGAATGCCAGAGCAGTGGGCCCGCTTGCTTGGAGTTTACAACTCGAAG
AAGACATCCAACAGCCAGAATACATGAGCTTTACAGATAAGTCAGCTGAGGATTACAATTCTTCTA
ATGCCTTGAATGTGAAGGCTGTACCCCAGTGCTGTGTCTGAGACTCCTGCAGTCCACCAGTTTCAGAGAGATGAGGATGA
ACACGGTCTCTGATTGAACACCACTCCTGTCACTCCAACTCGGAGACGTGCTGGCTACATCTCCCATTTCAC
CTACTGAAAATAACACCACTCCTCCAGATGCTTTGACCCAGAAGCATAGTGAGTGTGGGCGATCCTAAGAAG
TAAAATGTCTGATGAGAGGTTTGAGAAGATCTTGGAGAAATTACGAAGGTGCTTCAGGCACCGTGTACACGAGGATGTGG
AATATACACGGTTGAGGAGGTGGCCATTAAGCAGATGAATCTTCAGCAGCCGTGTACACAGCCGTGTAC
CCACAGGACAGGAGGTGGCCATTAAGCAGATGAATCTTCAGCAGCCAAACATTGTGAATTACTTGGACAGTTACCTC
TAATGAGAGATCCTGGTCATGAGGGAAAACAGGAAAAACAAGAACCTGGCTGCCGTGTCTCCTTGCAGGCTCTCTGACATGTGGTGACAG
GTGGGAGATGAGCTGTGTGGTTGTTATGGAAGGCCAAATTGCAGCTGTGCCGTGAGTCGTTCTGCCAGGCTGTCTGACATGTGGTGACAG
GCATTCGAACCAGTCATTCAGACTTTGGATTCTGTGCACAGAGTTGTGACACGAGCCCAAGGCCCAAGGTTGACAT
GTCAAGCTAACTGACTTTGGATTCTGTGCACAGAGTTGTGACACGAGGCCTGTGTCAATGATTGAAGGAGACAGGTTGACAT
TAGGAACCCATACTGGGATGGCACCAGAGTTGTGACACGAAAGGCCTCCATACCTCAATGAAAAACCCT
CTGAGAGCCTTGTACCTCATTGCCAATGGACCCCATCGAAACTTCAGAACCCAGAAGAGGTTCAGCTAAGA
CTATCTTCCGGGACTTTCTGAACCGCTGTCTCGAGATGGATGTGGAGAAGAGAGGTTCAGCTGCA
GCTGCTACAGCATCAATTCCTGAAGATTGCCAAGCCCCTCTCCAGCCTCCACTCCACTGATTGCTGCA
GCTAAGGAGGCAACAAAGAACAATCACTAA (SEQ ID NO:15)
```

Fig. 12B

MSNNGLDIQDKPPAPPMRNTSTMIGAGSKDAGTLNHGSKPLPPNPEEKKKDRFYRSI
LPGDKTNKKEKERPEISLPSDFEHTIHVGFDAVTGEFTGMPEQWARLLQTSNITKSE
QKKNPQAVLDVLEFYNSKKTSNSQKYMSFTDKSAEDYNSSNALNVKAVSETPAVPVS
EDEDDDDATPPVIAPRPEHTKSVYTRSVIEPLPVTPTRDVATSPISPTENNTTPP
DALTRNTEKQKKPKMSDEEILEKLRSIVSVGDPKKKYTRFEKIGQGASGTVYTAMDV
ATGQEVAIKQMNLQQQPKKELINEILVMRENKNPNIVNYLDSYLVGDELWVMEYLA
GGSLTDVVTETCMDEGQIAAVCRECLQALEFLHSNQVIHRDIKSDNILLGMDGSVKLT
DFGFCAQITPEQSKRSTMVGTPYWMAPEVVTRKAYGPKVDIWSLGIMAIEMIEGEPPY
LNENPLRALYLIATNGTPELQNPEKLSAIFRDFLNRCLEMDVEKRGSAKELLQHFLK
IAKPLSSLTPLIAAAKEATKNNH (SEQ ID NO:16)

US 7,732,409 B2

ESPF$_U$ NUCLEIC ACIDS AND PROTEINS AND USES THEREOF

CROSS-REFERENCE TO RELATED APPLICATIONS

This application is a divisional application of U.S. application Ser. No. 11/134,563, filed May 20, 2005, now U.S. Pat. No. 7,250,261, issued Jul. 31, 2007 which claims benefit of U.S. Provisional Patent Application Ser. No. 60/573,600, filed on May 20, 2004. The contents of both prior applications are hereby incorporated by reference in their entirety.

STATEMENT OF FEDERALLY SPONSORED RESEARCH

This invention was made with Government support under grant number RO1-AI46454 awarded by the National Institute of Health. The Government has certain rights in the invention.

TECHNICAL FIELD

This invention relates to enteric organisms and actin pedestal formation by EspF$_U$.

BACKGROUND

Enteropathogenic *Escherichia coli* (EPEC) and enterohemorrhagic *E. coli* (EHEC) are closely related human pathogens that generate attaching and effacing (AE) lesions to colonize the intestine, damage the epithelium, and promote diarrheal illnesses (Donnenberg and Whittam, *J. Clin. Invest.* 107, 539-48 (2001); Nataro and Kaper, *Clin. Microbiol. Rev.* 11, 142-201 (1998)). EPEC and EHEC utilize a type-III-secretion-system to translocate effector proteins into mammalian host cells and form filamentous-actin "pedestals" that characterize AE lesions (Campellone and Leong, *Curr. Opin. Microbiol.* 6:82-90 (2003); Celli et al., *Cell Microbiol.* 2:1-9 (2000); Frankel et al., *Mol. Microbiol.* 30:911-21. (1998)).

A translocated effector protein expressed by both EHEC and EPEC is the translocated intimin receptor, Tir. Tir is delivered into the mammalian plasma membrane where it adopts a hairpin loop conformation (de Grado et al., *Cell. Microbiol.* 1:7-17 (1999); Hartland et al., *Mol. Microbiol.* 32:151-158 (1999); Kenny, *Mol. Microbiol.* 31, 1229-41 (1999)) and serves as a receptor for the bacterial surface adhesin intimin (Deibel et al., *Mol. Microbiol.* 28:463-74 (1998); Kenny et al., *Cell* 91:511-20 (1997)). The binding of intimin to the central extracellular domain of Tir promotes clustering of the N- and C-terminal cytoplasmic regions and initiates localized actin assembly beneath the plasma membrane (Campellone et al., *J. Cell Biol.* 164:407-16 (2004)). EHEC Tir and EPEC Tir are approximately 58% identical, and both are critical for the formation of actin pedestals by each pathogen (DeVinney et al., *Infect. Immun.* 67:2389-98 (1999); Kenny et al., *Cell* 91:511-20 (1997)).

EPEC Tir is both necessary and sufficient to recruit host Nck SH2/SH3 adaptors via a phosphorylated tyrosine. Nck, in turn, recruits and activates neuronal Wiskott-Aldrich syndrome protein (N-WASP), a key regulator of the Arp2/3 actin-nucleating machinery (Rohatgi et al., *J. Biol. Chem.* 276: 26448-26452 (2001)) required for actin pedestal formation (Lommel et al., *EMBO Rep.* 2:850-7 (2001)).

EHEC Tir recruits N-WASP and requires N-WASP for efficient pedestal formation (Goosney et al., *Infect and Immun.* 69: 3315-3322 (2001); Lommel et al., *Cell. Microbiol.* 6:243-54 (2004)). EHEC Tir, however, apparently lacks a phosphotyrosine residue capable of recruiting Nck. Thus, EHEC activates N-WASP and promotes actin pedestal formation using a Nck-independent mechanism. Furthermore, EHEC's Nck-independent mechanism of pedestal formation requires bacterial effectors in addition to Tir.

SUMMARY

The present invention is based, in part, on the identification of EspF$_U$ (EspF-like polypeptide encoded by a gene of the cryptic prophage CP-933U of enterohemorrhagic *Escherichia coli*) as a secreted protein that promotes actin pedestal formation by enteric organisms. An effector required for efficient actin pedestal formation in certain enteric organisms, EspF$_U$ can be used as a therapeutic target in various screens and assays. EspF$_U$ can also be used to induce pedestal formation in less dangerous model systems of highly pathogenic enteric organisms, e.g., enterohemorrhagic *E. coli* (EHEC). Nucleic acids, peptides and antibodies based on EspF$_U$ are also provided.

Accordingly, in one aspect, the invention provides isolated nucleic acids that encode EspF$_U$ polypeptides, e.g. a polypeptide that includes at least six (e.g., at least ten, twenty, thirty, forty, or fifty) amino acids of EspF$_U$, but less than all of the 384 amino acids of full length EspF$_U$, and the polypeptide binds to a neuronal Wiskott-Aldrich syndrome protein (N-WASP) polypeptide or restores the actin pedestal formation activity of enteropathogenic *E. coli* (EPEC) strain KC12. In some embodiments, the nucleic acid encodes a polypeptide that includes the amino acids of SEQ ID NO:4. In other embodiments, the nucleic acid encodes a polypeptide that is at least 75%, e.g., at least 80%, 85%, 90%, 95%, 96%, 97%, 98% or 99% identical to SEQ ID NO:2. In some embodiments, the nucleic acid is transformed into a bacterium, e.g., an *E. coli*, such as an enteropathogenic *E. coli* (EPEC). In further embodiments, the invention includes polypeptides encoded by the nucleic acids.

In another aspect, the invention provides kits for isolating a candidate compound or an EspF$_U$ modulating agent. In some embodiments, the kits include a nucleic acid molecule encoding a polypeptide that has at least six amino acids of EspF$_U$, and that binds to an N-WASP polypeptide or restores the actin pedestal formation activity of EPEC strain KC12; and the kits include instructions for using the nucleic acid in a method of identifying a compound that is a candidate compound or an EspF$_U$ modulating agent. In other embodiments, the kits include a polypeptide that has at least six amino acids of EspF$_U$, and that binds to an N-WASP polypeptide or restores the actin pedestal formation activity of EPEC strain KC12; and the kit includes instructions for using the polypeptide in a method of identifying a compound that is a candidate compound or an EspF$_U$ modulating agent. In a different aspect, the invention provides EspF$_U$ polypeptides. These polypeptides can include at least six amino acids of an EspF$_U$ polypeptide, e.g., a polypeptide at least 75% identical, e.g., 80%, 85%, 90%, 95%, 98%, 99%, or 100% identical to SEQ ID NO:2, and binds to an N-WASP polypeptide. In some embodiments, the polypeptides restore actin pedestal formation activity of EPEC strain KC12. In other embodiments fusion proteins comprising EspF$_U$ polypeptides are provided. In some embodiments, the fusion proteins include: (i) a first amino acid sequence that (a) includes the sequence of at least six amino acids of an EspF$_U$ polypeptide and (b) binds to an N-WASP polypeptide or restores the actin pedestal formation activity of EPEC strain KC12; and (ii) a second amino acid sequence unrelated to the first amino acid sequence, e.g., a reporter molecule. In other embodiments, the fusion proteins include (i) a first amino acid sequence that (a) includes the sequence of at least six amino acids of $EspF_U$ and (b) restores the actin pedestal formation activity of EPEC strain KC12; and (ii) a second amino acid sequence unrelated to the first amino acid sequence, e.g., a reporter molecule. Reporter molecules in a fusion protein can include a c-myc antigen, at least four, e.g., six, consecutive histidines, a chromophore, a fluorophore, a fluorescent protein, e.g., green fluorescent protein or a derivative of green fluorescent protein, biotin, horseradish peroxidase, alkaline phosphatase, β-galactosidase, glucose oxidase, invertase, luciferase, chloramphenicol acetyltransferase, β-glucuronidase, exoglucanase, or glucoamylase. In some embodiments, the peptides are conjugated to a hapten. In other embodiments, the peptides are formulated with an adjuvant. In some embodiments, the polypeptides comprise a 47-residue fragment of $EspF_U$ that binds N-WASP. In some embodiments, the polypeptides comprise immunogenic fragments of $EspF_U$.

In yet another aspect, the invention provides EPEC bacteria that express $EspF_U$ or an $EspF_U$ fragment that binds an N-WASP polypeptide and restores the actin pedestal formation activity of EPEC strain KC12. In some embodiments the EPEC bacteria also express (i) an EHEC Tir polypeptide and (ii) express lower than wild type levels of EPEC Tir, e.g. the bacteria express no functional EPEC Tir.

In still another aspect, the invention provides kits for reconstituting Nck-independent pedestal formation. In some embodiments, the kits include an EPEC bacterium that (a) expresses EHEC Tir and $EspF_U$; and (b) expresses lower than wild type levels of EPEC Tir; and the kits also include instructions for using the bacterium in an in vivo or in vitro assay that reconstitutes Nck-independent pedestal formation. In some embodiments, the kits further include a host cell. In different embodiments, the kits include an EPEC strain engineered to express an EHEC Tir polypeptide and the EPEC strain also expresses lower than wild type levels of EPEC Tir, e.g. no functional EPEC Tir; and the kits include a host cell comprising $EspF_U$.

In a different aspect, the invention provides purified antibodies that bind to an $EspF_U$ polypeptide, e.g., monoclonal or polyclonal antibodies. The invention also provides fragments and variants of antibodies that bind to an $EspF_U$ polypeptide.

In another aspect, the invention provides methods of identifying candidate compounds that bind to $EspF_U$. The methods include (i) contacting a test compound to an $EspF_U$ polypeptide, or a fragment thereof, and (ii) determining whether the test compound binds to the $EspF_U$ polypeptide, or fragment thereof. A test compound that binds an $EspF_U$ polypeptide, or fragment thereof, is a candidate compound.

In another aspect, the invention provides methods of identifying candidate compounds that inhibit protein-protein interactions between $EspF_U$ and $EspF_U$-interacting proteins, e.g., N-WASP, transducer of Cdc42-dependent actin assembly-1 (Toca-1), and p21-activated kinase 1 (Pak1). The methods include (i) contacting a test compound and (a) an $EspF_U$ polypeptide, or a fragment thereof, and (b) a polypeptide that includes an $EspF_U$-interacting protein, or a fragment thereof, and the method further includes (ii) determining whether the compound reduces binding interactions between (a) $EspF_U$ polypeptide, or a fragment thereof, and (b) the polypeptide that includes an $EspF_U$-interacting protein, or a fragment thereof A test compound that reduces binding interactions between the polypeptide of (a) and the polypeptide of (b) is a candidate compound that inhibits protein-protein interactions between $EspF_U$ and an $EspF_U$-interacting protein.

In a different aspect, the invention provides methods of identifying an $EspF_U$ modulating agent by: (i) infecting a host cell with an enteric organism that induces Nck-independent pedestal formation; (iii) contacting a host cell and (a) test compound or (b) a candidate compound; and (iii) determining whether the compound disrupts pedestal formation by the enteric organism in the host cell. Compounds that disrupt pedestal formation by an enteric organism are $EspF_U$ modulating agents. In some embodiments, the methods are carried out in a subject. In other embodiments the method is carried out in vitro, e.g., in a cultured cell or a cell from a subject ex vivo.

In yet another aspect, the invention includes pharmaceutical compositions that includes a candidate compound or a modulating agent identified by the methods disclosed herein formulated with a pharmaceutically acceptable carrier. In a related aspect, the invention provides methods of treatment that include identifying a patient in need of treatment or reduction of infection by an enteric organism, and administering the pharmaceutical composition that includes a candidate compound or a modulating agent identified by the methods disclosed herein, in an amount sufficient to treat or reduce infection by an enteric organism. In some embodiments, the methods of treatment inhibit the release of a Shiga-like toxin from an enteric organism.

In another aspect, the invention includes methods of reconstituting Nck-independent pedestal formation by enteric organisms. In some embodiments, the methods include (i) providing an EPEC bacterium (e.g., a KC12 derivative of EPEC) that (a) expresses an EHEC Tir polypeptide, (b) expresses an $EspF_U$ polypeptide, and (c) expresses lower than wild type levels of EPEC Tir (e.g., no functional EPEC Tir); and (ii) contacting the bacterium with a host cell for an enteric organism (e.g., a cultured cell). In other embodiments, the methods include (i) providing a host cell with $EspF_U$; and (ii) contacting the host cell with an EPEC strain that (a) expresses EHEC Tir, or a functional fragment thereof, and (b) expresses lower than wild type levels of EPEC Tir (e.g., no functional EPEC Tir); to thereby reconstitute efficient Nck-independent pedestal formation In still another aspect, the invention provides methods of identifying an $EspF_U$ modulating agent that regulates $EspF_U$ expression by contacting a test compound and an $EspF_U$ polypeptide expressing bacterium and monitoring expression of $EspF_U$ polypeptide in the bacterium. A compound that regulates expression of $EspF_U$ polypeptide in the bacterium is an $EspF_U$ modulating agent.

In still another aspect, the invention provides methods of identifying $EspF_U$ modulating agents by (i) contacting a test compound with the components of a cell free actin pedestal reconstitution assay, wherein the components include an $EspF_U$ polypeptide; and (ii) determining whether the test compound inhibits the formation of actin structures by the assay components wherein a compound that or inhibits the formation of actin structures by the components of the assay is an $EspF_U$ modulating agent.

In still another aspect, the invention provides methods of diagnosing or detect an EHEC infection by providing a sample, e.g., from a subject (e.g., a stool sample or biopsy) suspected of having an EHEC infection and detecting an $EspF_U$ nucleic acid or polypeptide in the sample. In cases where an EspFU nucleic acid or polypeptide is detected in the sample, the subject can be treated with a treatment that does not enhance production of Shiga-like toxin.

A "pedestal forming enteric organism" is an enteric bacterium, e.g., an EHEC or EPEC, that can induce the formation of an actin pedestal structure in a host cell.

A "subject" can be a human or an animal, e.g., a mammal such as a mouse, rat, guinea pig, hamster, dog, cat, pig, horse, goat, cow, monkey, or ape.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

This application provides methods of screening for compounds that can inhibit EHEC infection. Other features and advantages of the invention will be apparent from the following detailed description, and from the claims.

BRIEF DESCRIPTION OF DRAWINGS

FIG. 1A is a series of fluorescent microscopy images of HeLa cells infected either with wild type EHEC, with EHECΔCP$_U$ and a control vector, or with EHECΔCP$_U$ and a vector expressing EspF$_U$. Infected cells were treated with DAPI to identify bacteria and with phalloidin to stain F-actin. Pedestal formation efficiencies were quantitated by measuring the % of cell-associated bacteria that were also associated with intense F-actin staining. Data are the means (+/−SD) of three separate experiments.

FIG. 1B is a series of fluorescent microscopy images of HeLa cells infected with the depicted EHEC strains, treated as described in FIG. 1A and quantitated for pedestal formation.

FIG. 4A is a series of fluorescent microscopy images of HeLa cells infected with KC12 expressing EspF$_U$-myc. Cells were treated with DAPI to identify bacteria and with antibodies to visualize HA-tagged Tir, myc-tagged EspF$_U$, or endogenous N-WASP FIG. 4B is an image of Western blots for HA and myc antigen. Lysates from HeLa cells infected with KC12 harboring p-myc or pEspFU-myc were either untreated (lanes 1-2), or were subjected to immunoprecipitation with a control antibody (lanes 3-4) or an anti-HA antibody (lanes 5-6). Cell lysates (lanes 1-2) and immunoprecipitates (lanes 3-6) were then immunoblotted for HA-tagged Tir and myc-tagged EspF$_U$.

FIG. 4C is an image of Western blots for myc antigen and N-WASP. Lysates from HeLa cells infected with KC12 harboring p-myc or pEspFU-myc were either left untreated (lanes 2-3), or were supplemented with purified recombinant N-WASP prior to immunoprecipitation with a control antibody (lanes 4-5) or an anti-myc antibody (lanes 6-7). Lane 1 shows 1/10 of the amount of N-WASP used to supplement HeLa lysates.

FIG. 5A is a nucleotide sequence (SEQ ID NO: 1) encoding full length EspF$_U$.

FIG. 5B is the amino acid sequence (SEQ ID NO:2) of full length EspF$_U$.

FIG. 6A is a nucleotide sequence (SEQ ID NO:3) encoding a C-terminal fragment of EspF$_U$ that corresponds to amino acids 80-384 of full-length EspF$_U$.

FIG. 6B is the amino acid sequence of a C-terminal fragment of EspF$_U$ corresponding to amino acids 80-384 of full-length EspF$_U$ (SEQ ID NO:4). This proline rich C-terminal fragment binds to N-WASP.

FIG. 7A is a nucleotide sequence encoding an exemplary human N-WASP polypeptide amino acid sequence (SEQ ID NO:5).

FIG. 7B is an exemplary human N-WASP polypeptide amino acid sequence (SEQ ID NO:6).

FIG. 8A is a nucleotide sequence encoding an exemplary rat N-WASP polypeptide amino acid sequence (SEQ ID NO:7).

FIG. 8B is an exemplary rat N-WASP polypeptide amino acid sequence (SEQ ID NO:8).

FIG. 9A is a nucleotide sequence (SEQ ID NO:9) encoding the GTPase binding domain (GBD) of an exemplary rat N-WASP polypeptide amino acid sequence.

FIG. 9B is the GBD of an exemplary rat N-WASP polypeptide amino acid sequence (SEQ ID NO:10).

FIG. 10A is a nucleotide sequence (SEQ ID NO: 11) encoding an exemplary EHEC Tir polypeptide amino acid sequence.

FIG. 10B is an exemplary EHEC Tir polypeptide amino acid sequence (SEQ ID NO:12).

FIG. 11A is a nucleotide sequence (SEQ ID NO: 13) encoding an exemplary human Toca-1 polypeptide amino acid sequence.

FIG. 11B is an exemplary human Toca-1 polypeptide amino acid sequence (SEQ ID NO: 14).

FIG. 12A is a nucleotide sequence (SEQ ID NO: 15) encoding an exemplary human Pak1 polypeptide amino acid sequence.

FIG. 12B is an exemplary human Pak1 polypeptide amino acid sequence (SEQ ID NO: 16).

Like reference symbols in the various drawings indicate like elements.

DETAILED DESCRIPTION

Figure 2:
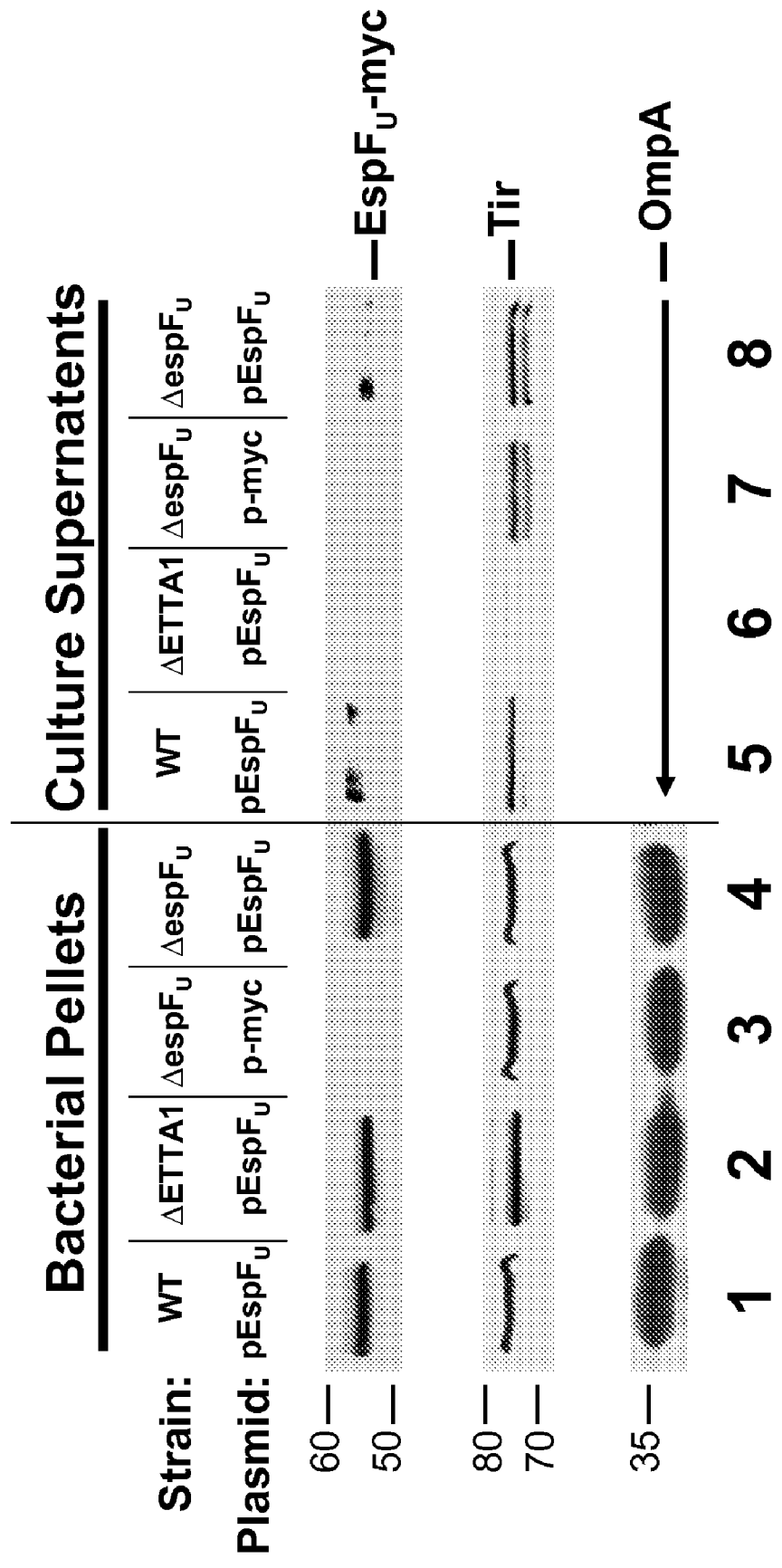
FIG. 2 is an image of Western blots for Tir and EspFU-myc in cell extracts from wild type EHEC, from an EHEC strain lacking ETTA1, or from an EHEC strain lacking EspF$_U$ transformed with either a control plasmid or a plasmid encoding myc-tagged EspF$_U$. Immunoblotting for bacterial outer membrane protein A (OmpA) demonstrated similar protein quantities within pellet fractions (lanes 1-4).

The present invention is based, in part, on the discovery that an EspF-like protein encoded by a gene of the cryptic prophage CP-933U of enterohemorrhagic E. coli (EspF$_U$) is required for efficient Nck-independent pedestal formation. Inactivation of the gene encoding EspF$_U$ in certain enteric organisms inhibits SH2/SH3 adaptor protein Nck-independent actin pedestal formation, and expression of EspF$_U$ in combination with the translocated intimin receptor (Tir) can induce pedestal formation. EspF$_U$ nucleic acids and peptides are useful, for example as targets for identifying compounds for treating infection and/or inhibiting colonization by enteric organisms.

Nucleic Acids, Proteins, Vectors, and Host Cells

In one aspect, the invention includes nucleic acids encoding EspF$_U$ polypeptides, and fragments and variants thereof. A nucleic acid sequence encoding an exemplary EspF$_U$ polypeptide is provided in SEQ ID NO: 1 and FIG. 5A. The amino acid sequence encoded by SEQ ID NO:1 is provided in SEQ ID NO:2 and FIG. 5B.

Included within the present invention are useful fragments of EspF$_U$ polypeptides. For example, useful fragments of EspF$_U$ polypeptides include fragments that bind to neuronal Wiskott-Aldrich syndrome protein (N-WASP), e.g., a fragment corresponding to amino acids from about 80 to about 384, inclusive, of SEQ ID NO:2 (SEQ ID NO:4; FIG. 6B), which is encoded by SEQ ID NO:3 (FIG. 6A). An exemplary human N-WASP amino acid sequence shown in FIG. 7. Other useful fragments of EspF$_U$ include polypeptides having the amino acid sequence of SEQ ID NO:4 and that do not include all of the amino acids of SEQ ID NO:2.

Also included within the invention are nucleic acids that encode useful fragments of EspF$_U$ polypeptides. For example, the invention includes nucleic acids that encode EspF$_U$ fragments that bind to N-WASP; e.g., nucleic acids that encode amino acids from about 80 to about 384, inclusive, of SEQ ID NO:2.

EspF$_U$ nucleic acids described herein include both RNA and DNA, including genomic DNA and synthetic (e.g., chemically synthesized) DNA. Nucleic acids can be double-stranded or single-stranded. Where single-stranded, the nucleic acid can be a sense strand or an antisense strand. Nucleic acids can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

The term "isolated nucleic acid" means a nucleic acid, e.g., DNA or RNA, that is not immediately contiguous with both of the coding sequences with which it is immediately contiguous (one on the 5' end and one on the 3' end) in the naturally occurring genome of the organism from which it is derived. Thus, in one embodiment, an isolated EspF$_U$ nucleic acid includes some or all of the 5' non-coding (e.g., promoter) sequences that are immediately contiguous to the EspF$_U$ nucleic acid coding sequence. The term includes, for example, recombinant DNA that is incorporated into a vector, into an autonomously replicating plasmid or virus, or into the genomic DNA of a prokaryote or eukaryote, or which exists as a separate molecule (e.g., a genomic DNA fragment produced by PCR or restriction endonuclease treatment) independent of other sequences. It also includes a recombinant DNA that is part of a hybrid gene encoding an additional polypeptide sequence.

The term "purified" refers to an EspF$_U$ nucleic acid (or EspF$_U$ polypeptide) that is substantially free of cellular or viral material with which it is naturally associated, or culture medium (when produced by recombinant DNA techniques), or chemical precursors or other chemicals (when chemically synthesized). Moreover, an isolated nucleic acid fragment is a nucleic acid fragment that is not naturally occurring as a fragment and would not be found in the natural state.

In some embodiments, the invention includes nucleic acid sequences that are substantially identical to an EspF$_U$ nucleic acid. A nucleic acid sequence that is "substantially identical" to an EspF$_U$ nucleic acid is at least 75% identical (e.g., at least about 80%, 85%, 90%, or 95% identical) to the EspF$_U$ nucleic acid sequences represented by SEQ ID NO:1 or 3. For purposes of comparison of nucleic acids, the length of the reference nucleic acid sequence will be at least 50 nucleotides, but can be longer, e.g., at least 60 or more nucleotides.

To determine the percent identity of two amino acid or nucleic acid sequences, the sequences are aligned for optimal comparison purposes (i.e., gaps can be introduced as required in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of overlapping positions×100). The two sequences may be of the same length.

The percent identity or homology between two sequences can be determined using a mathematical algorithm. A non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al, (1990); *J. Mol. Biol.* 215:403-410. BLAST nucleotide searches can be performed with the NBLAST program, score=100, wordlength=12 to obtain nucleotide sequences homologous to EspF$_U$ nucleic acid molecules of the invention. BLAST protein searches can be performed with the XBLAST program, score=50, wordlength=3 to obtain amino acid sequences homologous to EspF$_U$ protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used. See online at ncbi.nlm.nih.gov.

In other embodiments, the invention includes variants, homologs, and/or fragments of certain EspF$_U$ nucleic acids, e.g., variants, homologs, and/or fragments of the EspF$_U$ nucleic acid sequences represented by SEQ ID NOs: 1 or 3. The terms "variant" or "homolog" in relation to EspF$_U$ nucleic acids include any substitution, variation, modification, replacement, deletion, or addition of one (or more) nucleotides from or to the sequence of an EspF$_U$ nucleic acid. The resultant nucleotide sequence may encode an EspF$_U$ polypeptide that has at least 50% of a biological activity (e.g., binding to N-WASP, Toca-1, or Pak1, or Nck-independent actin pedestal formation) of the referenced EspF$_U$ polypeptides (e.g., SEQ ID NOs: 2 and 4). In particular, the term "homolog" covers homology with respect to structure and/or function as long as the resultant nucleotide sequence encodes or is capable of encoding an $EspF_U$ polypeptide that has at least 50% of the biological activity of $EspF_U$ encoded by a sequence shown herein as SEQ ID NOs: 1 and 3. With respect to sequence homology, there is at least 75% (e.g., 85%, 90%, 95%, 98%, or 100%) homology to the sequence shown as SEQ ID NO:1 or 3. The term "homology" as used herein can be equated with the term "identity."

"Substantial homology" or "substantially homologous," where homology indicates sequence identity, means at least 75% identical (e.g., at least about 80%, 85%, 90%, or 95% identical) sequence identity, as judged by direct sequence alignment and comparison. "Substantial homology" when assessed by the BLAST algorithm equates to sequences which match with an EXPECT value of at least about 7, e.g., at least about 9, 10, or more. The default threshold for EXPECT in BLAST searching is usually 10.

Also included within the scope of the present invention are certain alleles of certain $EspF_U$ genes. As used herein, an "allele" or "allelic sequence" is an alternative form of $EspF_U$ or N-WASP. Alleles can result from changes in the nucleotide sequence, and generally produce altered mRNAs or polypeptides whose structure or function may or may not be altered. Any given gene can have none, one, or more than one allelic form. Common changes that give rise to alleles are generally ascribed to deletions, additions, or substitutions of amino acids. Each of these types of changes can occur alone, or in combination with the others, one or more times in a given sequence.

The invention also includes nucleic acids that hybridize, e.g., under stringent hybridization conditions (as defined herein) to all or a portion of the nucleotide sequences represented by SEQ ID NOs: 1 or 3, or a complement thereof. The hybridizing portion of the hybridizing nucleic acids is typically at least 15 (e.g., 20, 30, or 50) nucleotides in length. The hybridizing portion of the hybridizing nucleic acid is at least about 75%, e.g., at least about 80%, 95%, 98% or 100%, identical to the sequence of a portion or all of a nucleic acid encoding an $EspF_U$ polypeptide, or to its complement. Hybridizing nucleic acids of the type described herein can be used as a cloning probe, a primer (e.g., a PCR primer), or a diagnostic probe. Nucleic acids that hybridize to the nucleotide sequence represented by SEQ ID NO: 1 or 3, are considered "antisense oligonucleotides."

High stringency conditions are hybridizing at 68° C. in 5×SSC/5×Denhardt's solution/1.0% SDS, or in 0.5 M $NaHPO_4$ (pH 7.2)/1 mM EDTA/7% SDS, or in 50% formamide/0.25 M $NaHPO_4$ (pH 7.2)/0.25 M $NaCl_1$/mM EDTA/7% SDS; and washing in 0.2×SSC/0.1% SDS at room temperature or at 42° C., or in 0.1×SSC/0.1% SDS at 68° C., or in 40 mM $NaHPO_4$ (pH 7.2)/1 mM EDTA/5% SDS at 50° C., or in 40 mM $NaHPO_4$ (pH 7.2) 1 mM EDTA/1% SDS at 50° C. Stringent conditions include washing in 3×SSC at 42° C. The parameters of salt concentration and temperature can be varied to achieve the optimal level of identity between the probe and the target nucleic acid. Additional guidance regarding such conditions is available in the art, for example, by Sambrook et al., 1989, Molecular Cloning, A Laboratory Manual, Cold Spring Harbor Press, N.Y.; and Ausubel et al., (eds.), 1995, Current Protocols in Molecular Biology, (John Wiley & Sons, N.Y.) at Unit 2.10.

Also included in the invention are genetic constructs (e.g., vectors and plasmids) that include an $EspF_U$ nucleic acid described herein, operably linked to a transcription and/or translation sequence to enable expression, e.g., expression vectors. A selected nucleic acid, e.g., a DNA molecule encoding an $EspF_U$ polypeptide, is "operably linked" to another nucleic acid molecule, e.g., a promoter, when it is positioned either adjacent to the other molecule or in the same or other location such that the other molecule can control transcription and/or translation of the selected nucleic acid.

Also included in the invention are various engineered cells, e.g., transformed host cells, which contain an $EspF_U$ nucleic acid described herein. A transformed cell is a cell into which (or into an ancestor of which) has been introduced, by means of recombinant DNA techniques, a nucleic acid encoding an $EspF_U$ polypeptide. Both prokaryotic and eukaryotic cells are included. Mammalian cells transformed with an $EspF_U$ nucleic acid can include host cells for an attaching enteric organism, e.g., intestinal cells, HeLa cells, and mouse embryonic fibroblasts. Prokaryotic cells can include bacteria, e.g., *Escherichia coli*, and EPEC strains. An engineered cell exemplary of the type included in the invention is the EPEC KC12 strain that expresses $EspF_U$, as described in the Examples section, below.

Certain $EspF_U$ polypeptides are also included within the present invention. Examples of such $EspF_U$ polypeptides are EHEC $EspF_U$ polypeptides and fragments, such as the one shown in FIG. 8B and SEQ ID NO:2. Also included within the present invention are certain fragments of $EspF_U$ polypeptides, e.g., fragments of FIG. 9B and SEQ ID NO:4. Fragments of $EspF_U$ polypeptides may include at least one binding domain, or other useful portion of a full-length $EspF_U$ polypeptide. For example, useful fragments of $EspF_U$ polypeptides include, but are not limited to, fragments having N-WASP, Toca-1 or Pak1 binding activity, e.g., amino acids about 80 to 384, inclusive, of SEQ ID NO:2, and portions of such fragments.

The terms "protein" and "polypeptide" both refer to any chain of amino acids, regardless of length or post-translational modification (e.g., glycosylation or phosphorylation). Thus, the terms "$EspF_U$ protein," and "$EspF_U$ polypeptide," include full-length naturally occurring isolated proteins, as well as recombinantly or synthetically produced polypeptides that correspond to the full-length naturally occurring proteins, or to a fragment of the full-length naturally occurring or synthetic polypeptide.

As discussed above, the term "$EspF_U$ polypeptide" includes biologically active fragments of naturally occurring or synthetic $EspF_U$ polypeptides. The term "N-WASP polypeptide" includes biologically active fragments of naturally occurring or synthetic N-WASP polypeptides. Fragments of a protein can be produced by any of a variety of methods known to those skilled in the art, e.g., recombinantly, by proteolytic digestion, and/or by chemical synthesis. Internal or terminal fragments of a polypeptide can be generated by removing one or more nucleotides from one end (for a terminal fragment) or both ends (for an internal fragment) of a nucleic acid that encodes the polypeptide. Expression of such mutagenized DNA can produce polypeptide fragments. Digestion with "end-nibbling" endonucleases can thus generate DNAs that encode an array of fragments. DNAs that encode fragments of a protein can also be generated, e.g., by random shearing, restriction digestion, chemical synthesis of oligonucleotides, amplification of DNA using the polymerase chain reaction, or a combination of the above-discussed methods. Fragments can also be chemically synthesized using techniques known in the art, e.g., conventional Merrifield solid phase FMOC or t-Boc chemistry. For example, peptides of the present invention can be arbitrarily divided into fragments of desired length with no overlap of the fragments, or divided into overlapping fragments of a desired length.

A purified or isolated compound is a composition that is at least 60% by weight the compound of interest, e.g., an EspF$_U$ polypeptide or antibody. In general, the preparation is at least 75% (e.g., at least 90%, 95%, or even 99%) by weight the compound of interest. Purity can be measured by any appropriate standard method, e.g., column chromatography, polyacrylamide gel electrophoresis, or HPLC analysis.

In certain embodiments, EspF$_U$ polypeptides include sequences substantially identical to all or portions of a naturally occurring EspF$_U$ polypeptides. Polypeptides "substantially identical" to the EspF$_U$ polypeptide sequences described herein have an amino acid sequence that is at least 65% (e.g., at least 75%, 80%, 85%, 90%, 95% or 99%, e.g., 100%), identical to the amino acid sequences of the EspF$_U$ polypeptides represented by SEQ ID NOs: 2 and 4 (measured as described herein). For purposes of comparison, the length of the reference EspF$_U$ polypeptide sequence is at least 16 amino acids, e.g., at least 20 or 25 amino acids.

In the case of polypeptide sequences that are less than 100% identical to a reference sequence, the non-identical positions are preferably, but not necessarily, conservative substitutions for the reference sequence. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Where a particular polypeptide is said to have a specific percent identity to a reference polypeptide of a defined length, the percent identity is relative to the reference polypeptide. Thus, a polypeptide that is 50% identical to a reference polypeptide that is 100 amino acids long can be a 50 amino acid polypeptide that is completely identical to a 50 amino acid long portion of the reference polypeptide. It also might be a 100 amino acid long polypeptide that is 50% identical to the reference polypeptide over its entire length.

EspF$_U$ polypeptides of the invention include, but are not limited to, recombinant polypeptides and natural polypeptides. Also included are nucleic acid sequences that encode forms of EspF$_U$ polypeptides in which naturally occurring amino acid sequences are altered or deleted. Certain nucleic acids of the present invention may encode polypeptides that are soluble under normal physiological conditions.

Also within the invention are nucleic acids encoding fusion proteins in which a portion of an EspF$_U$ polypeptide is fused to an unrelated polypeptide (e.g., a marker polypeptide or a fusion partner) to create a fusion protein. For example, the polypeptide can be fused to a hexa-histidine tag or a FLAG tag to facilitate purification of bacterially expressed polypeptides or to a hemagglutinin tag or a FLAG tag to facilitate purification of polypeptides expressed in eukaryotic cells. The invention also includes, for example, isolated polypeptides (and the nucleic acids that encode these polypeptides) that include a first portion and a second portion; the first portion includes, e.g., an EspF$_U$ polypeptide, and the second portion includes an immunoglobulin constant (Fc) region or a detectable marker.

The fusion partner can be, for example, a polypeptide that facilitates secretion, e.g., a secretory sequence. Such a fused polypeptide is typically referred to as a preprotein. The secretory sequence can be cleaved by the host cell to form the mature protein. Also within the invention are nucleic acids that encode an EspF$_U$ polypeptide fused to a polypeptide sequence to produce an inactive preprotein. Preproteins can be converted into the active form of the protein by removal of the inactivating sequence.

Antibodies

The invention features purified or isolated antibodies that bind, e.g., specifically bind, to an EspF$_U$ polypeptide, i.e., anti-EspF$_U$ antibodies. An antibody "specifically binds" to a particular antigen, e.g., an EspF$_U$ polypeptide, when it binds to that antigen, but recognizes and binds to a lesser extent (e.g., does not recognize and bind) to other molecules in a sample, e.g., a biological sample that includes an EspF$_U$ polypeptide.

Antibodies of the invention include monoclonal antibodies, polyclonal antibodies, humanized or chimeric antibodies, single chain antibodies, Fab fragments, F(ab')$_2$ fragments, and molecules produced using a Fab expression library.

An example of a type of antibody included in the present invention is a polyclonal anti-EspF$_U$ antibody. Such an antibody can be produced, e.g., as follows: a peptide corresponding to about fifteen consecutive EspF$_U$ amino acid residues (from e.g., of SEQ ID NO:2 or SEQ ID NO:4) is obtained, coupled to ovalbumin, and injected into rabbits to raise rabbit polyclonal antibodies.

As used herein, the term "antibody" refers to a protein comprising at least one, e.g., two, heavy (H) chain variable regions (abbreviated herein as VH), and at least one, e.g., two light (L) chain variable regions (abbreviated herein as VL). The term "antibody" can also encompass antibodies that include only one heavy chain, e.g., camelid antibodies. The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al., Sequences of Proteins of Immunological Interest, Fifth Edition, U.S. Department of Health and Human Services, NIH Publication No. 91-3242 (1991), and Chothia, et al., J. Mol. Biol. 196:901-917 (1987)). Each VH and VL is composed of three CDR's and four FRs, arranged from amino-terminus to carboxy-terminus in the following order: FR1, CDR1, FR2, CDR2, FR3, CDR3, FR4.

An anti-EspF$_U$ antibody can further include a heavy and light chain constant region, to thereby form a heavy and light immunoglobulin chain, respectively. The antibody can be a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2, and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

An "EspF$_U$ binding fragment" of an antibody refers to one or more fragments of a full-length antibody that retain the ability to specifically bind to EspF$_U$ polypeptide or a portion thereof. Examples of EspF$_U$ polypeptide binding fragments of an anti-EspF$_U$ antibody include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., *Nature* 341:544-546 (1989)), which consists of a VH domain; and (vi) an isolated complementarity determining region (CDR). Furthermore, although the two domains of the Fv fragment, VL and VH, are encoded by separate genes, they can be joined, using recombinant methods, by a synthetic linker that enables them to be made as a single protein chain in which the VL and VH regions pair to form monovalent molecules (known as single chain Fv (scFv); see e.g., Bird et al., *Science* 242:423-426 (1988); and Huston et al., *Proc. Natl. Acad. Sci. USA* 85:5879-5883 (1988)). Such single chain antibodies are also encompassed within the term "EspF$_U$ binding fragment" of an antibody. These antibody fragments can be obtained using conventional techniques known to those with skill in the art.

To produce antibodies, EspF$_U$ polypeptides (or antigenic fragments (e.g., fragments of EspF$_U$ that appear likely to be antigenic by criteria such as high frequency of charged residues) or analogs of such polypeptides), e.g., those produced by recombinant or peptide synthetic techniques (see, e.g., Stewart et al., *Solid Phase Peptide Synthesis*, (1989), W. H. Freeman Co., San Francisco; Ausubel et al., supra), can be used. In general, the polypeptides can be coupled to a carrier protein, such as KLH, as described in Ausubel et al., supra, mixed with an adjuvant, and injected into a host mammal. A "carrier" is a substance that confers stability on, and/or aids or enhances the transport or immunogenicity of, an associated molecule. For example, EspF$_U$ or fragments thereof can be generated using standard techniques of PCR, and can be cloned into a pGEX expression vector (Ausubel et al., supra). Fusion proteins can be expressed in *E. coli* and purified using a glutathione agarose affinity matrix as described in Ausubel, et al., supra.

Typically, to produce antibodies, various host animals are injected with EspF$_U$ polypeptides. Examples of suitable host animals include rabbits, mice, guinea pigs, and rats. Various adjuvants can be used to increase the immunological response, depending on the host species, including but not limited to Freund's (complete and incomplete adjuvant), adjuvant mineral gels such as aluminum hydroxide, surface active substances such as lysolecithin, pluronic polyols, polyanions, peptides, oil emulsions, keyhole limpet hemocyanin, dinitrophenol, BCG (bacille Calmette-Guerin) and *Corynebacterium parvum* Such procedures result in the production of polyclonal antibodies, i.e., heterogeneous populations of antibody molecules derived from the sera of the immunized animals. Antibodies can be purified from blood obtained from the host animal, for example, by affinity chromatography methods in which the EspF$_U$ polypeptide antigen is immobilized on a resin.

The present invention also includes anti-EspF$_U$ monoclonal antibodies. Monoclonal antibodies (mAbs), which are homogeneous populations of antibodies to a particular antigen, can be prepared using EspF$_U$ polypeptides and standard hybridoma technology (see, e.g., Kohler et al., *Nature*, 256: 495, 1975; Kohler et al., *Eur. J. Immunol*, 6:511, 1976; Kohler et al., *Eur. J. Immunol.*, 6:292, 1976; Hammerling et al., In *Monoclonal Antibodies and T Cell Hybridomas*, Elsevier, N.Y., 1981; Ausubel et al., supra).

Typically, monoclonal antibodies are produced using any technique that provides for the production of antibody molecules by continuous cell lines in culture, such as those described in Kohler et al., *Nature*, 256:495, 1975, and U.S. Pat. No. 4,376,110; the human B-cell hybridoma technique (Kosbor et al., *Immunology Today*, 4:72, 1983; Cole et al., *Proc. Natl. Acad. Sci. USA,* 80:2026, 1983); and the EBV-hybridoma technique (Cole et al., *Monoclonal Antibodies and Cancer Therapy*, Alan R. Liss, Inc., pp. 77-96, 1983). Such antibodies can be of any immunoglobulin class including IgG, IgM, IgE, IgA, IgD, and any subclass thereof. The hybridomas producing the mAbs of this invention can be cultivated in vitro or in vivo.

Once produced, polyclonal or monoclonal antibodies can be tested for recognition, e.g., specific recognition, of EspF$_U$ in an immunoassay, such as a Western blot or immunoprecipitation analysis using standard techniques, e.g., as described in Ausubel et al., supra. Antibodies that specifically bind to an EspF$_U$ polypeptide, or conservative variants thereof, are useful in the invention. For example, such antibodies can be used in an immunoassay to detect an EspF$_U$ polypeptide in a sample, e.g., a tissue sample.

Alternatively or in addition, an antibody can be produced recombinantly, e.g., produced by phage display or by combinatorial methods as described in, e.g., Ladner et al., U.S. Pat. No. 5,223,409; Kang et al., International Publication No. WO 92/18619; Dower et al., International Publication No. WO 91/17271; Winter et al., International Publication WO 92/20791; Markland et al., International Publication No. WO 92/15679; Breitling et al., International Publication WO 93/01288; McCafferty et al., International Publication No. WO 92/01047; Garrard et al., International Publication No. WO 92/09690; Ladner et al., International Publication No. WO 90/02809; Fuchs et al., (1991) *Bio/Technology* 9:1370-1372; Hay et al., (1992) *Hum. Antibod. Hybridomas* 3:81-85; Huse et al., (1989) *Science* 246:1275-1281; Griffths et al., (1993) *EMBO J.* 12:725-734; Hawkins et al., (1992) *J. Mol. Biol.* 226:889-896; Clackson et al., (1991) *Nature* 352:624-628; Gram et al, (1992) *Proc. Natl. Acad. Sci. USA* 89:3576-3580; Garrad et al., (1991) *Bio/Technology* 9:1373-1377; Hoogenboom et al., (1991) *Nuc. Acid Res.* 19:4133-4137; and Barbas et al., (1991) *Proc. Natl. Acad. Sci. USA* 88:7978-7982.

Anti-EspF$_U$ antibodies can be fully human antibodies (e.g., an antibody made in a mouse which has been genetically engineered to produce an antibody from a human immunoglobulin sequence), or non-human antibodies, e.g., rodent (mouse or rat), goat, primate (e.g., monkey), camel, donkey, porcine, or fowl antibodies.

An anti-EspF$_U$ antibody can be one in which the variable region, or a portion thereof, e.g., the CDRs, are generated in a non-human organism, e.g., a rat or mouse. The anti-EspF$_U$ polypeptide antibody can also be, for example, chimeric, CDR-grafted, or humanized antibodies. The anti-EspF$_U$ polypeptide antibody can also be generated in a non-human organism, e.g., a rat or mouse, and then modified, e.g., in the variable framework or constant region, to decrease antigenicity in a human.

Techniques developed for the production of "chimeric antibodies" (Morrison et al., *Proc. Natl. Acad. Sci.*, 81:6851, 1984; Neuberger et al., *Nature*, 312:604, 1984; Takeda et al., *Nature*, 314:452, 1984) can be used to splice the genes from a mouse antibody molecule of appropriate antigen specificity together with genes from a human antibody molecule of appropriate biological activity. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; and U.S.

Pat. Nos. 4,946,778 and 4,704,692) can be adapted to produce single chain antibodies against an EspFU polypeptide. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments can include but are not limited to F(ab')$_2$ fragments, which can be produced by pepsin digestion of the antibody molecule, and Fab fragments, which can be generated by reducing the disulfide bridges of F(ab')$_2$ fragments. Alternatively, Fab expression libraries can be constructed (Huse et al., Science, 246:1275, 1989) to allow rapid and easy identification of monoclonal Fab fragments with the desired specificity.

Polyclonal and monoclonal antibodies (or fragments thereof) that specifically bind to an EspF$_U$ polypeptide can be used, for example, to detect expression of EspF$_U$ in various tissues, fluids, excreted matter from a patient. For example, an EspF$_U$ polypeptide can be detected in conventional immunoassays of biological tissues or extracts. Examples of suitable assays include, without limitation, Western blotting, ELISAs, radioimmune assays, and the like.

Methods for Identifying Compounds Capable of Modulating EspF$_U$ Activity

The invention provides methods for identifying compounds, e.g., small organic or inorganic molecules (e.g., those with a molecular weight of less than 1,000 Da), oligopeptides, oligonucleotides, or carbohydrates, capable of modulating (i.e., reducing or increasing) EspF$_U$ activity and, therefore, affecting pedestal formation, infection, and/or intestinal colonization by an enteric organism.

Libraries of Test Compounds

In certain embodiments, screens of the present invention utilize libraries of test compounds. As used herein, a "test compound" can be any chemical compound, for example, a macromolecule (e.g., a polypeptide, a protein complex, glycoprotein, or a nucleic acid) or a small molecule (e.g., an amino acid, a nucleotide, an organic or inorganic compound). A test compound can have a formula weight of less than about 10,000 grams per mole, less than 5,000 grams per mole, less than 1,000 grams per mole, or less than about 500 grams per mole. The test compound can be naturally occurring (e.g., an herb or a natural product), synthetic, or can include both natural and synthetic components. Examples of test compounds include peptides, peptidomimetics (e.g., peptoids), amino acids, amino acid analogs, polynucleotides, polynucleotide analogs, nucleotides, nucleotide analogs, and organic or inorganic compounds, e.g., heteroorganic or organometallic compounds.

Test compounds can be screened individually or in parallel. An example of parallel screening is a high throughput drug screen of large libraries of chemicals. Such libraries of candidate compounds can be generated or purchased, e.g., from Chembridge Corp. (San Diego, Calif.). Libraries can be designed to cover a diverse range of compounds. For example, a library can include 500, 1000, 10,000, 50,000, or 100,000 or more unique compounds. Alternatively, prior experimentation and anecdotal evidence can suggest a class or category of compounds of enhanced potential. A library can be designed and synthesized to cover such a class of chemicals.

The synthesis of combinatorial libraries is well known in the art and has been reviewed (see, e.g., Gordon et al, J. Med. Chem. (1994) 37:1385-1401; DeWitt and Czarnik, Acc. Chem. Res. (1996) 29:114; Armstrong et al., Acc. Chem. Res. (1996) 29:123; Ellman, Acc. Chem. Res. (1996) 29:132; Gordon et al., Acc. Chem. Res. (1996) 29:144; Lowe, Chem. Soc. Rev. (1995) 309, Blondelle et al., Trends Anal. Chem. (1995) 14:83; Chen et al, J. Am. Chem. Soc. (1994) 116:2661; U.S. Pat. Nos. 5,359,115, 5,362,899, and 5,288,514; PCT Publication Nos. WO92/10092, WO93/09668, WO91/07087, WO93/20242, WO94/08051).

Libraries of compounds can be prepared according to a variety of methods known in the art. For example, a "split-pool" strategy can be implemented in the following way: beads of a functionalized polymeric support are placed in a plurality of reaction vessels; a variety of polymeric supports suitable for solid-phase peptide synthesis are known, and some are commercially available (for examples, see, e.g., Bodansky "Principles of Peptide Synthesis", 2nd edition, Springer-Verlag, Berlin (1993)). To each aliquot of beads is added a solution of a different activated amino acid, and the reactions are allowed to proceed to yield a plurality of immobilized amino acids, one in each reaction vessel. The aliquots of derivatized beads are then washed, "pooled" (i.e., recombined), and the pool of beads is again divided, with each aliquot being placed in a separate reaction vessel. Another activated amino acid is then added to each aliquot of beads. The cycle of synthesis is repeated until a desired peptide length is obtained. The amino acid residues added at each synthesis cycle can be randomly selected; alternatively, amino acids can be selected to provide a "biased" library, e.g., a library in which certain portions of the inhibitor are selected non-randomly, e.g., to provide an inhibitor having known structural similarity or homology to a known peptide capable of interacting with an antibody, e.g., the an anti-idiotypic antibody antigen binding site. It will be appreciated that a wide variety of peptidic, peptidomimetic, or non-peptidic compounds can be readily generated in this way.

The "split-pool" strategy can result in a library of peptides, e.g., modulators, which can be used to prepare a library of test compounds of the invention. In another illustrative synthesis, a "diversomer library" is created by the method of DeWitt et al., (Proc. Natl. Acad. Sci. U.S.A. 90:6909-13 (1993)). Other synthesis methods, including the "tea-bag" technique of Houghten (see, e.g., Houghten et al., Nature 354:84-86 (1991)) can also be used to synthesize libraries of compounds according to the subject invention.

Libraries of compounds can be screened to determine whether any members of the library have a desired activity, and, if so, to identify the active species. Methods of screening combinatorial libraries have been described (see, e.g., Gordon et al., J. Med. Chem., supra). Soluble compound libraries can be screened by affinity chromatography with an appropriate receptor to isolate ligands for the receptor, followed by identification of the isolated ligands by conventional techniques (e.g., mass spectrometry, NMR, and the like). Immobilized compounds can be screened by contacting the compounds with a soluble receptor; preferably, the soluble receptor is conjugated to a label (e.g., fluorophores, calorimetric enzymes, radioisotopes, luminescent compounds, and the like) that can be detected to indicate ligand binding. Alternatively, immobilized compounds can be selectively released and allowed to diffuse through a membrane to interact with a receptor. Exemplary assays useful for screening libraries of test compounds are described herein.

Screening Methods

The invention provides methods for identifying compounds capable of binding to and/or modulating the activity of EspF$_U$. Although applicants do not intend to be bound by any particular theory as to the biological mechanism involved, such compounds are thought to modulate (1) the function of an EspF$_U$ polypeptide (e.g., the ability of EspF$_U$ polypeptide to interact (e.g., bind to) Toca-1, Pak1, and/or N-WASP) and/or (2) expression of the EspF$_U$ polypeptide. Such compounds can reduce, disrupt, and/or inhibit pedestal formation, infection, and/or colonization by an enteric organism.

Screening for such compounds can be accomplished by identifying from a group of test compounds those that bind to an EspF$_U$ polypeptide, modulate an interaction between EspF$_U$ and N-WASP, modulate an interaction between EspF$_U$ and Toca-1, modulate an interaction between EspF$_U$ and Pak1, and/or modulate (i.e., increase or decrease) transcription and/or translation of EspF$_U$ nucleic acids. Test compounds can also be tested for their ability to modulate EspF$_U$ activity in vitro or in vivo.

Test compounds that bind to EspF$_U$ are candidate compounds. Candidate or test compounds that modulate an interaction between EspF$_U$ and N-WASP, modulate an interaction between EspF$_U$ and Toca-1, modulate an interaction between EspF$_U$ and Pak1, or modulate transcription and/or translation of EspF$_U$, are referred to herein as "EspF$_U$ modulating agents." Test compounds or candidate compounds that are screened and found capable of (a) modulating in vitro or in vivo the activity of an EspF$_U$ polypeptide or (b) modulating intestinal colonization, AE lesion formation, or pedestal formation by an enteric organism are considered "potential therapeutic agents." In the screening methods of the present invention, candidate compounds can be, but do not necessarily have to be, further tested to determine whether they are EspF$_U$ modulating agents or potential therapeutic agents.

There are currently no established treatments for infections with EHEC, nor is there any evidence indicating that antibiotics improve the course of disease. In fact treatment with some antibiotics enhances the production of Shiga-like toxin (Stx) and may promote kidney complications. The screens described below can be used to screen for candidate compounds or EspF$_U$ modulating agents that can be used in pharmaceutical treatments for the treatment of EHEC infection without enhancing the detrimental production of Stx.

1. EspF$_U$ Candidate Compounds

In one aspect, the invention includes methods for screening test compounds to identify compounds that bind to EspF$_U$ polypeptides. Binding of a test compound to an EspF$_U$ polypeptide can be detected, for example, in vitro by reversibly or irreversibly immobilizing the test compound(s) on a substrate, e.g., the surface of a well of a 96-well polystyrene microtiter plate. Methods for immobilizing polypeptides and other small molecules are well known in the art. For example, microtiter plates can be coated with an EspF$_U$ polypeptide by adding the polypeptide in a solution (typically, at a concentration of 0.05 to 1 mg/ml in a volume of 1-100 µl water or buffer) to each well, and incubating the plates at room temperature to 37° C. for a given amount of time, e.g., for 0.1 to 36 hours. Polypeptides not bound to the plate can be removed, e.g., by pouring excess solution from the plate, and then washing the plate (once or repeatedly) with water or a buffer. The plate can then be washed with a buffer that lacks the bound polypeptide. To block the free protein-binding sites on the plates, plates can be blocked with a protein that is unrelated to the bound polypeptide. For example, 300 µl of bovine serum albumin (BSA) at a concentration of 2 mg/ml in Tris-HCl can be used. Suitable substrates include those substrates that contain a defined cross-linking chemistry (e.g., plastic substrates, such as polystyrene, styrene, or polypropylene substrates from Corning Costar Corp. (Cambridge, Mass.), for example). If desired, a beaded particle, e.g., beaded agarose or beaded Sepharose®, can be used as the substrate. Test compounds can then be added to the coated plate and allowed to bind to the EspF$_U$ polypeptide (e.g., at 37° C. for 0.5-12 hours). The plate can then be washed as described above.

Binding of EspF$_U$ to a second compound, e.g., the test compound described above, can be detected by any of a variety of art-known methods. For example, an antibody that specifically binds to an EspF$_U$ polypeptide (i.e., an anti-EspF$_U$ antibody) can be used in an immunoassay. If desired, the antibody can be labeled (e.g., fluorescently or with a radioisotope) and detected directly (see, e.g., West and McMahon, J. Cell Biol. 74:264, (1977)). Alternatively, a second antibody can be used for detection (e.g., a labeled antibody that binds to the Fc portion of the anti-EspF$_U$ antibody). In an alternative detection method, the EspF$_U$ polypeptide is labeled (e.g., with a radioisotope, fluorophore, chromophore, or the like), and the label is detected. In still another method, an EspF$_U$ polypeptide is produced as a fusion protein with a protein that can be detected optically, e.g., green fluorescent protein (which can be detected under UV light). In an alternative method, the polypeptide is produced as a fusion protein with an enzyme having a detectable enzymatic activity, such as horseradish peroxidase, alkaline phosphatase, β-galactosidase, or glucose oxidase. Genes encoding all of these enzymes have been cloned and are available for use by skilled practitioners. If desired, the fusion protein can include an antigen, which can be detected and measured with a polyclonal or monoclonal antibody using conventional methods. Suitable antigens include enzymes (e.g., horse radish peroxidase, alkaline phosphatase, and β-galactosidase) and non-enzymatic polypeptides (e.g., serum proteins, such as BSA and globulins, and milk proteins, such as caseins).

In various methods for identifying polypeptides, e.g., test polypeptides, that bind to an EspF$_U$ polypeptide, the conventional two-hybrid assays of protein/protein interactions can be used (see e.g., Chien et al., Proc. Natl. Acad. Sci. USA, 88:9578, (1991); Fields et al., U.S. Pat. No. 5,283,173; Fields and Song, Nature, 340:245, (1989); Le Douarin et al., Nucleic Acids Research, 23:876, (1995); Vidal et al., Proc. Natl. Acad. Sci. USA, 93:10315-10320, (1996); and White, Proc. Natl. Acad. Sci. USA, 93:10001-10003, (1996)). Typically, two-hybrid methods involve reconstitution of two separable domains of a transcription factor. One fusion protein contains the EspF$_U$ polypeptide fused to either a transactivator domain or DNA binding domain of a transcription factor (e.g., of Gal4). The other fusion protein contains a test polypeptide fused to either the DNA binding domain or a transactivator domain of a transcription factor. Once brought together in a single cell (e.g., a yeast cell or mammalian cell), one of the fusion proteins contains the transactivator domain and the other fusion protein contains the DNA binding domain. Therefore, binding of the EspF$_U$ polypeptide to the test polypeptide reconstitutes the transcription factor. Reconstitution of the transcription factor can be detected by detecting expression of a gene (i.e., a reporter gene) that is operably linked to a DNA sequence that is bound by the DNA binding domain of the transcription factor. Kits for practicing various two-hybrid methods are commercially available (e.g., from Clontech; Palo Alto, Calif.).

In another aspect, the invention includes methods for screening test compounds to identify a compound that modulates a protein-protein interaction between an EspF$_U$ polypeptide and another polypeptide, e.g., an N-WASP polypeptide, a Toca-1 polypeptide, or a Pak1 polypeptide. A method useful for high throughput screening of compounds capable of modulating protein-protein interactions between transcriptional regulators is described in Lepourcelet et al., *Cancer Cell* 5: 91-102 (2004), which is incorporated herein by reference in its entirety. Typically, a first compound is provided. The first compound is an EspF$_U$ polypeptide or biologically active fragment thereof, or the first compound is either a Toca-1, Pak1, or N-WASP polypeptide, or biologically active fragment thereof. A second compound is provided which is different from the first compound and which is labeled. The second compound is an EspF$_U$ polypeptide or biologically active fragment thereof, or the second compound is a Toca-1, Pak1, or N-WASP polypeptide, or biologically active fragment thereof. A test compound is provided. The first compound, second compound, and test compound are contacted with each other. The amount of label bound to the first compound is then determined. A change in protein-protein interaction between the first compound and the second compound as assessed by label bound is indicative of the usefulness of the compound in modulating a protein-protein interaction between EspF$_U$ and the N-WASP polypeptide. In some embodiments, the change is assessed relative to the same reaction without addition of the test compound.

In certain embodiments, the first compound provided is attached to a solid support. Solid supports include, e.g., resins, e.g., agarose, beads, and multiwell plates. In certain embodiments, the method includes a washing step after the contacting step, so as to separate bound and unbound label.

In certain embodiments, a plurality of test compounds is contacted with the first compound and second compound. The different test compounds can be contacted with the other compounds in groups or separately. In certain embodiments, each of the test compounds is contacted with both the first compound and the second compound in separate wells. For example, the method can screen libraries of test compounds. Libraries of test compounds are discussed in detail above. Libraries can include, e.g., natural products, organic chemicals, peptides, and/or modified peptides, including, e.g., D-amino acids, unconventional amino acids, and N-substituted amino acids. Typically, the libraries are in a form compatible with screening in multiwell plates, e.g., 96-well plates. The assay is particularly useful for automated execution in a multiwell format in which many of the steps are controlled by computer and carried out by robotic equipment. The libraries can also be used in other formats, e.g., synthetic chemical libraries affixed to a solid support and available for release into microdroplets.

In certain embodiments, the first compound is an EspF$_U$ polypeptide, or fragment thereof, and the second compound is a Toca-1, Pak1, or N-WASP polypeptide, or a fragment thereof. In other embodiments, the first compound is EspF$_U$ polypeptide, or a fragment thereof, and the second compound is a Toca-1, Pak1, or N-WASP polypeptide, or a fragment thereof. The solid support to which the first compound is attached can be, e.g., sepharose beads, SPA beads (microspheres that incorporate a scintillant) or a multiwell plate. SPA beads can be used when the assay is performed without a washing step, e.g., in a scintillation proximity assay. Sepharose beads can be used when the assay is performed with a washing step. The second compound can be labeled with any label that will allow its detection, e.g., a radiolabel, a fluorescent agent, biotin, a peptide tag, or an enzyme fragment. The second compound can also be radiolabeled, e.g., with $^{125}$I or $^3$H.

In certain embodiments, the enzymatic activity of an enzyme chemically conjugated to, or expressed as a fusion protein with, the first or second compound, is used to detect bound protein. A binding assay in which a standard immunological method is used to detect bound protein is also included. In certain other embodiments, the interaction of an EspF$_U$ polypeptide, or fragment thereof, and a Toca-1, Pak1, or N-WASP polypeptide, or fragment thereof, is detected by fluorescence resonance energy transfer (FRET) between a donor fluorophore covalently linked to EspF$_U$ (e.g., a fluorescent group chemically conjugated to EspF$_U$, or a variant of green fluorescent protein (GFP) expressed as an EspF$_U$-GFP chimeric protein) and an acceptor fluorophore covalently linked to a Toca-1, Pak1, or N-WASP polypeptide, or fragment thereof, where there is suitable overlap of the donor emission spectrum and the acceptor excitation spectrum to give efficient nonradiative energy transfer when the fluorophores are brought into close proximity through the protein-protein interaction of a EspF$_U$ polypeptide and a Toca-1, Pak1, or N-WASP polypeptide.

In other embodiments, the protein-protein interaction is detected by reconstituting domains of an enzyme, e.g., β-galactosidase (see Rossi et al., Proc. Natl. Acad. Sci. USA 94:8405-8410 (1997)).

In still other embodiments, the protein-protein interaction is assessed by fluorescence ratio imaging (Bacskai et al., Science 260:222-226 (1993)) of suitable chimeric constructs of EspF$_U$ polypeptides and Tir or N-WASP polypeptides in cells, or by variants of the two-hybrid assay (Fearon et al., Proc. Natl. Acad. Sci. USA 89:7958-7962 (1992); Takacs et al., Proc. Natl. Acad. Sci. USA 90:10375-10379 (1993); Vidal et al., Proc. Natl. Acad. Sci. USA 93:10315-10320 (1996); Vidal et al., Proc. Natl. Acad. Sci. USA 93:10321-10326 (1996)) employing suitable constructs of EspF$_U$ and Toca-1, Pak1, or N-WASP polypeptides and tailored for a high throughput assay to detect compounds that inhibit the EspF$_U$/N-WASP interaction, EspF$_U$/Toca-1 interaction, or EspF$_U$/Pak1 interaction. These embodiments have the advantage that the cell permeability of compounds that act as modulators in the assay is assured.

For example, in one assay, but not the only assay, EspF$_U$ polypeptides or fragment thereof, are adsorbed to ELISA plates. EspF$_U$ polypeptides are then exposed to test compounds, followed by glutathione-S-transferase (GST)-N-WASP polypeptide fusion proteins, GST-Toca-1 polypeptide fusion proteins, or GST-Pak1 polypeptide fusion proteins. Bound protein is detected with goat anti-GST antibody, alkaline phosphatase (AP)-coupled anti-goat IgG, and AP substrate. Compounds that interfere with protein-protein interactions yield reduced AP signals in the ELISA plates.

2. EspF$_U$ Modulating Agents

In still another aspect, the invention provides methods of identifying test compounds that modulate (e.g., increase or decrease) expression of an EspF$_U$ polypeptide. The methods include contacting an EspF$_U$ nucleic acid with a test compound and then measuring expression of the encoded EspF$_U$ polypeptide. In a related aspect, the invention features methods of identifying compounds that modulate (e.g., increase or decrease) the expression of EspF$_U$ polypeptides by measuring expression of an EspF$_U$ polypeptide in the presence of the test compound or after the addition of the test compound in: (a) a cell line into which has been incorporated a recombinant construct including the EspF$_U$ nucleic acid sequence or fragment or an allelic variation thereof, or (b) a cell population or cell line that naturally selectively expresses EspF$_U$, and then measuring the activity of EspF$_U$ and/or the expression thereof. EspF$_U$ gene expression can be monitored using techniques (e.g., Northern blotting, RT-PCR, Western blotting, immunoassays and the like) and probes known to those skilled in the art or disclosed herein. Standard quantitative assays of gene expression and EspF$_U$ activity can be used.

Since the $EspF_U$ nucleic acids described herein have been identified, they can be cloned into various host cells, e.g., fungi (e.g., yeast), or bacteria, (e.g., *E. coli*), for carrying out such assays in whole cells.

In certain embodiments, an isolated nucleic acid molecule encoding an $EspF_U$ polypeptide is used to identify a compound that modulates (e.g., increases or decreases) the expression of $EspF_U$ in vivo (e.g., in an $EspF_U$-producing cell). In such embodiments, cells that express $EspF_U$ are cultured, exposed to a test compound (or a mixture of test compounds), and the level of $EspF_U$ expression or activity is compared with the level of $EspF_U$ expression or activity in cells that are otherwise identical but that have not been exposed to the test compound(s). Expression of an $EspF_U$ polypeptide can be measured using art-known methods, for example, by Northern blot PCR analysis or RNAse protection analyses using a nucleic acid molecule of the invention as a probe. Other examples include enzyme-linked immunosorbent assay (ELISA), radioimmunoassay (RIA) and fluorescent activated cell sorting (FACS). The level of expression in the presence of the test molecule, compared with the level of expression in its absence, will indicate whether or not the test compound modulates the expression of $EspF_U$.

In still another aspect, the invention provides methods of screening test compounds utilizing cell systems that are sensitive to perturbation to one or several transcriptional/translational components. In one embodiment, the cell system is a modified $EspF_U$-expressing cell in which one or more of the transcriptional/translational components of the cell are present in an altered form or in a different amount compared with a corresponding wild-type $EspF_U$-expressing cell. This method involves examining a test compound for its ability to perturb transcription/translation in such a modified cell.

In certain embodiments, the methods include identifying candidate compounds that interfere with steps in $EspF_U$ translational accuracy, such as maintaining a proper reading frame during translation and terminating translation at a stop codon. This method involves constructing cells in which a detectable reporter polypeptide can only be produced if the normal process of staying in one reading frame or of terminating translation at a stop codon has been disrupted. This method further involves contacting the cell with a test compound to examine whether it increases or decreases the production of the reporter polypeptide.

In other embodiments, the cell system is a cell-free extract and the method involves measuring transcription or translation in vitro. Conditions are selected so that transcription or translation of the reporter is increased or decreased by the addition of a transcription modifier or a translation modifier to the cell extract.

One method for identifying candidate compounds relies upon a transcription-responsive gene product. This method involves constructing a cell in which the production of a reporter molecule changes (i.e., increases or decreases) under conditions in which cell transcription of an $EspF_U$ nucleic acid changes (i.e., increases or decreases). Specifically, the reporter molecule is encoded by a nucleic acid transcriptionally linked to a sequence constructed and arranged to cause a relative change in the production of the reporter molecule when transcription of an $EspF_U$ nucleic acid changes. A gene sequence encoding the reporter may, for example, be fused to part or all of the gene encoding the transcription-responsive gene product and/or to part or all of the genetic elements that control the production of the gene product. Alternatively, the transcription-responsive gene product may stimulate transcription of the gene encoding the reporter, either directly or indirectly. The method further involves contacting the cell with a test compound, and determining whether the test compound increases or decreases the production of the reporter molecule in the cell.

Alternatively, the methods for identifying candidate compounds can rely upon a translation-responsive gene product. These methods involve constructing a cell in which cell translation of an $EspF_U$ nucleic acid changes (i.e., increases or decreases). Specifically, the reporter molecule is encoded by a nucleic acid either translationally linked or transcriptionally linked to a sequence constructed and arranged to cause a relative increase or decrease in the production of the reporter molecule when transcription of an $EspF_U$ nucleic acid changes. A gene sequence encoding the reporter may, for example, be fused to part or all of the gene encoding the translation-responsive gene product and/or to part or all of the genetic elements that control the production of the gene product. Alternatively, the translation-responsive gene product may stimulate translation of the gene encoding the reporter, either directly or indirectly. The method further involves contacting the cell with a test compound, and determining whether the test compound increases or decreases the production of the first reporter molecule in the cell.

For any method described herein, a wide variety of reporters may be used, with typical reporters providing conveniently detectable signals (e.g., by spectroscopy). By way of example, a reporter gene may encode an enzyme that catalyzes a reaction that produces a colored compound.

Examples of reporter molecules include but are not limited to β-galactosidase, invertase, green fluorescent protein, luciferase, chloramphenicol acetyltransferase, beta-glucuronidase, exo-glucanase and glucoamylase. Alternatively, radiolabeled or fluorescent tag-labeled nucleotides can be incorporated into nascent transcripts that are then identified when bound to oligonucleotide probes. For example, the production of the reporter molecule can be measured by the enzymatic activity of the reporter gene product, such as β-galactosidase.

Any of the methods described herein can be used for high throughput screening of numerous test compounds to identify candidate compounds. By high-throughput screening is meant that the method can be used to screen a large number of candidate compounds relatively quickly in an automated or non-automated fashion.

Test compounds can be tested directly, i.e. without first determining that they are candidate compounds, in any of the screens described herein that identify $EspF_U$ modulating agents or potential therapeutic agents. Alternatively, having identified a test compound as a candidate compound, the candidate compound can be further tested to confirm whether it is an $EspF_U$ modulating agent or potential therapeutic agent, i.e., to determine whether it can modulate $EspF_U$ activity, e.g., actin pedestal formation in cell culture, actin structure formation in vitro, or colonization of host intestine in vivo (e.g., using an animal, e.g., rodent, rabbit, cow, or pig), if desired.

Exemplary assays for monitoring infection and pedestal formation in HeLa cells are described in the Examples section, below. Typically, cell culture methods of identifying an $EspF_U$ modulating agent employ cell cultures, e.g., HeLa cells, mouse embryonic fibroblasts, or other cultured host cells, that can be infected by an enteric organism.

Typically, bacterial attachment/pedestal formation assays are performed as follows: host cells are grown in a monolayer, infected with an enteric organism and, in the presence or absence of a test or candidate compound visualized, e.g. using fluorescence microscopy, to monitor any one or more of the following: bacterial attachment, pedestal formation, or pedestal stability.

One exemplary cell culture assay can be carried out as follows: cells are grown to 50-90% confluency on glass cover slips in multiwell plates; cells are then infected with media containing $10^5$-$10^6$ enteric bacteria in DMEM+3% FBS+25 mM HEPES for 3.5 hours, washed with PBS, and incubated for a further 1.5 hours in fresh medium prior to fixation. Infected monolayers are fixed, e.g., in PBS+2.5% paraformaldehyde for 20 minutes and permeabilized with 0.1% Triton®-X-100 as described in Campellone et al. (*Mol. Microbiol.* 43:1227-41 (2002)). Bacteria are detected by treatment with 1 mg/ml DAPI or by treatment with primary antibodies to bacteria that are visualized using secondary antibodies. F-actin pedestals can be identified by staining with Alexa Fluor® 568-phalloidin (1:150; Molecular Probes). A test compound or candidate compound is an $EspF_U$ modulating agent if it modulates, e.g., prevents, increases, decreases, or disrupts, any one or more of the following: bacterial attachment, pedestal formation, or pedestal stability over time.

In a typical in vitro assay, glutathione beads coated with recombinant glutathione S-transferase $EspF_U$ fusion proteins, e.g., GST-$EspF_U$, are tested for their ability to promote actin assembly in *Xenopus* cell-free extracts, with or without the addition of Tir peptide. A *Xenopus* cell free assay can be a variation of an assay previously described. See e.g., Desai et al., *Meth. Cell Biol.*, 61:385-412, (1999) and Peterson et al., *Proc. Natl. Acad. Sci. USA*, 98:10624-10629 (2001). Typically, dilute centrifuged cytostatic factor (CSF)-arrested *Xenopus* cell extracts are supplemented with an ATP containing energy mixture and labeled actin monomers, supplemented extracts are aliquoted into multi-well or microtiter plates, peptide components of the assay are added to the mixture, and the formation of actin structures is assayed. Peptide components include peptides comprising $EspF_U$, or fragments thereof. Peptide components can optionally include any one or more of the following: peptides comprising Tir, or fragments thereof, peptides comprising N-WASP, or fragments thereof (e.g., the verpolin, cofilin, acidic domain-containing (VCA) region of N-WASP), peptides including the SH3 domain of Toca-1, peptides comprising an N-terminal fragment of Pak1, peptides comprising cdc42 GTPase, or fragments thereof, and peptides comprising Arp2/3, or fragments thereof.

For example, a *Xenopus* cell-free assay can be performed using any one of the following: recombinant full length $EspF_U$, fusion (GST-$EspF_U$), recombinant C-terminal amino acids 80-384 of $EspF_U$ fusion (GST-$EspF_U$(C)), or the minimal $EspF_U$ derivative capable of binding to N-WASP. Any of these $EspF_U$ fusion are coated on glutathione beads and added to *Xenopus* extracts described above, e.g., containing pyrene or rhodamine labeled actin monomers (Cytoskeleton, Denver, Colo.). Optionally, N-WASP, Toca-1 peptides, Pak1 peptides, cdc-42 peptides, and/or Arp 2/3, or fragments thereof, can be added to the extract. Formation of rhodamine labeled actin structures is monitored by microscopy. Negative controls include point or deletion mutants of $EspF_U$ that are incapable of binding to N-WASP. Actin assembly in *Xenopus* egg extracts can be scored blindly to test for a strict correlation between N-WASP binding by $EspF_U$ and actin polymerization over a time course (e.g., measured once a minute for 15 to 60 minutes at room temperature). Positive controls include the addition of phosphatidylinositol bisphosphate ($PIP_2$) containing liposomes, as described in Peterson et al., supra.

In such assays, a test compound or candidate compound is considered an $EspF_U$ modulating agent if it modulates, e.g., prevents, increases, decreases, or disrupts the formation of actin structures in vitro, and/or the stability of such structures over time.

Another cell-free actin assembly assay uses only an ATP-containing buffer solution instead of *Xenopus* extracts as described in Peterson, et al, supra. In this assay, $EspF_U$ is included in a buffer mixture that contains Arp2/3 (e.g., 45-75 nM), VCA (e.g., 5.5 mg/ml), N-WASP (e.g., 240 nM), and GST-cdc42. (e.g., 80 nM). Actin (e.g., 2.4 mM final, 20% pyrene-labeled) is added last. The time course of actin polymerization can be measured as described above.

Alternatively, or additionally, in vivo testing of test compounds or candidate compounds can be performed by means known to those in the art. For example, test or candidate compound(s) can be administered in a pharmaceutical composition (see below) to a mammal, such as a pig, rabbit, cow, etc., that is infected with an enteric organism. Control compositions that do not include a candidate compound can be administered to different infected mammal, which serves as a negative control. Animals that are particularly useful for in vivo testing are gnotobiotic piglets (the best established model for EHEC infection) and rabbits. See e.g., Tzipori et al., *Infect Immun* 63:3621-7 (1995) and Ritchie et al., *Infect Immun* 71:7129-39 (2003). Control compounds that prevent infection or reduce the effects of infection with an enteric organism relative to a negative control are considered $EspF_U$ modulating agents In one in vivo assay, gnotobiotic piglets are infected with an enteric organism, e.g., an EHEC. Infected animals are administered either a candidate compound or a control composition, before, after, or during infection with the enteric organism. The formation of attaching and effacing (AE) lesions and/or colonization of intestines are subsequently monitored. AE lesions and intestinal colonization can be monitored indirectly, e.g., by monitoring gross epithelial damage, diarrhea, and/or weight loss. AE lesions can be monitored directly by formalin-fixing sections from the small intestine, cecum, and/or spiral colon of the piglet and scoring for structural integrity of the mucosa. Pedestal formation can be monitored by transmission electron microscopy or staining methods known in the art, e.g. Richardson staining.

In such assays, candidate compounds that prevent or reduce (relative to a control compound) the occurrence of one or more of diarrhea, weight loss, AE lesions, pedestal formation, and/or intestinal colonization by an enteric pathogen, e.g., EHEC, are considered $EspF_U$ modulating agents.

In another in vivo assay, rabbits are infected with an enteric organism, e.g., EHEC, that causes Nck-independent pedestal formation. Infected animals are administered a candidate compound or a negative control. Infected rabbits are then observed and compared to negative controls over time. Typically, after a relatively short period, e.g. two days, infected rabbits not given a candidate compound suffer severe diarrhea and classic AE lesions on their intestinal epithelium. After a longer period, e.g. seven days, the colon and ceca are distended, and histological analysis may reveal suppurative colitis.

Candidate compounds that prevent or reduce (relative to a negative control) the occurrence of one or more of diarrhea, weight loss, AE lesions, pedestal formation, and/or intestinal colonization by an enteric pathogen, are considered $EspF_U$ modulating agents.

Other in vivo animals can be used to determine if candidate compounds identified by the assays herein are $EspF_U$ modulating agents. Animals appropriate for use in an in vivo assay include cows, sheep, goats, monkeys, and other mammals. Bacterial colonization in any of the above in vivo animal screens can also assayed by counting bacteria present in stool and/or intestinal homogenates, e.g., on sorbitol MacConkey plates as described in Ritchie et al., supra.

Medicinal Chemistry

Once a candidate compound (or modulating agent) of interest has been identified, standard principles of medicinal chemistry can be used to produce derivatives of the compound. Derivatives can be screened for improved pharmacological properties, for example, efficacy, pharmaco-kinetics, stability, solubility, and clearance. The moieties responsible for a compound's activity in the assays described above can be delineated by examination of structure-activity relationships (SAR) as is commonly practiced in the art. A person of ordinary skill in pharmaceutical chemistry could modify moieties on a candidate compound or agent and measure the effects of the modification on the efficacy of the compound or agent to thereby produce derivatives with increased potency. For an example, see Nagarajan et al., *J. Antibiot.* 41:1430-8 (1988). Furthermore, if the biochemical target of the compound (or agent) is known or determined, the structure of the target and the compound can inform the design and optimization of derivatives. Molecular modeling software is commercially available (e.g., from Molecular Simulations, Inc.) for this purpose.

Pharmaceutical Compositions

The compounds and agents, e.g., small molecules, nucleic acids, polypeptides, and antibodies (all of which can be referred to herein as "active compounds"), can be incorporated into pharmaceutical compositions. Such compositions typically include the active compound and a pharmaceutically acceptable carrier. A "pharmaceutically acceptable carrier" can include solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, a polyol (for example, glycerol, propylene glycol, and liquid polyethylene glycol, and the like), or a suitable mixture thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be achieved by including an agent that delays absorption, e.g., aluminum monostearate or gelatin, in the composition.

Sterile injectable solutions can be prepared by incorporating the active compound in the required amount in an appropriate solvent with one or a combination of ingredients enumerated above, as required, followed by filtered sterilization. Typically, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions typically include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue, e.g., bone or cartilage, in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

For the compounds described herein, an effective amount, e.g., of a protein or polypeptide (i.e., an effective dosage), ranges from about 0.001 to 30 mg/kg body weight, e.g., about 0.01 to 25 mg/kg body weight, e.g., about 0.1 to 20 mg/kg body weight. The protein or polypeptide can be administered one time per week for between about 1 to 10 weeks, e.g., between 2 to 8 weeks, about 3 to 7 weeks, or for about 4, 5, or 6 weeks. The skilled artisan will appreciate that certain factors influence the dosage and timing required to effectively treat a patient, including but not limited to the type of patient to be treated, the severity of the disease or disorder, previous treatments, the general health and/or age of the patient, and other diseases present. Moreover, treatment of a patient with a therapeutically effective amount of a protein, polypeptide, antibody, or other compound can include a single treatment or, preferably, can include a series of treatments.

For antibodies, a useful dosage is 5 mg/kg of body weight (typically 3 mg/kg to 20 mg/kg). Typically, partially human antibodies and fully human antibodies have a longer half-life within the human body than other antibodies. Accordingly, lower dosages and less frequent administration are possible. Modifications such as lipidation can be used to stabilize antibodies or other therapeutic proteins and to enhance uptake and tissue penetration. A method for lipidation of antibodies is described by Cruikshank et al. (*J. Acquir. Immune Defic. Syndr. Hum. Retrovirol.* 14:193 (1997)). Alternatively, an antibody or a fragment thereof may be joined to a protein transduction domain, e.g., an HIV Tat-1 activator domain or the homeodomain of Antennapedia transcription factor (for review, see Heng and Cao (2005) Medical Hypotheses 64:1105-8). Fusion proteins thus generated have been found to transduce into the cells of tissues in a mouse model system (Schwarze et al. (1999) Science 285:1569-1572).

If the compound is a small molecule, exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Nucleic acid molecules (e.g., $EspF_U$-modulating DNA) of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen et al., *Proc. Natl. Acad. Sci. USA* 91:3054-3057 (1994)). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system. In one approach, recombinant vectors encoding single chain antibodies that specifically bind to $EspF_U$ may be introduced into cells via gene therapy technologies, wherein the encoded single chain anti-EspFU antibody is expressed intracellularly, binds to EspFU protein, and thereby inhibits its function. Methods for engineering such intracellular single chain antibodies, also known as "intrabodies" are known. This technology has been successfully applied in the art (for review, see Mundt, *Eur. Pharm. Contractor*, Winter 2001; Richardson and Marasco, 1995, *TIBTECH* vol. 13).

Alternately, nucleic acid molecules of the invention can be administered to EspFU-expressing bacteria. Nucleic acids such as ribozymes or antisense molecules can be provided by methods known in the art, e.g., using bacteriophage that infect *E. coli*. Bacteriophage and methods of engineering them to express heterologous nucleic acids are known in the art.

The pharmaceutical compositions can be included in a container, pack, or dispenser together with instructions for administration.

Model Systems

Because EPEC bacteria generate actin pedestals more rapidly and at a higher frequency than EHEC on cultured cells (Cantey and Moseley, *Infection and Immunity* 59:3924-3929 (1991); Deibel et al., *Mol. Microbiol.* 28:463-74 1998), and because EPEC is less hazardous to laboratory personnel (Donnenberg and Whittam, *J. Clin. Invest.* 107, 539-48 (2001)), EPEC has been preferentially used in studies to investigate the mechanisms of actin pedestal assembly. As described above, however, the molecular mechanisms of EPEC and EHEC mediated pedestal formation are somewhat different.

The identification herein of $EspF_U$ as an additional effector of EHEC mediated pedestal formation makes possible a number of different model systems to reconstitute EHEC mediated actin pedestal assembly. For example, an engineered EPEC strain that reconstitutes EHEC actin pedestal formation in a host cell is described in the examples below.

Typically, such EPEC strains express less than wild-type levels of EPEC Tir, e.g., no functional EPEC Tir, to prevent EPEC mediated pedestal formation. These strains are engineered to express functional full-length EHEC Tir, functional fragments of EHEC Tir, or allelic variants thereof. These strains are also engineered to express an $EspF_U$ polypeptide. As demonstrated in the Example section below, EPEC strains expressing EHEC Tir and $EspF_U$ together promote Nck-independent pedestal formation. Therefore, these EPEC strains can promote efficient Nck-independent mediated pedestal formation. Such strains are useful as model systems that, without exposure to dangerous EHEC strains, reconstitute EHEC pedestal formation, EHEC AE lesion formation, and/or EHEC colonization of host intestine.

In another model system an EPEC bacterial strain expresses lower than wild type levels of EPEC Tir and expresses either EHEC Tir or $EspF_U$. A host cell expresses either EHEC Tir or $EspF_U$, whichever is not expressed by the bacterial strain. The recombinant host cell and recombinant EPEC strain are allowed to contact each other. Upon translocation of the bacterial effector protein expressed by the EPEC strain into the host cell, Nck-independent pedestal formation is reconstituted, since the host cell comprises both necessary effectors for EHEC mediated pedestal formation.

In another model system, an EHEC host cell inducibly expresses EHEC Tir, $EspF_U$, or both, such that EHEC mediated pedestal formation can be inducibly reconstituted in the host cell. Induction of expression of one or more bacterial effectors in the host cell results in expression of EHEC Tir receptor in the host cell membrane and $EspF_U$ in the host cytoplasm, thereby promoting actin pedestal formation. In some cases, the induction of pedestal formation is promoted by presenting the cell with the Intimin ligand of Tir, e.g., attached to an EPEC bacterium.

The model systems described herein are useful for several purposes. They are useful as tools that reconstitute EHEC pedestal formation using bacterial strains that are not as dangerous to handle as EHEC. These strains can thus be used as models of the disease causing mechanism of EHEC strains, and the models provide tools for the identification of novel therapeutics directed to the treatment or prevention of EHEC bacterial infections. The model systems described herein can be used in the screening assays for identifying compounds that are $EspF_U$ modulating agents described above. Typically, any test compound or candidate compound that prevents or reduces actin pedestal formation by a model system described herein is an $EspF_U$ modulating agent.

For example, a model system can be used in the pedestal formation screening assays to identify compounds that inhibit pedestal formation. Host cells are infected with an EPEC strain expressing (a) EHEC Tir and $EspF_U$ and (b) no functional EPEC Tir. Host cells are contacted with either (i) a test compound or a candidate compound or (ii) a negative control composition. If the test compound or candidate compound prevents or reduces the formation of pedestal formation in the host cell, relative to pedestal formation in cells contacted with a control composition, then the test compound or candidate compound is an $EspF_U$ modulating agent.

In another example, an animal is infected with an EPEC strain that (a) expresses EHEC Tir and $EspF_U$ and (b) expresses no functional EPEC Tir. In this in vivo screen for an $EspF_U$ modulating agent, a pharmaceutical composition comprising a test compound or a candidate compound is administered to the animal, either before, during, or after infection. The compound is assessed for its ability to reduce or prevent any characteristic of a bacterial infection by the model system, e.g., diarrhea, weight loss, AE lesions, pedestal formation, and/or intestinal colonization (measured by bacterial titer in stool or in intestinal homogenates). A compound that prevents or reduces the characteristics of infection by the model system is considered an $EspF_U$ modulating agent.

Diagnostic Methods

The nucleic acids and polypeptides of the invention can be used in methods of diagnosing or detecting EHEC infections. There are currently no universally accepted treatments for infections with EHEC, nor is there unambiguous evidence indicating that antibiotics improve the course of disease. Treatment with some antibiotics enhances the production of Shiga-like toxin (Stx) and may promote kidney complications. By distinguishing an EHEC infection from infections by other bacterial species or other types of *E. coli* (e.g., EPEC), treatments for EHEC that do not enhance the production of Stx can be prescribed, such as supportive treatments, e.g., fluids, electrolytes, and paregorics.

The $espF_U$ gene sequence and the $EspF_U$ protein sequence are apparently unique and thus provide a potential means to detect EHEC. A sample, e.g., a stool sample, from a patient who is suspected to have an EHEC infection is provided. The presence of an $EspF_U$ nucleic acid or polypeptide is then detected in the sample.

$EspF_U$ nucleic acids can be detected by any method known in the art, e.g., Northern blot, Southern blot, PCT (e.g., real-time PCR), microarray analysis, or nucleic acid sequencing. Alternately, or in conjunction, $EspF_U$ polypeptides can be detected by any method known in the art, e.g., immunohistochemistry (e.g., Western blot, ELISA, radioimmunoassays), or mass spectrometry.

EXAMPLES

Starting Materials and Methods

Bacterial and mammalian cell culture: For routine passage, E. coli strains were cultured in LB at 37° C. Enterohemorrhagic E. coli (EHEC) mutants harboring the cat gene were grown in media containing 10-15 μg/ml chloramphenicol. For maintenance of EspF$_U$ expression plasmids, media were supplemented with 20 μg/ml tetracycline or 35 μg/ml kanamycin. Prior to infections, bacteria were cultured in Dulbecco's modified Eagle's medium (DMEM)+100 mM HEPES pH 7.4 in 5% $CO_2$ to enhance type III secretion. HeLa cells, Nck1/Nck2-deficient mouse embryonic fibroblasts (MEFs), and Nck1-rescued MEFs (Bladt et al., *Mol. Cell. Biol.* 23:4586-97 (2003)) were cultured in DMEM+10% Fetal Bovine Serum (FBS).

Mammalian cell infections: For microscopic analyses of EHEC infections, HeLa cells grown to 50-90% confluency on 12 mm glass coverslips were infected with 106 bacteria in DMEM+3% FBS+25 mM HEPES for 3.5 hours, washed with PBS, and incubated for a further 1.5 hours in fresh medium prior to fixation. Enteropathogenic E. coli (EPEC) infections of HeLa cells and MEFs were performed with 105 and 106 bacteria, respectively, for 3.5 hours. Greater numbers of EPEC were required for infection of MEFs due to inefficiencies of binding and effector translocation into these cell lines; EHEC strains interacted with MEFs at levels too low to allow strict quantitative analyses of actin pedestal formation. For biochemical analyses, HeLa cells grown to 75-90% confluency in 6-well plates were infected with $3\times10^7$ EHEC per well for 3.5 hours, washed, and incubated for a further 1.5 hours. In some experiments, non-intimately associated bacteria were killed with media containing 50 μg/ml gentamicin for 30 minutes. EPEC infections were performed with $10^7$ bacteria for 3.5 hours.

Immunofluorescence microscopy: Infected monolayers were fixed in phosphate buffered saline (PBS)+2.5% paraformaldehyde for 20 minutes and permeabilized with 0.1% Triton®-X 100 as described previously (Campellone et al., *Mol. Microbiol.* 43:1227-41 (2002)). Cells were treated with either mouse anti-myc mAb 9E10 (diluted 1:250 in PBS+1% BSA (Sigma, St. Louis, Mo.)), rabbit anti-TirN (1:750), rabbit anti-Nck (1:150; Upstate, Charlottesville, Va.), mouse anti-hemagglutinin (HA) mAb HA.11 (1:500; (Covance, Princeton, N.J.)), rabbit anti-N-WASP (1:1000), or rabbit anti-Arp3 (1:150) prior to treatment with secondary antibodies conjugated to Alexa™ 488 (1:150; Molecular Probes, Eugene, Oreg.). Bacteria were detected by treatment with 1 μg/ml DAPI, and F-actin was identified by staining with Alexa™ 568-phalloidin (1:150; Molecular Probes). For co-labeling of N-WASP with either Tir or EspF$_U$, cells were simultaneously treated with anti-N-WASP and either HA.11 or 9E10, followed by Alexa™ 488-anti-mouse and Alexa™ 568-anti-rabbit. For co-labeling of EspF$_U$ and Tir, cells were successively treated with 9E10, Alexa488-anti-mouse, biotinylated HA.11 (1:250), and Alexa™ 568-streptavidin. Pedestal formation efficiency was quantitated either by counting the percentage of cell-associated bacteria or the percentage of sites of translocated Tir that were associated with intense F-actin staining. Fifty randomly-chosen cells harboring 5-15 bacteria per cell were examined for each strain in three separate experiments. A range of 420-530 bacteria were counted per 50 cells.

Example 1

A Red-Assisted-Pathogenicity-Island-Deletion (RAPID) Screen Reveals a Second Chromosomal Locus Critical for Actin Pedestal Formation by EHEC To identify novel enterohemorrhagic E. coli (EHEC) genes required for actin pedestal formation, we utilized the λ-Red chromosome engineering technique, used extensively in K-12 strains of E. coli (reviewed in Court et al., *Annu. Rev. Genet.* 36:361-88 (2002)), to generate precise deletions throughout the O157:H7 genome. All EHEC strains used in this study were derived from TUV93-0, a Shiga-toxin-deficient form of EDL933 (Campellone et al., *Mol. Microbiol.* 43:1227-41 (2002)). Gene replacements were performed by electroporating PCR-generated recombination substrates containing the cat gene flanked by 50 nucleotides of island-targeting sequences into TUV93-0 harboring λ-Red plasmid pKM201 as previously described (Murphy and Campellone, *BMC Mol. Biol.* 4:11 (2003)). Proper replacement of EHEC open reading frames (ORFs) with cat was confirmed by the generation of specific PCR products using primers flanking the targeted region of the chromosome and by the absence of products after PCR using primers within the targeted region. No recombinants were generated in three attempts to delete O-islands #28, #57, and #173-175.

EHECΔespF (KC40) (Murphy and Campellone, *BMC Mol. Biol.* 4:11 (2003)) contains a cat replacement of codons 18-232, EHECΔespF$_M$ (KC42) contains a replacement encompassing the entire ORF, and EHECΔespF$_U$ (KC44) contains a replacement of codons 18-368. EHECΔtir (KC5), EHECΔETTA1 (KC30), and EPEC KC12 have been described (Campellone et al., *Mol. Microbiol.* 43:1227-41 (2002); Murphy and Campellone (2003) supra). No strains appeared to have any obvious growth defects.

Nineteen EHEC-specific islands ranging from 5-45 kb in size were targeted for complete or partial removal. These large islands contained either ORFs with annotations suggestive of roles in pathogenesis (Perna et al., *Infect Immun.* 66, 3810-7. (2001)) or prophage-like elements, which are known to encode virulence-associated proteins in many pathogens, including EHEC (Wagner and Waldor, *Infect. Immun.* 70:3985-93 (2002)). The islands targeted for deletion comprised 0.33 Mb of sequence encompassing 350 EHEC-specific open reading frames, 335 of which were outside of the locus of enterocyte effacement (LEE).

To determine which of the mutated EHEC strains generated in this RAPID screen retained the ability to generate actin pedestals, HeLa cells were infected with these bacteria, stained for F-actin, and examined microscopically. As previously reported (DeVinney et al., *Infect. Immun.* 67:2389-98 (1999)), strains lacking either the LEE-encoded EHEC type three apparatus (ETTA1) or the Tir effector were incapable of forming actin pedestals on cultured cells. In contrast, all but one of the strains containing deletions of the non-LEE islands generated actin pedestals at efficiencies similar to wild type EHEC. Only the mutant lacking O-Island #79, which harbors a cryptic prophage designated CP-933U (CP$_U$), was apparently defective at stimulating actin assembly.

CP$_U$ contains 46 open reading frames (Perna et al., (2001), supra); one of which, ORF Z3072, is predicted to encode a 384-amino acid protein that is 35% similar to EspF, a translocated effector encoded within the LEE elements of both EHEC and EPEC (McNamara et al., *J. Clin. Invest.* 107: 621-9 (2001)). Since this ORF resides within cryptic prophage U, we termed this putative gene espF$_U$.

Example 2

EHEC espF$_U$ is Required for Efficient Actin Pedestal Formation

To test whether the inability of EHECΔCP$_U$ to form pedestals was due to the absence of espF$_U$, this strain was transformed with plasmid containing espF$_U$ and monitored for the ability of transformants to generate actin pedestals during infection of mammalian cells. The plasmid used in this study, pEspFU (pKC321) contains the sequence from 425 bp upstream through 125 bp downstream of the espF$_U$ORF, which was PCR amplified from EDL933 genomic DNA using primers: 5'-ATAAGAATGCGGCCGCAAGTATATC-CCGATACATCATGCTCTC-3' (SEQ ID NO:17) and 5'-ATAAGAATGCGGCCGCGCTTCACAAAAC-CGGAGTCCG-3' (SEQ ID NO: 18). PCR product comprising the espF$_U$ORF was cloned into the NotI site of pKC272, a tet$^R$ derivative of the medium-copy-number plasmid pTP809 (Murphy et al., *Gene* 246:321-330 (2000)).

While approximately 65% of wild type EHEC bacteria that bound to HeLa cells generated actin pedestals, less than 5% of cell-associated EHECΔCP$_U$ harboring a vector control generated F-actin structures resembling actin pedestals (FIG. 1A). These residual sites of actin assembly generally stained less intensely than wild type pedestals (data not shown). In contrast, pEspFU supplied EspF$_U$ completely restored the pedestal-forming ability of EHECΔCP$_U$ to wild type levels (FIG. 1A). Thus, the only gene located within CP$_U$ that appears to be required for actin pedestal formation by EHEC is the espF-homologue, espF$_U$.

Example 3

EHEC espF and espF$_m$ are Not Required for Efficient Actin Pedestal Formation

The EspF protein encoded by the enteropathogenic *E. coli* (EPEC) LEE is a proline-rich effector that disrupts intestinal barrier function and induces cell death, but does not contribute to actin pedestal formation (Crane et al., *Cell Microbiol* 3:197-211 (2001); McNamara et al., *J. Clin. Invest.* 107: 621-9 (2001)). However, a role in pedestal formation has not been explored for the version of EspF encoded by the EHEC LEE. Moreover, in addition to espF and espF$_U$, EHEC possesses an ORF within another cryptic prophage, CP-933M, that potentially encodes a third proline-rich EspF-like protein, EspF$_M$ (Pema et al., (2001), supra). This hypothetical protein is virtually identical to the C-terminal 250 amino acids of EspF$_U$, but appears to lack an efficient initiation codon and an N-terminal sequence found in EspF$_U$ that is likely required for type III secretion. To determine which of these EspF-like genes are involved in actin pedestal formation, EHEC strains that contained specific deletions in espF, espF$_M$, or espF$_U$ were generated and examined for the ability to trigger localized actin assembly. Although deletions of espF and espF$_M$ did not affect actin pedestal formation by EHEC, the loss of espF$_U$ resulted in a dramatic reduction in the efficiency of pedestal formation and in the intensity of the residual pedestals that were formed, similar to a strain lacking CP$_U$ (FIG. 1B). Hence, espF$_U$ is unique among the espF-like genes in its ability to contribute to actin pedestal formation.

Example 4

EspF$_U$ Localizes to Sites of Actin Nucleation Following Translocation by the LEE-Encoded Type III Secretion System

To test whether espF$_U$ encodes a protein substrate for the LEE-encoded type III apparatus, pEspF$_U$-myc, a low-copy number plasmid that expresses a derivative of EspF$_U$ fused at its C-terminus to five copies of the c-myc epitope, was constructed in two steps.

In the first step, p-myc (pKC469) engineered a sequence encoding five c-myc repeats between sequences from 450 bp upstream of espF$_U$ and 530 bp downstream of espF$_U$. Sequence 450 bp upstream of espF$_U$ was PCR amplified using primers: 5'-CTCTCTTCTAGATAAAGGAGCAAAAG-TATA-3' (SEQ ID NO:19) and 5'-ATAAGAATGCGGC-CGCCATATGGATTACCTTATAAG-TAATTTTAGTTCTCC-3' (SEQ ID NO:20). Sequence 530 bp downstream of espF$_U$ was PCR amplified using primers: 5'-ATCATCCTGCAGTGATTATAATATAAT-TACCTATATTAGCTCTG-3' (SEQ ID NO:21) and 5'-AT-CATCGAGCTCCTTGCCCCCAAAGATACCACA-3' (SEQ ID NO:22). Fragment encoding five copies of c-myc epitope was amplified from pCS2+MT (a gift from S. Rankin, Harvard Medical School) with primers: 5'-ATAAGAAT-GCGGCCGCGGATCCCATCGATTTAAAGCTATG-3' (SEQ ID NO:23) and 5'-CTAGTCTAGACTGCAGTTAG-GTGAGGTCGCCCAAGCTCTC-3' (SEQ ID NO:24). PCR products containing the 450 bp upstream sequence, the 530 bp downstream sequence, and c-myc epitope repeat sequence, were cloned by four-way ligation into the XbaI and SacI sites of the low-copy-number kanR vector pK187 (Campellone et al., (2002), supra), creating c-myc fragment disruption between EHEC flanking sequences.

In the second step, espF$_U$ was amplified using primers

```
                                                  (SEQ ID NO:25)
5'-CCGGAATTCCATATGATTAACAATGTTTCTTCACTTTTTCC-3'
and (SEQ ID NO:26)
5'-CGCGGATCCCGAGCGCTTAGATGTATTAATGCC-3',
and
``` espF$_U$ was cloned into the NdeI and BamHI sites upstream of myc within p-myc, creating pEspFU-myc.

Plasmid pEspFU-myc was introduced into wild type EHEC and EHECΔETTA1, a strain that lacks a functional LEE type III secretion pathway. Since EHEC effectors that are transported by ETTA1 can be detected in liquid media (DeVinney et al., (1999), supra), cultures of these two EHEC strains were separated into a pelleted bacterial fraction and a supernatant fraction and examined in western blots for the presence of myc-tagged EspF$_U$. Treatment of blotted bacterial samples with an anti-myc antibody indicated that EspF$_U$-myc was expressed equivalently in both strains as a 52 kDa protein (FIG. 2, lanes 1-2), a size that is consistent with the expected combined molecular weights of EspF$_U$ (42 kDa) and the myc-tag (10 kDa). However, as predicted for a substrate of ETTA1, EspF$_U$-myc was only detectable in the culture supernatant of the wild type strain (FIG. 2, compare lanes 5,6).

To test whether the LEE-derived secretory pathway also promoted entry of EspF$_U$-myc into mammalian cells, HeLa cells were infected with these same EHEC strains and examined microscopically for the myc-tag. While EspF$_U$-myc was clearly visible within host cells beneath translocation-proficient EHEC, it was not detected in cells harboring translocation-deficient EHEC, indicating that $EspF_U$ is indeed translocated and requires the LEE-encoded type III machinery in order to enter host cells.

These studies of the expression, secretion, and translocation of myc-tagged $EspF_U$ were each performed in strain backgrounds in which the untagged version of this protein was presumably also present. To examine the same properties of epitope-tagged $EspF_U$ in the absence of endogenous $EspF_U$, $pEspF_U$-myc was introduced into EHECΔ$espF_U$. As expected, this strain expressed, secreted, and translocated myc-tagged $EspF_U$ (FIG. 2, lanes 4,8). $EspF_U$-myc also completely restored actin pedestal-forming ability to this strain (70.9±2.9 pedestals/100 bacteria compared to 2.6±1.5 pedestals/100 bacteria for the mutant), demonstrating that the epitope-tagged derivative of $EspF_U$ is fully functional. Consistent with a role for $EspF_U$ as an effector of pedestal formation, co-staining for $EspF_U$-myc and F-actin demonstrated that $EspF_U$ primarily localized to tips of actin pedestals.

Example 5

$EspF_U$ Does Not Modulate the Expression, Modification, or Membrane Localization of Tir Tir, the only effector previously shown to be directly required for EHEC pedestal formation, is also known to localize within host cells at the tips of actin pedestals (DeVinney et al., (1999), supra). One possible explanation for the inability of EHECΔespFU to effectively form pedestals is that Tir is not efficiently transported through the type III secretory apparatus without $EspF_U$. However, examination of fractionated EHEC cultures demonstrated that the expression and secretion of Tir were equivalent in the presence or absence of $EspF_U$ (FIG. 2, lanes 3-4, 7-8), indicating that $EspF_U$ does not act as a Tir chaperone.

Figure 3:
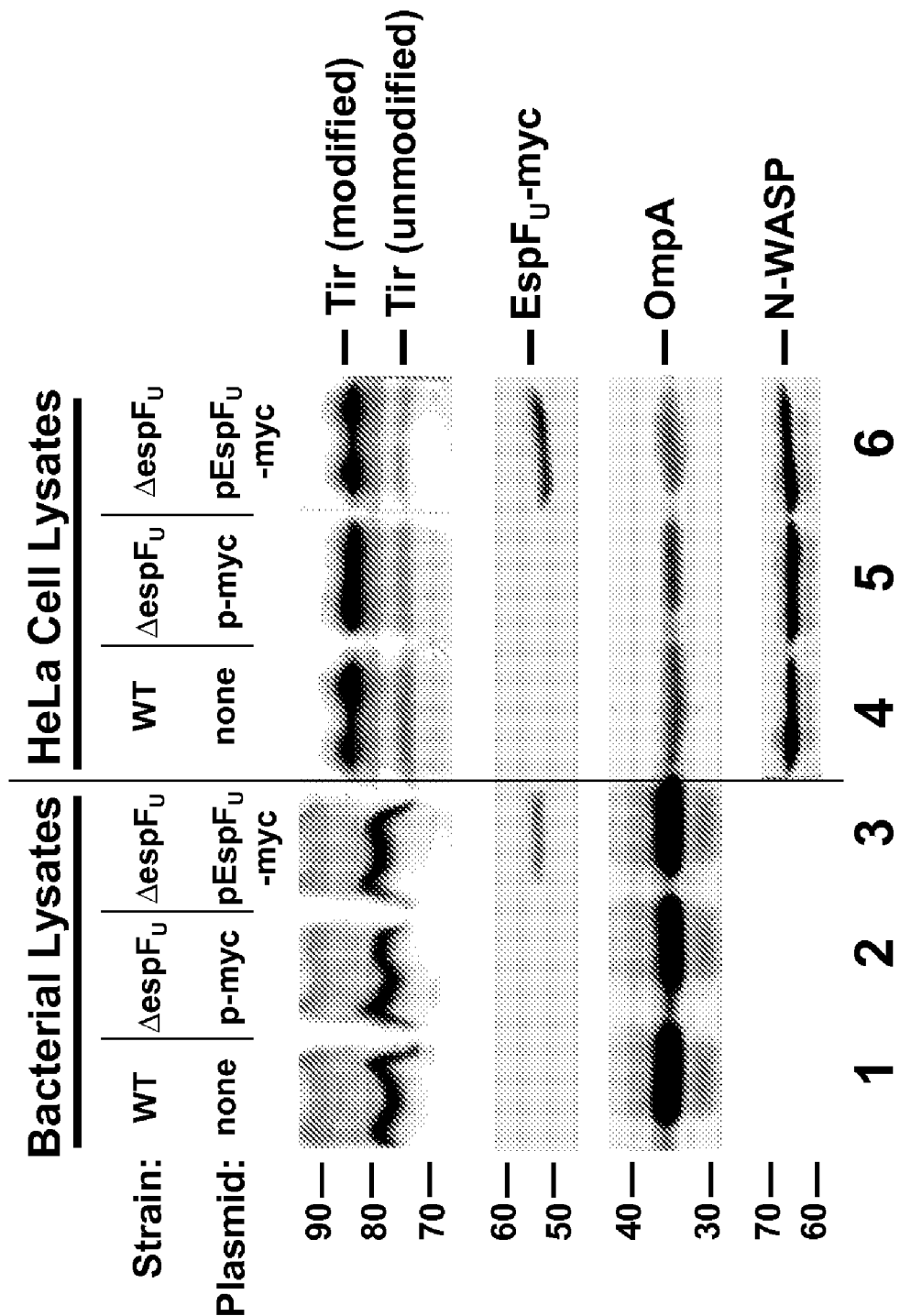
FIG. 3 is an image of Western blots for Tir and myc-tagged EspF$_U$ in EHEC cell lysates (lanes 1-3) or lysates of EHEC-infected HeLa cells (lanes 4-6). Modified translocated form of Tir and the unmodified immature species of Tir can be seen. OmpA immunoblotting demonstrated equivalent protein content within EHEC lysates (lanes 1-3) and similar levels of bacterial association with HeLa cells for each strain (lanes 4-6). N-WASP immunoblotting indicated that similar protein quantities were present in HeLa lysates (lanes 4-6).

After entry into the host cell, EHEC Tir is phosphorylated on serine and/or threonine residues, which increases its apparent molecular weight from approximately 72 kDa to nearly 90 kDa (DeVinney et al., (1999), supra). It has been suggested that EHEC encodes factors that facilitate these modifications of Tir to promote pedestal formation (Kenny, *Cell Microbiol* 3:499-510 (2001)). Therefore, to test whether $EspF_U$ affects Tir translocation into the mammalian cell or its subsequent modification, HeLa cells were infected with wild type EHEC or with EHECΔ$espF_U$ harboring either $pEspF_U$-myc or p-myc. Following removal of non-cell-associated bacteria, mammalian cells were collected, lysed, and immunoblotted for Tir. Consistent with the relationship of Tir translocation to its change in mobility, infection of HeLa cells with wild type EHEC resulted in a shift in Tir migration from 72 kDa to nearly 90 kDa (FIG. 3, lanes 1,4). EHECΔespFU similarly delivered Tir into HeLa cells, and levels of translocation and modification were unaltered by the addition of $EspF_U$-myc (FIG. 3, lanes 5-6).

After insertion into the plasma membrane with its central domain exposed at the cell surface, Tir is maintained beneath sites of EHEC attachment because its ligand, the bacterial outer membrane protein intimin, binds to this region of Tir (DeVinney et al., (1999), supra). Tir translocated in the absence of $EspF_U$ also displayed this localization pattern, as its N-terminal cytoplasmic domain was detectable in HeLa cells beneath EHECΔ$espF_U$ in a manner indistinguishable from wild type EHEC. Hence, $EspF_U$ does not appear to influence the delivery, modification, membrane localization, or intimin-binding activity of Tir.

Example 6

$EspF_U$ allows KC12, an EPEC Strain that Expresses EHEC Tir, to Efficiently Generate Actin Pedestals Independent of Nck Adaptors The ability of EHECΔ$espF_U$ to translocate Tir but not initiate actin assembly is strikingly similar to the phenotypes of EPEC strains that have been engineered to express EHEC Tir (Campellone et al., (2002), supra; DeVinney et al., (2001), supra; Kenny, (2001). One such strain, KC12, is an EPEC derivative in which the endogenous chromosomal copy of tir has been replaced with sequence encoding an N-terminally HA-tagged version of EHEC Tir (Campellone et al., (2002). Tir translocated by KC12 localizes beneath adherent bacteria, but fails to efficiently trigger pedestal formation, presumably because EPEC lacks one or more effectors that are exclusively present in EHEC and function to promote actin assembly independent of tyrosine phosphorylation. A search of the EPEC genome database indicated that an $espF_U$-like gene was not present. Therefore, to determine if $EspF_U$ is the only EHEC effector of pedestal formation that is missing from EPEC, p-myc and $pEspF_U$-myc were introduced into KC12. Similar to EHEC strains lacking $EspF_U$ (FIG. 1), KC12 harboring the vector control formed pedestals only at low levels (Table 1). In contrast, the expression of $EspF_U$-myc by KC12 resulted in its translocation into host cells, and remarkably promoted the formation of pedestals at an efficiency equivalent to that of an EPEC strain expressing EPEC Tir (Table 1). Thus, $EspF_U$ is the only EHEC-specific effector necessary for localized actin assembly.

TABLE 1

| EspFU can induce pedestal formation in EPEC KC12 | |
|---|---|
| Strain | Pedestals/100 Tir⁺ Bacteria |
| EPECΔtir + pHA-$Tir_{EPEC}$ | 98.2 ± 2.1 |
| EPEC KC12 + p-myc | 6.1 ± 1.1 |
| EPEC KC12 + pEspFU-myc | 100.0 ± 0.0 |

Whereas EPEC utilizes its tyrosine phosphorylated Tir molecule to recruit the Nck adaptor proteins to initiate actin polymerization, EHEC generates pedestals independently of Nck (Campellone et al., (2002) supra; Gruenheid et al., *Nat Cell Biol* 3:856-9 (2001)). Indeed, the inability of EHEC Tir to recruit Nck is likely responsible for its inability to function for actin assembly when expressed in KC12. To examine whether Nck was recruited to pedestals formed by KC12 expressing $EspF_U$-myc, infected HeLa cells were stained for this adaptor. In contrast to wild type EPEC, but similar to wild type EHEC, strain KC12 carrying $pEspF_U$-myc did not recruit Nck.

The observation that KC12 expressing $EspF_U$ generates pedestals without detectable Nck recruitment suggests that $EspF_U$ promotes a bypass of Nck-dependent pathways to actin assembly. To test this hypothesis, Nck-proficient and Nck-deficient mouse embryonic fibroblasts (MEFs) (Bladt et al., Mol Cell Biol 23:4586-97 (2003)); Gruenheild et al., (2001) supra) were infected with an EPEC strain that expresses its own tyrosine-phosphorylated Tir, or with KC12 expressing $EspF_U$. Actin pedestal formation initiated by EPEC Tir was significantly reduced both in intensity and frequency on cells that lack Nck (Table 2). In contrast, the KC12 derivative expressing EspF$_U$ generated pedestals at equivalent levels on both cell lines, and at efficiencies indistinguishable from pedestals formed by wild type EPEC on Nck-proficient cells (Table 2). Hence, EspF$_U$ collaborates with EHEC Tir to efficiently trigger localized actin assembly independent of Nck adaptor proteins.

TABLE 2

EspFU can induce actin pedestals in the absence of Nck

| Strain | Pedestals/100 Tir$^+$ Bacteria | |
|---|---|---|
| | Nck +/− host cells | Nck −/− host cells |
| EPECΔtir + pHA-Tir$_{EPEC}$ | 99.8 ± 0.2 | 25.2 ± 1.9 |
| EPEC KC12 + p-myc | 5.1 ± 1.4 | 4.2 ± 2.1 |
| EPEC KC12 + pEspFU-myc | 99.7 ± 0.3 | 99.6 ± 0.2 |

Example 7

EspF$_U$ is Required for Recruitment of the N-WASP-Arp2/3 Actin Assembly Machinery Tir is the only EHEC effector known to be required for recruitment of the N-WASP-Arp2/3 actin nucleating complex to sites of adherence (Goosney et al., *Infect and Immun.* 69:3315-3322 (2001)). To examine whether EspF$_U$ is also required for localization of these components, cells infected with EspF$_U$-deficient and EspF$_U$-proficient strains of EHEC and EPEC were stained for N-WASP and the Arp2/3 complex. Both N-WASP and Arp3 localized beneath EHEC in an EspF$_U$-dependent manner. Similarly, EPEC strain KC12 efficiently recruited N-WASP and Arp3 only in the presence of the complementing EspF$_U$-myc plasmid. Since EHECΔespF$_U$ and KC12 both deliver EHEC Tir into the plasma membrane, EHEC Tir is not sufficient to localize N-WASP and Arp2/3. Rather, EHEC Tir must cooperate with EspF$_U$ in order to efficiently recruit and subsequently activate these fundamental components of the actin assembly machinery.

Notably, EPEC KC12 and EHECΔespF$_U$ behave identically in all aspects of actin pedestal formation that have been tested, suggesting that these two strains are functionally equivalent. By analogy, expression of EspF$_U$ in KC12 apparently creates a strain that corresponds to wild type EHEC in its method of actin pedestal formation. Since EPEC strains bind to cultured cells and translocate effectors with a dramatically greater efficiency than EHEC strains, KC12 and its derivatives provide an optimal experimental tool for the reconstitution of actin pedestal formation by EHEC.

Example 8

EspF$_U$ is an Intermediate Between Tir and N-WASP During Actin Pedestal Formation To investigate the relationship of Tir and EspF$_U$ during the formation of actin pedestals, a direct comparison of the localization of these two effectors was performed. Fluorescent antibody staining of HeLa cells infected with KC12 expressing EspF$_U$ demonstrated that HA-tagged EHEC Tir and myc-tagged EspF$_U$ precisely co-localized beneath adherent bacteria (FIG. 4A), suggesting that these two effectors may physically associate during pedestal formation. To test whether Tir and EspF$_U$ interact within mammalian cells, infected HeLa cells were collected and lysed, and after removal of bacteria, EHEC Tir was immunoprecipitated using an antibody to its HA-epitope. Western blotting demonstrated that both the modified and the unmodified forms of Tir were similarly precipitated from HeLa cell lysates in the presence and absence of EspF$_U$ (FIG. 4B, lanes 5-6). Interestingly, blotting of these same samples with an anti-myc antibody indicated that EspF$_U$ co-precipitated with Tir (FIG. 4B, lane 6). This interaction is specific, because neither Tir nor EspF$_U$ were precipitated from HeLa cell lysates when a control antibody was used (FIG. 4B, lanes 3-4) or when anti-HA precipitations were performed on lysates that contained an untagged version of EHEC Tir (not shown).

Since EspF$_U$ associates with Tir at the tip of pedestal, the site where actin polymerization occurs, its role as an effector during pedestal formation may be to mediate an interaction between Tir and actin assembly components. Indeed, both Tir and EspF$_U$ precisely co-localized in HeLa cells with N-WASP (FIG. 4A). To test whether EspF$_U$ is capable of interacting with N-WASP, cells infected with KC12 derivatives were lysed and supplemented with purified recombinant N-WASP prior to immunoprecipitation of myc-tagged EspF$_U$. Western blotting demonstrated that N-WASP co-precipitated with EspF$_U$-myc (FIG. 4C, lane 7). In contrast, N-WASP was not precipitated by the anti-myc antibody in the absence of EspF$_U$ (FIG. 4C, lane 6) or by a control antibody in the presence of EspF$_U$ (FIG. 4C, lane 5), indicating that the association of EspF$_U$ and N-WASP is specific. Hence, one critical function that EspF$_U$ likely performs during EHEC pedestal formation is to act as an intermediate between Tir and N-WASP.

Example 9

C-Terminal Proline-Rich Region of EspF$_U$ Binds to the GTPase-Binding Domain of N-WASP N-WASP derivatives fused to the LexA DNA-binding domain were co-expressed with EspF$_U$ derivatives fused to the GAL4 activation domain in the yeast reporter strain L40. Interactions between N-WASP-derivatives and EspFU-derivatives were tested in β-galactosidase filter-lift assays or by growing cells on media lacking histidine. EspFU-GAL4 fusions and N-WASP-LexA fusions were engineered using vectors as described (Liu et al., 2002, Mol. Microbiol. 45:1557-73). Plasmids were transformed into the yeast reporter strain L40.

The C-terminus of EspF$_U$, amino acids 80-384 (FIG. 6B), was fused to the GAL4 activation domain in construct EspF$_U$(C). The GTPase binding domain (GBD) of N-WASP was fused to LexA in the construct labeled GBD. The activation of β-galactosidase and histidine reporter genes revealed that the GBD domain of N-WASP and the C-terminus of EspF$_U$ interact strongly.

These experiments also showed that the respective functional domains mediate this interaction. Also, the N-terminus of EspF$_U$ alone, amino acids 1-79, (in construct EspF$_U$(N)) did not interact with the GBD domain in construct WH1-GBD-PRD-VCA. N-WASP fragments lacking a GBD domain, e.g., construct WH1, did not interact with C-terminal domain of EspF$_U$ (EspF$_U$(C)). A construct containing full-length EspF$_U$, EspF$_U$(N+C), also interacted strongly with construct containing full length N-WASP (WH1-GBD-PRD-VCA).

Example 10

EspFU Binds to the SH3 Domain of Toca-1

Figure 13:
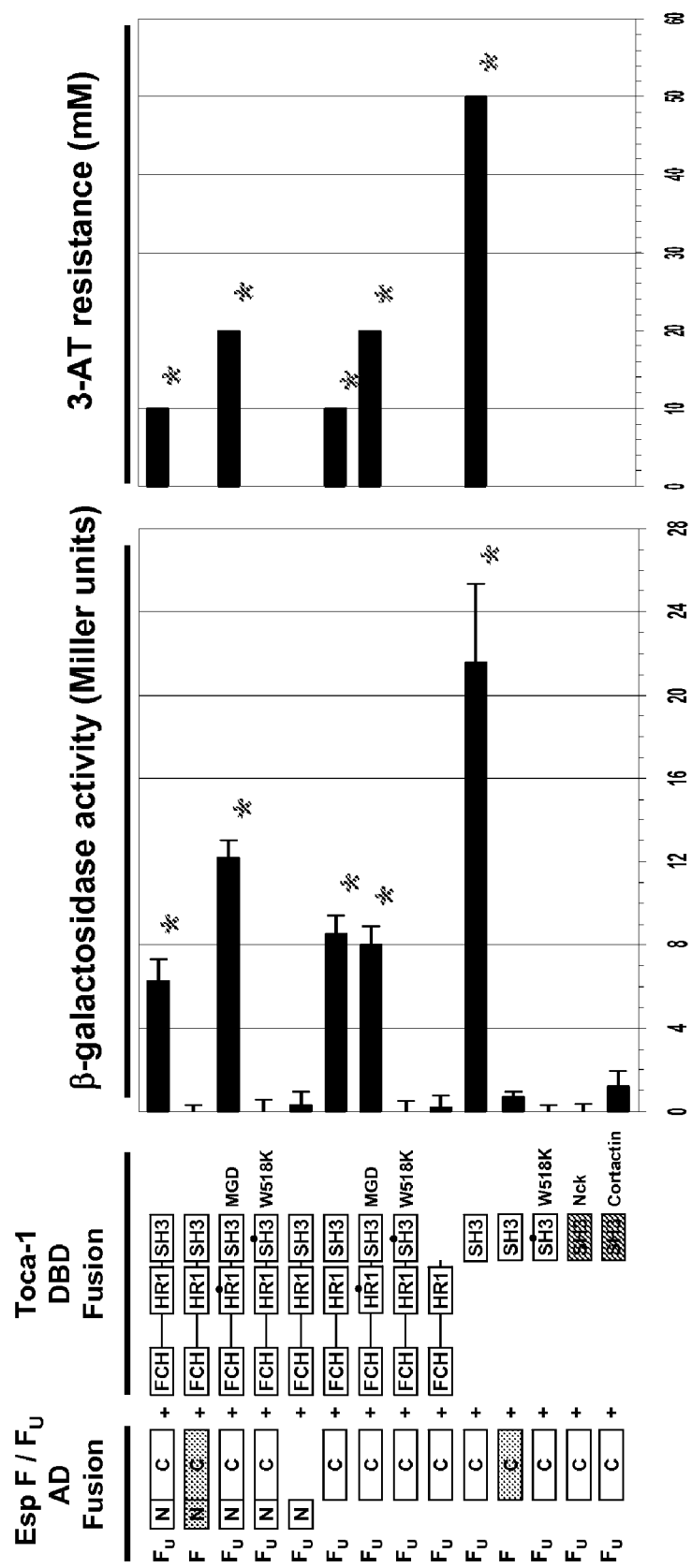
FIG. 13 is a pair of graphs depicting the results of a yeast two-hybrid assay to detect binding of fragments of EspF$_U$ or EspF to fragments of Toca-1, Nck, or cortactin.

Gal4-fusions to fragments of EspF$_U$ or EspF, and LexA-fusions to derivatives of Toca-1 (transducer of Cdc42-dependent actin assembly-1) (Ho et al., *Cell* 118:203-16 (2004)), were coexpressed in the yeast reporter strain L40, which possesses LexA binding sites within the lacZ and HIS3 promoters. Reporter activation was measured by quantitating β-galactosidase activity (Miller units) and 3-aminotriazole (3-AT) resistance (mM) relative to control yeast strains that expressed only the LexA-fusion. The C-terminal domain of EspF$_U$ including the 47-residue repeats and a functional Toca-1 SH3 domain were required for binding activity (FIG. 13). EspF did not bind to Toca-1. Also, the binding of EspF$_U$ was specific for the Toca-1 SH3 domain, as EspF$_U$ did not bind to the SH3 domains of Nck or cortactin. EspFU did not bind to the full-length Toca-1 or Toca-1 SH3 with a mutation in the SH3 domain that eliminates SH3 function. These results demonstrate that EspF$_U$ binds to Toca-1, a protein that can promote actin nucleation.

Example 11

EspF$_U$ Interacts with Pak1

Figure 14A:
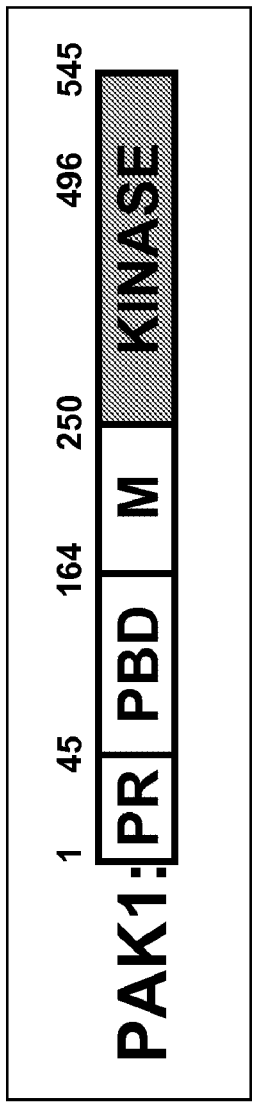
FIG. 14A is a depiction of the domains of Pak1 defined by amino acid position. PR: proline-rich domain; PBD: p21 binding domain; M: middle domain containing several proline-rich sequences and an acidic sequence; KINASE: kinase domain.
Figure 14B:
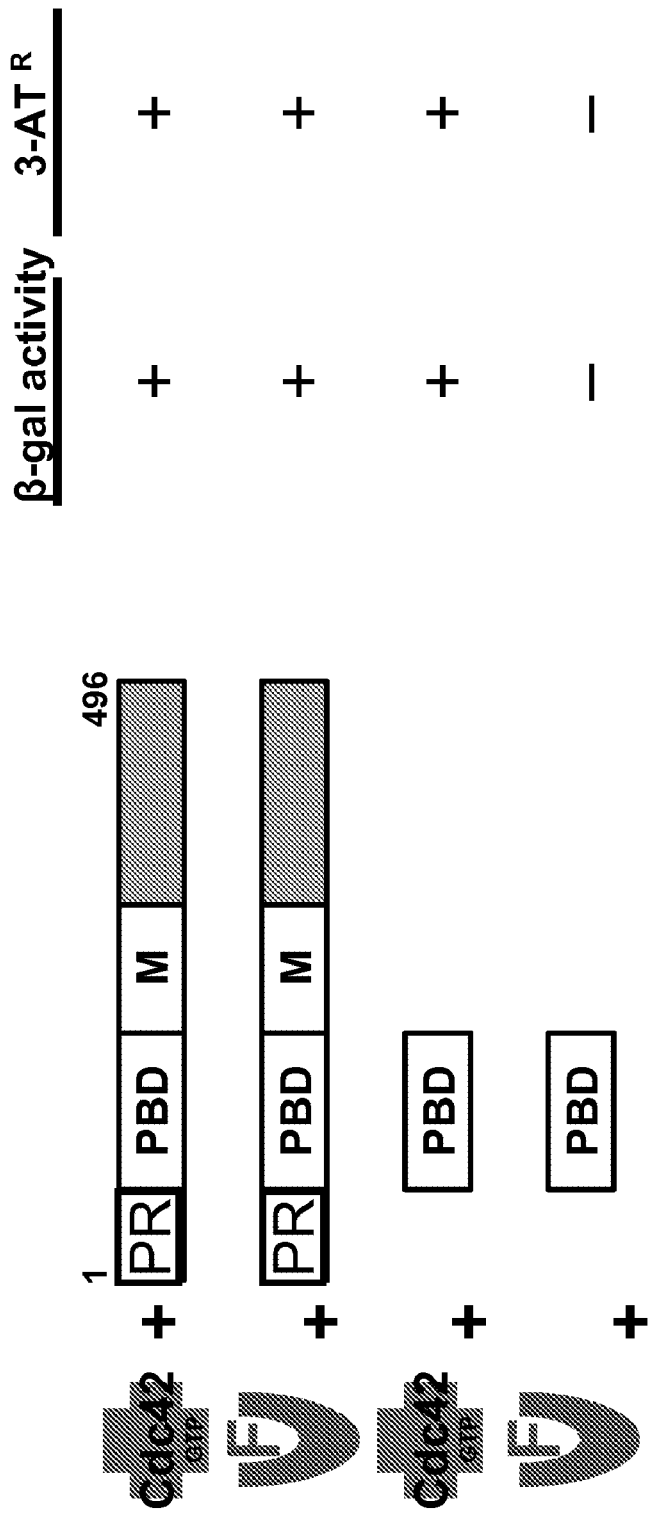
FIG. 14B is a table depicting the results of a yeast two-hybrid assay to detect binding of EspF$_U$ or Cdc42 to fragments of Pak1.

Gal-4-fusions to EspF$_U$ or Cdc42, and LexA-fusions to derivatives of Pak1 (p21-activated kinase 1), were coexpressed in the yeast reporter strain L40, which possesses LexA binding sites within the lacZ and HIS3 promoters. Reporter activation was detected by filter lift assays to assess β-galactosidase activity and growth on media containing 100 mM 3-AT. FIG. 14B depicts the results of the binding of Cdc42 or EspF$_U$ fusion proteins to fusions that include the N-terminus or p21 binding domain of Pak1. "+" indicates binding, as measured by β-galactosidase activity or 3-AT resistance significantly above background. "−" indicates background levels (no detectable binding). EspF$_U$ bound to a fragment consisting of the N-terminal 496 amino acids of Pak1, a proline-rich domain, the p21 binding domain, and middle domain that contains several proline-rich sequences and an acidic sequence (FIG. 14B). However, EspF$_U$ did not bind to the isolated p21-binding domain (PBD), which is known to be required for binding to Cdc42. These results demonstrate that EspF$_U$ binds to Pak1, a protein that can promote actin nucleation.

Example 12

Figure 15:
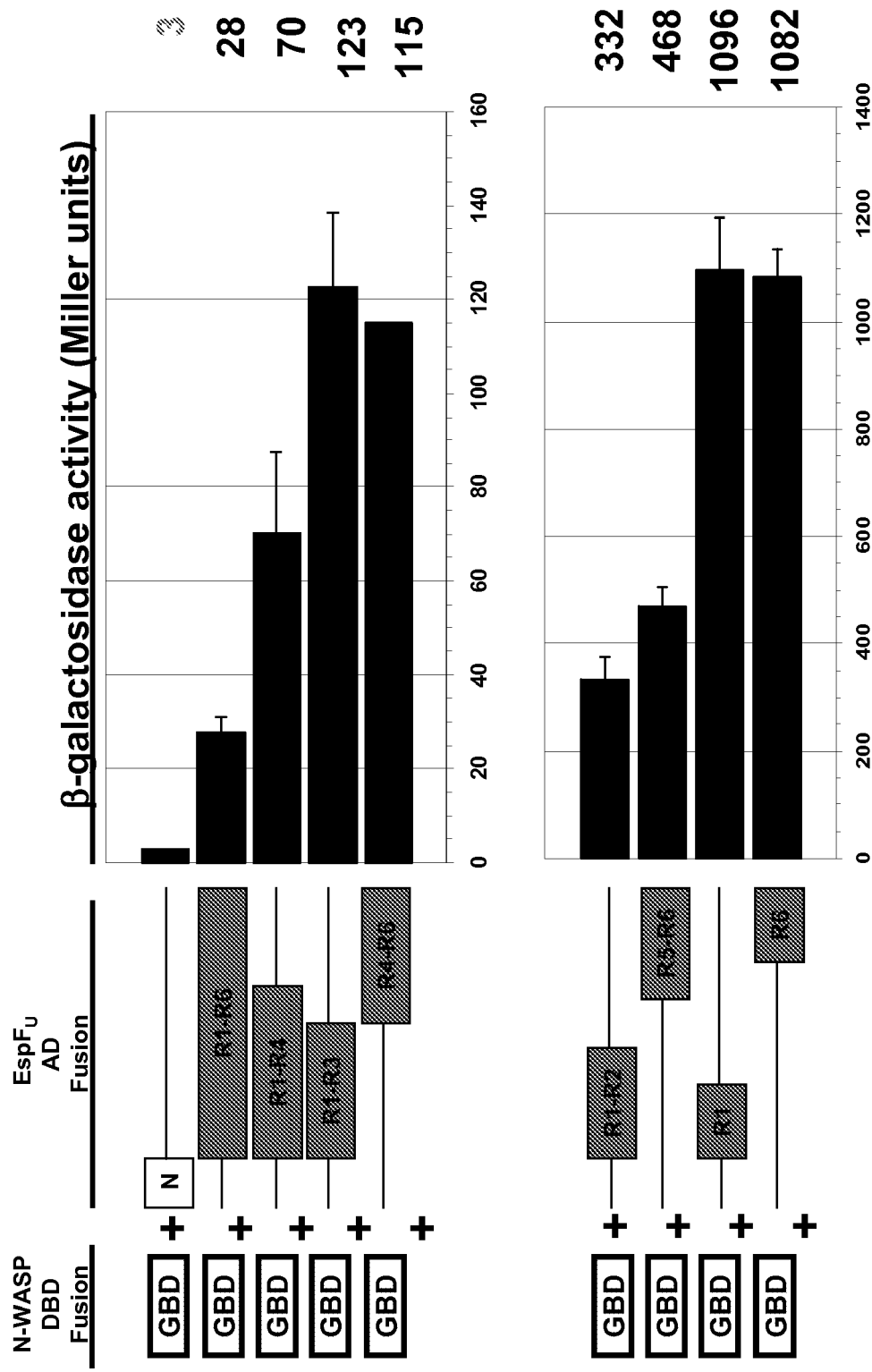
FIG. 15 is a graph depicting the results of a yeast two-hybrid assay to detect binding of the GTPase binding domain (GBD) of N-WASP to fragments of EspF$_U$ containing one or more 47-residue repeat sequences.

A Single 47-Residue Repeat of EspF$_U$ is Sufficient to Bind to the N-WASP GBD LexA-fusions to the N-WASP GBD, and Gal4-fusions to the N-terminus of EspF$_U$ or the C-terminal 47-residue repeats (R1-R6) of EspF$_U$, were coexpressed in the yeast reporter strain L40, which possesses LexA binding sites within the lacZ promoter. FIG. 15 depicts reporter activation as measured by quantitating β-galactosidase activity (Miller units) relative to a control yeast strain expressing the N-WASP GBD and a Gal4 vector control. Data are the means of duplicate samples. As shown in FIG. 15, fragments of EspF$_U$ containing one (R1 or R6), two (R1-R2, R5-R6), three (R1-R3, R4-R6), four (R1-R4), or six (R1-R6) 47-residue repeats bound effectively to the N-WASP GBD. The greater activity observed with smaller fragments of EspFU may be an artifact of the yeast two-hybrid system, as smaller polypeptides are predicted to more easily enter the nucleus to bind and promote transcription. These results indicate that a single 47-residue segment of EspF$_U$ is sufficient to bind to the N-WASP GBD.

Example 13

Clustering of Tir in the Presence of a Single 47-Reside Repeat from the C-Terminus of EspF$_U$ Triggers Localized Actin Assembly A plasma-membrane targeted version of EHEC Tir was co-expressed in HeLa cells with GFP-tagged derivatives of EspF$_U$ containing one, two, three, four, or six copies of its 47-residue C-terminal repeat region. These cells were infected with a non-pathogenic strain of *E. coli* expressing intimin and treated with phalloidin to detect F-actin pedestals. All of the EspF$_U$ derivatives were approximately equally competent to induce actin pedestal formation in this system, whereas GFP alone did not induce actin pedestal formation. These results indicate that one 47-residue segment of EspF$_U$ is sufficient to cluster Tir and trigger actin pedestal formation.

Example 14

EspF$_U$ Deletion Mutants do not form Actin Pedestals In Vivo

Colonization and pedestal formation of EspF$_U$ deletion mutants were investigated in a gnotobiotic piglet model of infection. For these studies, 933-TUV, a non-toxin producing derivative of EHEC EDL933, was compared to an espF$_U$ deletion derivative of 933-TUV. One day old piglets were infected perorally with approximately 5×10$^9$ colony forming units of 933-TUV or 933-TUV with the coding sequence of EspF$_U$ deleted. Piglets were euthanized after 48 hours, and the mucosal surface of the gut was observed using light microscopy. Similar numbers of bacteria were observed associated with the mucosal surfaces of piglets infected with 933-TUV or 933-TUVΔespF$_U$. However, electron microscopy revealed that whereas the 933-TUV were typically associated with actin pedestals on the epithelial surface, the 933-TUVΔespF$_U$ mutant bacteria were typically not associated with pedestals. In addition, whereas 933-TUV was found predominantly bound to the epithelial surface, 933-TUVΔespF$_U$ was found abundantly in intracellular vacuoles. These results demonstrate that EspF$_U$ is important for actin pedestal formation in vivo and may be involved in preventing internalization of the bacteria by mammalian cells.

Example 15

EspF$_U$ Deletion Mutants do not Affect Colonization In Vivo

Colonization of EspF$_U$ deletion mutants was investigated in an infant rabbit model of infection. Infant rabbits were infected perorally with 5×10$^8$ colony forming units of wild-type EHEC or EHEC with the coding sequence of EspF$_U$ deleted. The animals were euthanized on day 2 and 7 post infection and colonization of the ileum, cecum, midcolon and stool was determined by measuring colony forming units in the tissues. Briefly, the tissues were dissected, homogenized, and plated on Sorbitol MacConkey medium. No significant differences in the numbers of colonizing bacteria were observed between the wild-type and EspF$_U$ mutant EHEC in this animal model. Actin pedestal formation was not measured.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A purified polypeptide that comprises an amino acid sequence that is at least 97% identical to SEQ ID NO:2, wherein said polypeptide binds to a neuronal Wiskott-Aldrich syndrome protein (N-WASP).

2. The purified polypeptide of claim 1, wherein the amino acid sequence is at least 98% identical to SEQ ID NO:2.

3. The purified polypeptide of claim 1, wherein the polypeptide comprises the amino acid sequence of SEQ ID NO:2.

4. The polypeptide of claim 1, wherein the polypeptide restores actin pedestal formation activity of enteropathogenic Escherichia coli (EPEC) strain KC12.

5. A fusion protein comprising:
   (a) the polypeptide of claim 1; and
   (b) a second polypeptide comprising an amino acid sequence unrelated to the first amino acid sequence.

6. The fusion protein of claim 5, wherein the second polypeptide comprises a reporter molecule.

7. The fusion protein of claim 5, wherein the second polypeptide comprises a reporter molecule selected from the group consisting of: a c-myc antigen, at least six consecutive histidines, a chromophore, a fluorophore, a green fluorescent protein, a derivative of green fluorescent protein, biotin, horseradish peroxidase, alkaline phosphatase, β-galactosidase, glucose oxidase, invertase, luciferase, chloramphenicol acetyltransferase, β-glucuronidase, exoglucanase, and glucoamylase.

8. The purified polypeptide of claim 1, wherein the polypeptide comprises at least amino acids 80 to 384 of SEQ ID NO:2.

9. A purified polypeptide encoded by a nucleic acid at least 98% identical to nucleotides 238-1152 of SEQ ID NO:1.

10. A purified polypeptide that comprises an amino acid sequence that is at least 95% identical to amino acids 80 to 384 of SEQ ID NO:2 (SEQ ID NO:4), wherein said polypeptide binds to a neuronal Wiskott-Aldrich syndrome protein (N-WASP).

11. The purified polypeptide of claim 10, wherein the amino acid sequence is at least 99% identical to SEQ ID NO:4.

12. The purified polypeptide of claim 10, wherein the polypeptide comprises the amino acid sequence of SEQ ID NO:4.

13. A method of diagnosing or detecting an enterohemorrhagic Escherichia coli (EHEC) infection, the method comprising:
   providing a sample suspected of having an EHEC infection; and
   detecting the polypeptide of claim 10 in the sample.

14. The method of claim 13, wherein the sample is obtained from a subject.

15. A method of diagnosing and treating an enterohemorrhagic Escherichia coli (EHEC) infection, the method comprising:
   performing the method of claim 14; and
   if the polypeptide is detected in the sample, treating the subject with a treatment that does not enhance production of Shiga-like toxin.

* * * * *

UNITED STATES PATENT AND TRADEMARK OFFICE
CERTIFICATE OF CORRECTION

PATENT NO. : 7,732,409 B2  Page 1 of 1
APPLICATION NO. : 11/782479
DATED : June 8, 2010
INVENTOR(S) : John M. Leong It is certified that error appears in the above-identified patent and that said Letters Patent is hereby corrected as shown below:

Claim 7, column 73, line 43:
  delete "chioramphenicol" and replace with --chloramphenicol--.

Signed and Sealed this

Seventeenth Day of August, 2010

David J. Kappos
*Director of the United States Patent and Trademark Office*

```
                         SEQUENCE LISTING

<160> NUMBER OF SEQ ID NOS: 26

<210> SEQ ID NO 1
<211> LENGTH: 1155
<212> TYPE: DNA
<213> ORGANISM: Escherichia coli

<400> SEQUENCE: 1
atgattaaca atgtttcttc acttttttcca accgtcaacc gcaatattac agctgtatat      60
aaaaaaagca gcttctctgt atcaccacag aaaatcacat taaatcctgt aaaaatcagc     120
tcaccttttt caccaagcag tagctccatc agcgcaacaa ctctctttcg agccccaaac     180
gcccattcgg catcatttca tcgacagtct actgctgaaa gttcgttaca tcaacaactt     240
cctaatgtga ggcagcgcct gatacaacat cttgcagagc atggcattaa acctgcccgg     300
agtatggctg aacatattcc tccggcacct aactggcctg cgccaccacc gccagtacaa     360
aatgaacaat caagacctct gcctgatgtg gctcagcgtc tggtgcagca tcttgcagag     420
catggcattc aaccagcccg gaatatggct gaacatattc ctccggcacc taactggcct     480
gcgccaccac tgccagtaca aaatgaacaa tcaagacctc tgcctgatgt ggctcagcgt     540
ctggtgcagc atcttgcaga gcatggcatt caaccagccc ggagtatggc tgaacatatt     600
cctccggcac taactggcc tgcgccacca ccgccagtac aaaatgaaca atcaagacct     660
ctgcctgatg tggctcagcg tctggtgcag catcttgcag agcatggcat tcaaccagcc     720
cggagtatgg ctgaacatat tcctccggca cctaactggc ctgcgccacc accgccagta     780
caaaatgaac aatcaagacc tctgcctgat gtggctcagc gtctgatgca gcatcttgca     840
gagcatggca ttcaaccagc ccggaatatg gctgaacata ttcctccggc acctaactgg     900
cctgcgccaa cgccgccagt acaaaatgaa caatcaagac ctttgcctga tgtggctcag     960
cgtctgatgc agcatcttgc agagcatggc attcaaccag cccggaatat ggctgaacat    1020
attcctccgg cacctaactg gcctgcgcca acgccgccag tacaaaatga acaatcaaga    1080
cctttgcctg atgtggctca gcgtctgatg cagcatcttg cagagcatgg cattaataca    1140
tctaagcgct cgtga                                                    1155

<210> SEQ ID NO 2
<211> LENGTH: 384
<212> TYPE: PRT
<213> ORGANISM: Escherichia coli

<400> SEQUENCE: 2

Met Ile Asn Asn Val Ser Ser Leu Phe Pro Thr Val Asn Arg Asn Ile
1               5                   10                  15

Thr Ala Val Tyr Lys Lys Ser Ser Phe Ser Val Ser Pro Gln Lys Ile
            20                  25                  30

Thr Leu Asn Pro Val Lys Ile Ser Ser Pro Phe Ser Pro Ser Ser Ser
        35                  40                  45

Ser Ile Ser Ala Thr Thr Leu Phe Arg Ala Pro Asn Ala His Ser Ala
    50                  55                  60
```

```
Ser Phe His Arg Gln Ser Thr Ala Glu Ser Ser Leu His Gln Gln Leu
 65                  70                  75                  80

Pro Asn Val Arg Gln Arg Leu Ile Gln His Leu Ala Glu His Gly Ile
                 85                  90                  95

Lys Pro Ala Arg Ser Met Ala Glu His Ile Pro Ala Pro Asn Trp
            100                 105                 110

Pro Ala Pro Pro Pro Val Gln Asn Glu Gln Ser Arg Pro Leu Pro
        115                 120                 125

Asp Val Ala Gln Arg Leu Val Gln His Leu Ala Glu His Gly Ile Gln
130                 135                 140

Pro Ala Arg Asn Met Ala Glu His Ile Pro Pro Ala Pro Asn Trp Pro
145                 150                 155                 160

Ala Pro Pro Leu Pro Val Gln Asn Glu Gln Ser Arg Pro Leu Pro Asp
                165                 170                 175

Val Ala Gln Arg Leu Val Gln His Leu Ala Glu His Gly Ile Gln Pro
            180                 185                 190

Ala Arg Ser Met Ala Glu His Ile Pro Pro Ala Pro Asn Trp Pro Ala
        195                 200                 205

Pro Pro Pro Val Gln Asn Glu Gln Ser Arg Pro Leu Pro Asp Val
210                 215                 220

Ala Gln Arg Leu Val Gln His Leu Ala Glu His Gly Ile Gln Pro Ala
225                 230                 235                 240

Arg Ser Met Ala Glu His Ile Pro Pro Ala Pro Asn Trp Pro Ala Pro
                245                 250                 255

Pro Pro Pro Val Gln Asn Glu Gln Ser Arg Pro Leu Pro Asp Val Ala
            260                 265                 270

Gln Arg Leu Met Gln His Leu Ala Glu His Gly Ile Gln Pro Ala Arg
        275                 280                 285

Asn Met Ala Glu His Ile Pro Pro Ala Pro Asn Trp Pro Ala Pro Thr
290                 295                 300

Pro Pro Val Gln Asn Glu Gln Ser Arg Pro Leu Pro Asp Val Ala Gln
305                 310                 315                 320

Arg Leu Met Gln His Leu Ala Glu His Gly Ile Gln Pro Ala Arg Asn
                325                 330                 335

Met Ala Glu His Ile Pro Pro Ala Pro Asn Trp Pro Ala Pro Thr Pro
            340                 345                 350

Pro Val Gln Asn Glu Gln Ser Arg Pro Leu Pro Asp Val Ala Gln Arg
        355                 360                 365

Leu Met Gln His Leu Ala Glu His Gly Ile Asn Thr Ser Lys Arg Ser
370                 375                 380
```

<210> SEQ ID NO 3
<211> LENGTH: 918
<212> TYPE: DNA
<213> ORGANISM: Escherichia coli

<400> SEQUENCE: 3

```
cttcctaatg tgaggcagcg cctgatacaa catcttgcag agcatggcat taaacctgcc     60
cggagtatgg ctgaacatat tcctccggca cctaactggc ctgcgccacc accgccagta    120
caaaatgaac aatcaagacc tctgcctgat gtggctcagc gtctggtgca gcatcttgca    180
gagcatggca ttcaaccagc cggaatatg gctgaacata ttcctccggc acctaactgg    240
cctgcgccac cactgccagt acaaaatgaa caatcaagac tctgcctga tgtggctcag    300 cgtctggtgc agcatcttgc agagcatggc attcaaccag cccggagtat ggctgaacat    360
```

-continued

```
attcctccgg cacctaactg gcctgcgcca ccaccgccag tacaaaatga acaatcaaga      420
cctctgcctg atgtggctca gcgtctggtg cagcatcttg cagagcatgg cattcaacca      480
gcccggagta tggctgaaca tattcctccg gcacctaact ggcctgcgcc accaccgcca      540
gtacaaaatg aacaatcaag acctctgcct gatgtggctc agcgtctgat gcagcatctt      600
gcagagcatg gcattcaacc agcccggaat atggctgaac atattcctcc ggcacctaac      660
tggcctgcgc aacgccgcc agtacaaaat gaacaatcaa gacctttgcc tgatgtggct      720
cagcgtctga tgcagcatct tgcagagcat ggcattcaac cagcccggaa tatggctgaa      780
catattcctc cggcacctaa ctggcctgcg ccaacgccgc cagtacaaaa tgaacaatca      840
agacctttgc ctgatgtggc tcagcgtctg atgcagcatc ttgcagagca tggcattaat      900
acatctaagc gctcgtga                                                    918
```

```
<210> SEQ ID NO 4
<211> LENGTH: 304
<212> TYPE: PRT
<213> ORGANISM: Escherichia coli

<400> SEQUENCE: 4

Leu Pro Asn Val Arg Gln Arg Leu Ile Gln His Leu Ala Glu His Gly
1               5                   10                  15

Ile Lys Pro Ala Arg Ser Met Ala Glu His Ile Pro Ala Pro Asn
            20                  25                  30

Trp Pro Ala Pro Pro Pro Val Gln Asn Glu Gln Ser Arg Pro Leu
        35                  40                  45

Pro Asp Val Ala Gln Arg Leu Val Gln His Leu Ala Glu His Gly Ile
    50                  55                  60

Gln Pro Ala Arg Asn Met Ala Glu His Ile Pro Pro Ala Pro Asn Trp
65                  70                  75                  80

Pro Ala Pro Pro Leu Pro Val Gln Asn Glu Gln Ser Arg Pro Leu Pro
                85                  90                  95

Asp Val Ala Gln Arg Leu Val Gln His Leu Ala Glu His Gly Ile Gln
            100                 105                 110

Pro Ala Arg Ser Met Ala Glu His Ile Pro Pro Ala Pro Asn Trp Pro
        115                 120                 125

Ala Pro Pro Pro Val Gln Asn Glu Gln Ser Arg Pro Leu Pro Asp
    130                 135                 140

Val Ala Gln Arg Leu Val Gln His Leu Ala Glu His Gly Ile Gln Pro
145                 150                 155                 160

Ala Arg Ser Met Ala Glu His Ile Pro Pro Ala Pro Asn Trp Pro Ala
                165                 170                 175

Pro Pro Pro Val Gln Asn Glu Gln Ser Arg Pro Leu Pro Asp Val
            180                 185                 190

Ala Gln Arg Leu Met Gln His Leu Ala Glu His Gly Ile Gln Pro Ala
        195                 200                 205

Arg Asn Met Ala Glu His Ile Pro Pro Ala Pro Asn Trp Pro Ala Pro
    210                 215                 220

Thr Pro Pro Val Gln Asn Glu Gln Ser Arg Pro Leu Pro Asp Val Ala
225                 230                 235                 240

Gln Arg Leu Met Gln His Leu Ala Glu His Gly Ile Gln Pro Ala Arg
                245                 250                 255

Asn Met Ala Glu His Ile Pro Pro Ala Pro Asn Trp Pro Ala Pro Thr
            260                 265                 270
```

```
Pro Pro Val Gln Asn Glu Gln Ser Arg Pro Leu Pro Asp Val Ala Gln
        275                 280                 285

Arg Leu Met Gln His Leu Ala Glu His Gly Ile Asn Thr Ser Lys Arg
        290                 295                 300

<210> SEQ ID NO 5
<211> LENGTH: 1518
<212> TYPE: DNA
<213> ORGANISM: Homo sapiens

<400> SEQUENCE: 5
atgagctccg tccagcagca gccgccgccg ccgcggaggg tcaccaacgt ggggtccctg      60
ttgctcaccc cgcaggagaa cgagtccctc ttcactttcc tcggcaagaa atgtgtgact     120
atgtcttcag cagtggtgca gttatatgca gcagatcgga actgtatgtg gtcaaagaag     180
tgcagtggtg ttgcttgtct tgttaaggac aatccacaga gatcttattt tttaagaata     240
tttgacatta aggatgggaa actattgtgg gaacaagagc tatacaataa ctttgtatat     300
aatagtccta gaggatattt tcatacccttt gctggagata cttgtcaagt tgctcttaat     360
tttgccaatg aagaagaagc aaaaaaattt cgaaaagcag ttacagacct tttgggccgt     420
cgacaaagga atctgagaa agacgagat ccccaaatg gtcctaatct acccatggct     480
acagttgata taaaaaatcc agaaatcaca acaaatagat tttatggtcc acaagtcaac     540
aacatctccc ataccaaaga aaagaagaag ggaaaagcta aaagaagag attaaccaag     600 gcagatatag gaacaccaag caattccag cacattggac atgttggttg ggatccaaat     660
acaggctttg atctgaataa tttggatcca gaattgaaga tcttttcga tatgtgtgga     720 atctcagagg cacaacttaa agacagaaa acatcaaaag ttatatatga ctttattgaa     780
aaaacaggag gtgttgaagc tgttaaaaat gaactgcgga ggcaagcacc accacctcca     840
ccaccatcaa ggggaggggcc acctcctcct cctccccctc cacacaactc aggtcctcct     900
cctcctcctg ctaggggaag aggcgctcct ccccccaccac cttcaagagc tcccacagct     960
gcacctccac caccgcctcc ttccaggcca agtgtagcag tccctccacc accgccaaat    1020
aggatgtacc ctcctccacc tccagccctt ccctcctcag caccttcagg gcctccacca    1080
ccacctccat ctgtgttggg ggtagggcca gtggcaccac cccaccgcc tccacctcca    1140 cctcctcctg ggccaccgcc ccgcctggc ctgccttctg atggggacca tcaggttcca    1200
actactgcag aaacaaagc agctctttta gatcaaatta gagagggtgc tcagctaaaa    1260 aaagtgggagc agaacagtcg gccagtgtcc tgctctggac gagatgcact gttagaccag    1320
atacgacagg gtatccaact aaaatctgtg gctgatggcc aagagtctac accaccaaca    1380
cctgcaccca ttcaggaat tgtgggtgca ttaatggaag tgatgcagaa aaggagcaaa    1440
gccattcatt cttcagatga agatgaagat gaagatgatg aagaagattt tgaggatgat    1500
gatgagtggg aagactga                                                  1518

<210> SEQ ID NO 6
<211> LENGTH: 505
<212> TYPE: PRT
<213> ORGANISM: Homo sapiens

<400> SEQUENCE: 6

Met Ser Ser Val Gln Gln Gln Pro Pro Pro Arg Arg Val Thr Asn
1               5                   10                  15
```

```
Val Gly Ser Leu Leu Thr Pro Gln Glu Asn Glu Ser Leu Phe Thr
         20                  25                  30

Phe Leu Gly Lys Lys Cys Val Thr Met Ser Ser Ala Val Val Gln Leu
         35                  40                  45

Tyr Ala Ala Asp Arg Asn Cys Met Trp Ser Lys Cys Ser Gly Val
 50                  55                  60

Ala Cys Leu Val Lys Asp Asn Pro Gln Arg Ser Tyr Phe Leu Arg Ile
 65                  70                  75                  80

Phe Asp Ile Lys Asp Gly Lys Leu Leu Trp Glu Gln Glu Leu Tyr Asn
                 85                  90                  95

Asn Phe Val Tyr Asn Ser Pro Arg Gly Tyr Phe His Thr Phe Ala Gly
                100                 105                 110

Asp Thr Cys Gln Val Ala Leu Asn Phe Ala Asn Glu Glu Glu Ala Lys
            115                 120                 125

Lys Phe Arg Lys Ala Val Thr Asp Leu Leu Gly Arg Arg Gln Arg Lys
130                 135                 140

Ser Glu Lys Arg Arg Asp Pro Pro Asn Gly Pro Asn Leu Pro Met Ala
145                 150                 155                 160

Thr Val Asp Ile Lys Asn Pro Glu Ile Thr Thr Asn Arg Phe Tyr Gly
                165                 170                 175

Pro Gln Val Asn Asn Ile Ser His Thr Lys Glu Lys Lys Gly Lys
                180                 185                 190

Ala Lys Lys Lys Arg Leu Thr Lys Ala Asp Ile Gly Thr Pro Ser Asn
            195                 200                 205

Phe Gln His Ile Gly His Val Gly Trp Asp Pro Asn Thr Gly Phe Asp
210                 215                 220

Leu Asn Asn Leu Asp Pro Glu Leu Lys Asn Leu Phe Asp Met Cys Gly
225                 230                 235                 240

Ile Ser Glu Ala Gln Leu Lys Asp Arg Glu Thr Ser Lys Val Ile Tyr
                245                 250                 255

Asp Phe Ile Glu Lys Thr Gly Gly Val Glu Ala Val Lys Asn Glu Leu
                260                 265                 270

Arg Arg Gln Ala Pro Pro Pro Pro Ser Arg Gly Gly Pro Pro
            275                 280                 285

Pro Pro Pro Pro Pro His Asn Ser Gly Pro Pro Pro Pro Ala
290                 295                 300

Arg Gly Arg Gly Ala Pro Pro Pro Ser Arg Ala Pro Thr Ala
305                 310                 315                 320

Ala Pro Pro Pro Pro Ser Arg Pro Ser Val Ala Val Pro Pro
            325                 330                 335

Pro Pro Pro Asn Arg Met Tyr Pro Pro Pro Pro Ala Leu Pro Ser
                340                 345                 350

Ser Ala Pro Ser Gly Pro Pro Pro Pro Pro Ser Val Leu Gly Val
            355                 360                 365

Gly Pro Val Ala Pro Pro Pro Pro Pro Pro Pro Pro Gly
 370                 375                 380

Pro Pro Pro Pro Pro Gly Leu Pro Ser Asp Gly Asp His Gln Val Pro
385                 390                 395                 400

Thr Thr Ala Gly Asn Lys Ala Ala Leu Leu Asp Gln Ile Arg Glu Gly
                405                 410                 415

Ala Gln Leu Lys Lys Val Glu Gln Asn Ser Arg Pro Val Ser Cys Ser
            420                 425                 430
```

Gly Arg Asp Ala Leu Leu Asp Gln Ile Arg Gln Gly Ile Gln Leu Lys
            435                 440                 445

Ser Val Ala Asp Gly Gln Glu Ser Thr Pro Thr Pro Ala Pro Thr
    450                 455                 460

Ser Gly Ile Val Gly Ala Leu Met Glu Val Met Gln Lys Arg Ser Lys
465                 470                 475                 480

Ala Ile His Ser Ser Asp Glu Asp Glu Asp Asp Glu Asp
                485                 490                 495

Phe Glu Asp Asp Asp Glu Trp Glu Asp
            500                 505

<210> SEQ ID NO 7
<211> LENGTH: 1506
<212> TYPE: DNA
<213> ORGANISM: Rattus norvegicus

<400> SEQUENCE: 7
atgagctcgg gccagcagcc cccgcggagg gtcaccaacg tgggctccct gctgctcacc      60
ccgcaagaaa acgagtctct tttctccttc ctcggcaaga atgtgtgac tatgtcttca     120 gcagtggtgc agttatatgc agctgatcgg aactgtatgt ggtcaaagaa gtgcagtggt     180
gttgcttgtc ttgttaagga caatcctcag agatcttatt ttttaagaat atttgacatt     240
aaggatggga aattactgtg gaacaagag ctatacaata actttgtata aatagtcct      300 agaggatatt ttcatacctt tgctggagat acttgtcaag tagctcttaa ttttgccaat     360
gaagaagaag caaaaaagtt ccgaaaagca gttacagacc tgttgggtcg acgacaaagg     420
aaatctgaaa aaagacgaga tgctccaaat ggtcccaatc tacccatggc tacagttgac     480
ataaaaaatc cagaaatcac aacaaacagg ttttatagtt cacaagtcaa caacatctcc     540
cacaccaaag aaaagaagaa aggaaaagct aaaagaagaa gattaaccaa ggcagatatt     600
ggaacaccaa gtaatttcca gcacattgga catgttggtt gggatccaaa tacaggtttt     660
gatctaaata atttggatcc agaattgaag aatcttttg atatgtgtgg atctctgag      720 gcccagctta agacagaga acatcaaaa gttatttatg actttattga aaaaacagga      780
ggtgtagaag ctgttaaaaa tgaactccga aggcaagcac caccacctcc tccaccctca    840
agaggaggac ctcccctcc tcctcccct cctcacagct caggccctcc tcccctcct      900 gcccgtggaa gggggctcc tcccccgcca ccatcaagag ctcctactgc tgcacctcca    960
cctccacctc cttctaggcc tggtgttgtc gttcctccac ctcctccaaa caggatgtac   1020
cctcctccac caccagccct gccttcctca gcaccttcag gcccaccacc acctccgcct   1080
ctgtctatgg cagggtccac agcaccacca cctcctccac cacctccccc tccaccaggg   1140
ccaccacctc cccctggcct gccttctgat ggtgaccatc aagttccagc ttcttcagga   1200
aacaaagcag ctcttttgga tcaaattaga gagggtgctc agctaaaaaa agtggagcag   1260
aatagtcggc ccgtgtcctg ctcaggaagg gatgcacttc tagaccagat acgacagggc   1320
attcagttga atccgtgtc tgatggccaa gagtccacac caccaacccc cgcgcccact   1380
tcaggaattg tgggtgcgct gatggaagtg atgcagaaaa ggagcaaagc cattcattcc   1440
tcagatgaag atgaagatga tgatgatgaa gaagatttg aggatgatga tgagtgggaa   1500
gactga                                                               1506

<210> SEQ ID NO 8
<211> LENGTH: 501
<212> TYPE: PRT

<213> ORGANISM: Rattus norvegicus

<400> SEQUENCE: 8

```
Met Ser Ser Gly Gln Gln Pro Pro Arg Arg Val Thr Asn Val Gly Ser
1               5                   10                  15

Leu Leu Leu Thr Pro Gln Glu Asn Glu Ser Leu Phe Ser Phe Leu Gly
            20                  25                  30

Lys Lys Cys Val Thr Met Ser Ser Ala Val Val Gln Leu Tyr Ala Ala
            35                  40                  45

Asp Arg Asn Cys Met Trp Ser Lys Lys Cys Ser Gly Val Ala Cys Leu
        50                  55                  60

Val Lys Asp Asn Pro Gln Arg Ser Tyr Phe Leu Arg Ile Phe Asp Ile
65                  70                  75                  80

Lys Asp Gly Lys Leu Leu Trp Glu Gln Glu Leu Tyr Asn Asn Phe Val
                85                  90                  95

Tyr Asn Ser Pro Arg Gly Tyr Phe His Thr Phe Ala Gly Asp Thr Cys
            100                 105                 110

Gln Val Ala Leu Asn Phe Ala Asn Glu Glu Ala Lys Lys Phe Arg
        115                 120                 125

Lys Ala Val Thr Asp Leu Leu Gly Arg Arg Gln Arg Lys Ser Glu Lys
    130                 135                 140

Arg Arg Asp Ala Pro Asn Gly Pro Asn Leu Pro Met Ala Thr Val Asp
145                 150                 155                 160

Ile Lys Asn Pro Glu Ile Thr Thr Asn Arg Phe Tyr Ser Ser Gln Val
                165                 170                 175

Asn Asn Ile Ser His Thr Lys Glu Lys Lys Gly Lys Ala Lys Lys
            180                 185                 190

Lys Arg Leu Thr Lys Ala Asp Ile Gly Thr Pro Ser Asn Phe Gln His
    195                 200                 205

Ile Gly His Val Gly Trp Asp Pro Asn Thr Gly Phe Asp Leu Asn Asn
    210                 215                 220

Leu Asp Pro Glu Leu Lys Asn Leu Phe Asp Met Cys Gly Ile Ser Glu
225                 230                 235                 240

Ala Gln Leu Lys Asp Arg Glu Thr Ser Lys Val Ile Tyr Asp Phe Ile
                245                 250                 255

Glu Lys Thr Gly Gly Val Glu Ala Val Lys Asn Glu Leu Arg Arg Gln
            260                 265                 270

Ala Pro Pro Pro Pro Pro Ser Arg Gly Gly Pro Pro Pro Pro
        275                 280                 285

Pro Pro Pro His Ser Ser Gly Pro Pro Pro Ala Arg Gly Arg
    290                 295                 300

Gly Ala Pro Pro Pro Pro Ser Arg Ala Pro Thr Ala Ala Pro Pro
305                 310                 315                 320

Pro Pro Pro Pro Ser Arg Pro Gly Val Val Pro Pro Pro Pro
                325                 330                 335

Asn Arg Met Tyr Pro Pro Pro Pro Ala Leu Pro Ser Ser Ala Pro
            340                 345                 350

Ser Gly Pro Pro Pro Pro Pro Leu Ser Met Ala Gly Ser Thr Ala
        355                 360                 365

Pro Pro Pro Pro Pro Pro Pro Pro Gly Pro Pro Pro
    370                 375                 380

Pro Gly Leu Pro Ser Asp Gly Asp His Gln Val Pro Ala Ser Ser Gly
385                 390                 395                 400
```

```
Asn Lys Ala Ala Leu Leu Asp Gln Ile Arg Glu Gly Ala Gln Leu Lys
            405                 410                 415

Lys Val Glu Gln Asn Ser Arg Pro Val Ser Cys Ser Gly Arg Asp Ala
        420                 425                 430

Leu Leu Asp Gln Ile Arg Gln Gly Ile Gln Leu Lys Ser Val Ser Asp
            435                 440                 445

Gly Gln Glu Ser Thr Pro Pro Thr Pro Ala Pro Thr Ser Gly Ile Val
    450                 455                 460

Gly Ala Leu Met Glu Val Met Gln Lys Arg Ser Lys Ala Ile His Ser
465                 470                 475                 480

Ser Asp Glu Asp Glu Asp Asp Asp Glu Asp Phe Gln Asp Asp
                485                 490                 495

Asp Glu Trp Glu Asp
            500

<210> SEQ ID NO 9
<211> LENGTH: 369
<212> TYPE: DNA
<213> ORGANISM: Rattus norvegicus

<400> SEQUENCE: 9
ggtcccaatc tacccatggc tacagttgac ataaaaaatc cagaaatcac aacaaacagg      60
ttttatagtt cacaagtcaa caacatctcc cacaccaaag aaaagaagaa aggaaaagct     120
aaaaagaaga gattaaccaa ggcagatatt ggaacaccaa gtaatttcca gcacattgga     180
catgttggtt gggatccaaa tacaggtttt gatctaaata atttggatcc agaattgaag     240 aatcttttg atatgtgtgg gatctctgag gcccagctta agacagaga acatcaaaa       300 gttatttatg actttattga aaaaacagga ggtgtagaag ctgttaaaaa tgaactccga     360
aggcaagca                                                             369

<210> SEQ ID NO 10
<211> LENGTH: 123
<212> TYPE: PRT
<213> ORGANISM: Rattus norvegicus

<400> SEQUENCE: 10

Gly Pro Asn Leu Pro Met Ala Thr Val Asp Ile Lys Asn Pro Glu Ile
1               5                   10                  15

Thr Thr Asn Arg Phe Tyr Ser Ser Gln Val Asn Asn Ile Ser His Thr
            20                  25                  30

Lys Glu Lys Lys Lys Gly Lys Ala Lys Lys Arg Leu Thr Lys Ala
        35                  40                  45

Asp Ile Gly Thr Pro Ser Asn Phe Gln His Ile Gly His Val Gly Trp
    50                  55                  60

Asp Pro Asn Thr Gly Phe Asp Leu Asn Asn Leu Asp Pro Glu Leu Lys
65                  70                  75                  80

Asn Leu Phe Asp Met Cys Gly Ile Ser Glu Ala Gln Leu Lys Asp Arg
                85                  90                  95

Glu Thr Ser Lys Val Ile Tyr Asp Phe Ile Glu Lys Thr Gly Gly Val
            100                 105                 110

Glu Ala Val Lys Asn Glu Leu Arg Arg Gln Ala
        115                 120

<210> SEQ ID NO 11
<211> LENGTH: 1677
<212> TYPE: DNA
```

<213> ORGANISM: Escherichia coli

<400> SEQUENCE: 11

```
atgcctattg gtaaccttgg tcataatccc aatgtgaata attcaattcc tcctgcacct      60
ccattacctt cacaaaccga cggtgcaggg gggcgtggtc agctcattaa ctctacgggg     120
ccgttgggat ctcgtgcgct atttacgcct gtaaggaatt ctatggctga ttctggcgac     180
aatcgtgcca gtgatgttcc tggacttcct gtaaatccga tgcgcctggc ggcgtctgag     240
ataacactga atgatggatt tgaagttctt catgatcatg gtccgctcga tactcttaac     300
aggcagattg gctcttcggt atttcgagtt gaaactcagg aagatggtaa acatattgct     360
gtcggtcaga ggaatggtgt tgagacctct gttgttttaa gtgatcaaga gtacgctcgc     420
ttgcagtcca ttgatcctga aggtaaagac aaatttgtat ttactggagg ccgtggtggt     480
gctgggcatg ctatggtcac cgttgcttca gatatcacgg aagcccgcca aggatactg      540
gagctgttag agcccaaagg gaccggggag tccaaaggtg ctggggagtc aaaaggcgtt     600
ggggagttga gggagtcaaa tagcggtgcg gaaaacacca cagaaactca gacctcaacc     660
tcaacttcca gccttcgttc agatcctaaa ctttggttgg cgttggggac tgttgctaca     720
ggtctgatag ggttggcggc gacgggtatt gtacaggcgc ttgcattgac gccggagccg     780
gatagcccaa ccacgaccga ccctgatgca gctgcaagtg caactgaaac tgcgacaaga     840
gatcagttaa cgaaagaagc gttccagaac ccagataatc aaaaagttaa tatcgatgag     900
ctcggaaatg cgattccgtc agggtattg aaagatgatg ttgttgcgaa atagaagag      960
caggctaaag cagcaggcga agaggccaaa cagcaagcca ttgaaaataa tgctcaggcg    1020
caaaaaaat atgatgaaca caagctaaa cgccaggagg agctgaaagt ttcatcgggg      1080
gctggctacg gtcttagtgg cgcattgatt cttggtgggg aattggtgt tgccgtcacc      1140
gctgcgcttc atcgaaaaaa tcagccggta gaacaaacaa caacaactac tactacaact    1200
acaactacaa gcgcacgtac ggtagagaat aagcctgcaa ataatacacc tgcacagggc    1260
aatgtagata cccctgggtc agaagatacc atggagagca gacgtagctc gatggctagc    1320
acctcgtcga cttttctttga cacttccagc atagggaccg tgcagaatcc gtatgctgat    1380
gttaaaacat cgctgcatga ttcgcaggtg ccgacttcta attctaatac gtctgttcag    1440
aatatgggga atacagattc tgttgtatat agcaccattc aacatcctcc ccgggatact    1500
actgataacg gcgcacggtt attaggaaat ccaagtgcgg ggattcaaag cacttatgcg    1560
cgtctggcgc taagtggtgg attacgccat gacatgggag gattaacggg ggggagtaat    1620
agcgctgtga atacttcgaa taacccacca gcgccgggat ccatcgtttt cgtctaa      1677
```

<210> SEQ ID NO 12
<211> LENGTH: 558
<212> TYPE: PRT
<213> ORGANISM: Escherichia coli

<400> SEQUENCE: 12

```
Met Pro Ile Gly Asn Leu Gly His Asn Pro Asn Val Asn Asn Ser Ile
1               5                   10                  15

Pro Pro Ala Pro Pro Leu Pro Ser Gln Thr Asp Gly Ala Gly Gly Arg
            20                  25                  30

Gly Gln Leu Ile Asn Ser Thr Gly Pro Leu Gly Ser Arg Ala Leu Phe
        35                  40                  45

Thr Pro Val Arg Asn Ser Met Ala Asp Ser Gly Asp Asn Arg Ala Ser
    50                  55                  60
```

```
Asp Val Pro Gly Leu Pro Val Asn Pro Met Arg Leu Ala Ala Ser Glu
65                  70                  75                  80

Ile Thr Leu Asn Asp Gly Phe Glu Val Leu His Asp His Gly Pro Leu
                85                  90                  95

Asp Thr Leu Asn Arg Gln Ile Gly Ser Ser Val Phe Arg Val Glu Thr
            100                 105                 110

Gln Glu Asp Gly Lys His Ile Ala Val Gly Gln Arg Asn Gly Val Glu
        115                 120                 125

Thr Ser Val Val Leu Ser Asp Gln Glu Tyr Ala Arg Leu Gln Ser Ile
    130                 135                 140

Asp Pro Glu Gly Lys Asp Lys Phe Val Phe Thr Gly Arg Gly Gly
145                 150                 155                 160

Ala Gly His Ala Met Val Thr Val Ala Ser Asp Ile Thr Glu Ala Arg
                165                 170                 175

Gln Arg Ile Leu Glu Leu Leu Glu Pro Lys Gly Thr Gly Glu Ser Lys
            180                 185                 190

Gly Ala Gly Glu Ser Lys Gly Val Gly Glu Leu Arg Glu Ser Asn Ser
        195                 200                 205

Gly Ala Glu Asn Thr Thr Glu Thr Gln Thr Ser Thr Ser Thr Ser Ser
    210                 215                 220

Leu Arg Ser Asp Pro Lys Leu Trp Leu Ala Leu Gly Thr Val Ala Thr
225                 230                 235                 240

Gly Leu Ile Gly Leu Ala Ala Thr Gly Ile Val Gln Ala Leu Ala Leu
                245                 250                 255

Thr Pro Glu Pro Asp Ser Pro Thr Thr Thr Asp Pro Asp Ala Ala Ala
            260                 265                 270

Ser Ala Thr Glu Thr Ala Thr Arg Asp Gln Leu Thr Lys Glu Ala Phe
        275                 280                 285

Gln Asn Pro Asp Asn Gln Lys Val Asn Ile Asp Glu Leu Gly Asn Ala
    290                 295                 300

Ile Pro Ser Gly Val Leu Lys Asp Val Val Ala Asn Ile Glu Glu
305                 310                 315                 320

Gln Ala Lys Ala Ala Gly Glu Glu Ala Lys Gln Ala Ile Glu Asn
                325                 330                 335

Asn Ala Gln Ala Gln Lys Lys Tyr Asp Glu Gln Ala Lys Arg Gln
            340                 345                 350

Glu Glu Leu Lys Val Ser Ser Gly Ala Gly Tyr Gly Leu Ser Gly Ala
        355                 360                 365

Leu Ile Leu Gly Gly Gly Ile Gly Val Ala Val Thr Ala Ala Leu His
    370                 375                 380

Arg Lys Asn Gln Pro Val Glu Gln Thr Thr Thr Thr Thr Thr Thr
385                 390                 395                 400

Thr Thr Thr Ser Ala Arg Thr Val Glu Asn Lys Pro Ala Asn Asn Thr
                405                 410                 415

Pro Ala Gln Gly Asn Val Asp Thr Pro Gly Ser Glu Asp Thr Met Glu
            420                 425                 430

Ser Arg Arg Ser Ser Met Ala Ser Thr Ser Thr Phe Phe Asp Thr
        435                 440                 445

Ser Ser Ile Gly Thr Val Gln Asn Pro Tyr Ala Asp Val Lys Thr Ser
    450                 455                 460

Leu His Asp Ser Gln Val Pro Thr Ser Asn Ser Asn Thr Ser Val Gln
465                 470                 475                 480
```

```
Asn Met Gly Asn Thr Asp Ser Val Val Tyr Ser Thr Ile Gln His Pro
                485                 490                 495

Pro Arg Asp Thr Thr Asp Asn Gly Ala Arg Leu Leu Gly Asn Pro Ser
            500                 505                 510

Ala Gly Ile Gln Ser Thr Tyr Ala Arg Leu Ala Leu Ser Gly Gly Leu
        515                 520                 525

Arg His Asp Met Gly Gly Leu Thr Gly Gly Ser Asn Ser Ala Val Asn
    530                 535                 540

Thr Ser Asn Asn Pro Pro Ala Pro Gly Ser His Arg Phe Val
545                 550                 555

<210> SEQ ID NO 13
<211> LENGTH: 1644
<212> TYPE: DNA
<213> ORGANISM: Homo sapiens

<400> SEQUENCE: 13
atgagctggg gcacggagct gtgggatcag ttcgacagct agacaagca tacacaatgg      60
ggaattgact tcttggaaag atatgccaaa tttgttaaag agaggataga aattgaacag     120
aactatgcga acaattgag aaatctggtt aagaagtact gccccaaacg ttcatccaaa     180
gatgaagagc cacggtttac ctcgtgtgta gccttttta atatccttaa tgagttaaat     240
gactatgcag acagcgaga gttgtagca gaagaaatgg cgcacagagt gtatggtgaa     300
ttaatgagat atgctcatga tctgaaaact gaaagaaaaa tgcatctgca gaaggacga     360
aaagctcaac aatatcttga catgtgctgg aaacagatgg ataatagtaa aagaagttt     420
gaaagagaat gtagagaggc agaaaaggca caacagagtt atgaaagatt ggataatgat     480
actaatgcaa ccaaggcaga tgttgaaaag gccaaacagc agttgaatct gcgtacgcat     540
atggccgatg aaaataaaaa tgaatatgct gcacaattac aaaactttaa tggagaacaa     600
cataaacatt tttatgtagt gattcctcag atttacaagc aactacaaga aatggacgaa     660
cgaaggacta ttaaactcag tgagtgttac agaggatttg ctgactcaga acgcaaagtt     720
attcccatca tttcaaaatg tttggaagga atgattcttg cagcaaaatc agttgatgaa     780
agaagagact ctcaaatggt ggtagactcc ttcaaatctg gttttgaacc tccaggagac     840
tttccatttg aagattacag tcaacatata tatagaacca tttctgatgg gactatcagt     900
gcatccaaac aggagagtgg aagatggat gccaaaacca cagtaggaaa ggccaagggc     960
aaattgtggc tctttggaaa gaagccaaag ggcccagcac tagaagattt cagtcatctg    1020
ccaccagaac agagacgtaa aaaactacag cagcgcattg atgaacttaa cagagaacta    1080
cagaaagaat cagaccaaaa agatgcactc aacaaaatga agatgtata tgagaagaat    1140
ccacaaatgg gggatccagg gagtttgcag cctaaattag cagagaccat gaataacatt    1200
gaccgcctac gaatggaaat ccataagaat gaggcttggc tctctgaagt cgaaggcaaa    1260
acaggtggga gaggagacag aagacatagc agtgacataa atcatcttgt aacacaggga    1320
cgagaaagtc ctgagggaag ttacactgat gatgcaaacc aggaagtccg tgggccaccc    1380
cagcagcatg gtcaccacaa tgagtttgat gatgaatttg aggatgatga tcccttgcct    1440
gctattggac actgcaaagc tatctaccct tttgatggac ataatgaagg tactctagca    1500
atgaaagaag gtgaagttct ctacattata gaggaggaca aaggtgacgg atggacaaga    1560
gctcggagac agaacggtga agaaggctac gttcccacgt catacataga tgtaactcta    1620
gagaaaaaca gtaaaggttc ctga                                           1644
```

<210> SEQ ID NO 14
<211> LENGTH: 547
<212> TYPE: PRT
<213> ORGANISM: Homo sapiens

<400> SEQUENCE: 14

Met Ser Trp Gly Thr Glu Leu Trp Asp Gln Phe Asp Ser Leu Asp Lys
1               5                   10                  15

His Thr Gln Trp Gly Ile Asp Phe Leu Glu Arg Tyr Ala Lys Phe Val
            20                  25                  30

Lys Glu Arg Ile Glu Ile Glu Gln Asn Tyr Ala Lys Gln Leu Arg Asn
        35                  40                  45

Leu Val Lys Lys Tyr Cys Pro Lys Arg Ser Ser Lys Asp Glu Glu Pro
    50                  55                  60

Arg Phe Thr Ser Cys Val Ala Phe Phe Asn Ile Leu Asn Glu Leu Asn
65                  70                  75                  80

Asp Tyr Ala Gly Gln Arg Glu Val Val Ala Glu Met Ala His Arg
            85                  90                  95

Val Tyr Gly Glu Leu Met Arg Tyr Ala His Asp Leu Lys Thr Glu Arg
            100                 105                 110

Lys Met His Leu Gln Glu Gly Arg Lys Ala Gln Gln Tyr Leu Asp Met
        115                 120                 125

Cys Trp Lys Gln Met Asp Asn Ser Lys Lys Lys Phe Glu Arg Glu Cys
    130                 135                 140

Arg Glu Ala Glu Lys Ala Gln Gln Ser Tyr Glu Arg Leu Asp Asn Asp
145                 150                 155                 160

Thr Asn Ala Thr Lys Ala Asp Val Glu Lys Ala Lys Gln Gln Leu Asn
            165                 170                 175

Leu Arg Thr His Met Ala Asp Glu Asn Lys Asn Glu Tyr Ala Ala Gln
            180                 185                 190

Leu Gln Asn Phe Asn Gly Glu Gln His Lys His Phe Tyr Val Val Ile
        195                 200                 205

Pro Gln Ile Tyr Lys Gln Leu Gln Glu Met Asp Glu Arg Arg Thr Ile
    210                 215                 220

Lys Leu Ser Glu Cys Tyr Arg Gly Phe Ala Asp Ser Glu Arg Lys Val
225                 230                 235                 240

Ile Pro Ile Ile Ser Lys Cys Leu Glu Gly Met Ile Leu Ala Ala Lys
            245                 250                 255

Ser Val Asp Glu Arg Arg Asp Ser Gln Met Val Val Asp Ser Phe Lys
            260                 265                 270

Ser Gly Phe Glu Pro Pro Gly Asp Phe Pro Phe Glu Asp Tyr Ser Gln
        275                 280                 285

His Ile Tyr Arg Thr Ile Ser Asp Gly Thr Ile Ser Ala Ser Lys Gln
    290                 295                 300

Glu Ser Gly Lys Met Asp Ala Lys Thr Thr Val Gly Lys Ala Lys Gly
305                 310                 315                 320

Lys Leu Trp Leu Phe Gly Lys Lys Pro Lys Gly Pro Ala Leu Glu Asp
            325                 330                 335

Phe Ser His Leu Pro Pro Glu Gln Arg Arg Lys Lys Leu Gln Gln Arg
            340                 345                 350

Ile Asp Glu Leu Asn Arg Glu Leu Gln Lys Glu Ser Asp Gln Lys Asp
        355                 360                 365

Ala Leu Asn Lys Met Lys Asp Val Tyr Glu Lys Asn Pro Gln Met Gly
    370                 375                 380

-continued

```
Asp Pro Gly Ser Leu Gln Pro Lys Leu Ala Glu Thr Met Asn Asn Ile
385                 390                 395                 400

Asp Arg Leu Arg Met Glu Ile His Lys Asn Glu Ala Trp Leu Ser Glu
            405                 410                 415

Val Glu Gly Lys Thr Gly Gly Arg Gly Asp Arg Arg His Ser Ser Asp
        420                 425                 430

Ile Asn His Leu Val Thr Gln Gly Arg Glu Ser Pro Glu Gly Ser Tyr
    435                 440                 445

Thr Asp Asp Ala Asn Gln Glu Val Arg Gly Pro Pro Gln Gln His Gly
450                 455                 460

His His Asn Glu Phe Asp Asp Glu Phe Glu Asp Asp Pro Leu Pro
465                 470                 475                 480

Ala Ile Gly His Cys Lys Ala Ile Tyr Pro Phe Asp Gly His Asn Glu
            485                 490                 495

Gly Thr Leu Ala Met Lys Glu Gly Glu Val Leu Tyr Ile Ile Glu Glu
        500                 505                 510

Asp Lys Gly Asp Gly Trp Thr Arg Ala Arg Arg Gln Asn Gly Glu Glu
    515                 520                 525

Gly Tyr Val Pro Thr Ser Tyr Ile Asp Val Thr Leu Glu Lys Asn Ser
530                 535                 540

Lys Gly Ser
545

<210> SEQ ID NO 15
<211> LENGTH: 1638
<212> TYPE: DNA
<213> ORGANISM: Homo sapiens

<400> SEQUENCE: 15
atgtcaaata acggcctaga cattcaagac aaaccccag ccctcccgat gagaaatacc      60
agcactatga ttggagccgg cagcaaagat gctggaaccc taaccatgg ttctaaacct    120 ctgcctccaa acccagagga gaagaaaaag aaggaccgat tttaccgatc cattttacct    180
ggagataaaa caaataaaaa gaaagagaaa gagcggccag agatttctct cccttcagat    240
tttgaacaca caattcatgt cggttttgat gctgtcacag gggagtttac gggaatgcca    300
gagcagtggg cccgcttgct tcagacatca aatatcacta gtcggagca agagaaaaac    360 ccgcaggctg ttctggatgt gttggagttt acaactcga agaagacatc caacagccag    420
aaatacatga gctttacaga taagtcagct gaggattaca attcttctaa tgccttgaat    480
gtgaaggctg tgtctgagac tcctgcagtg ccaccagttt cagaagatga ggatgatgat    540
gatgatgatg ctaccccacc accagtgatt gctccacgcc cagagcacac aaaatctgta    600
tacacacggt ctgtgattga accacttcct gtcactccaa ctcgggacgt ggctacatct    660
cccatttcac ctactgaaaa taacaccact ccaccagatg ctttgacccg gaatactgag    720
aagcagaaga gaagcctaa aatgtctgat gaggagatct tggagaaatt acgaagcata    780
gtgagtgtgg gcgatcctaa gaagaaatat acacggtttg agaagattgg acaaggtgct    840
tcaggcaccg tgtacacagc aatggatgtg ccacaggac aggaggtggc cattaagcag    900
atgaatcttc agcagcagcc aagaaagag ctgattatta tgagatcct ggtcatgagg    960 gaaaacaaga acccaaacat tgtgaattac ttggacagtt acctcgtggg agatgagctg   1020
tgggttgtta tggaatactt ggctggaggc tccttgacag atgtggtgac agaaacttgc   1080
atggatgaag gccaaattgc agctgtgtgc cgtgagtgtc tgcaggctct ggagttcttg   1140
```

```
cattcgaacc aggtcattca cagagacatc aagagtgaca atattctgtt gggaatggat    1200
ggctctgtca agctaactga ctttggattc tgtgcacaga taaccccaga gcagagcaaa    1260
cggagcacca tggtaggaac cccatactgg atggcaccag aggttgtgac acgaaaggcc    1320
tatgggccca aggttgacat ctggtccctg gcatcatgg ccatcgaaat gattgaaggg    1380
gagcctccat acctcaatga aaaccctctg agagccttgt acctcattgc caccaatggg    1440
accccagaac ttcagaaccc agagaagctg tcagctatct tccgggactt tctgaaccgc    1500
tgtctcgaga tggatgtgga agagagaggt tcagctaaag agctgctaca gcatcaattc    1560
ctgaagattg ccaagcccct ctccagcctc actccactga ttgctgcagc taaggaggca    1620
acaaagaaca atcactaa                                                  1638
```

<210> SEQ ID NO 16
<211> LENGTH: 545
<212> TYPE: PRT
<213> ORGANISM: Homo sapiens

<400> SEQUENCE: 16

```
Met Ser Asn Asn Gly Leu Asp Ile Gln Asp Lys Pro Pro Ala Pro Pro
1               5                   10                  15

Met Arg Asn Thr Ser Thr Met Ile Gly Ala Gly Ser Lys Asp Ala Gly
            20                  25                  30

Thr Leu Asn His Gly Ser Lys Pro Leu Pro Asn Pro Glu Glu Lys
        35                  40                  45

Lys Lys Lys Asp Arg Phe Tyr Arg Ser Ile Leu Pro Gly Asp Lys Thr
    50                  55                  60

Asn Lys Lys Lys Glu Lys Glu Arg Pro Glu Ile Ser Leu Pro Ser Asp
65                  70                  75                  80

Phe Glu His Thr Ile His Val Gly Phe Asp Ala Val Thr Gly Glu Phe
                85                  90                  95

Thr Gly Met Pro Glu Gln Trp Ala Arg Leu Leu Gln Thr Ser Asn Ile
            100                 105                 110

Thr Lys Ser Glu Gln Lys Lys Asn Pro Gln Ala Val Leu Asp Val Leu
        115                 120                 125

Glu Phe Tyr Asn Ser Lys Lys Thr Ser Asn Ser Gln Lys Tyr Met Ser
    130                 135                 140

Phe Thr Asp Lys Ser Ala Glu Asp Tyr Asn Ser Ser Asn Ala Leu Asn
145                 150                 155                 160

Val Lys Ala Val Ser Glu Thr Pro Ala Val Pro Val Ser Glu Asp
                165                 170                 175

Glu Asp Asp Asp Asp Asp Ala Thr Pro Pro Val Ile Ala Pro
            180                 185                 190

Arg Pro Glu His Thr Lys Ser Val Tyr Thr Arg Ser Val Ile Glu Pro
        195                 200                 205

Leu Pro Val Thr Pro Thr Arg Asp Val Ala Thr Ser Pro Ile Ser Pro
    210                 215                 220

Thr Glu Asn Asn Thr Thr Pro Pro Asp Ala Leu Thr Arg Asn Thr Glu
225                 230                 235                 240

Lys Gln Lys Lys Lys Pro Lys Met Ser Asp Glu Glu Ile Leu Glu Lys
                245                 250                 255

Leu Arg Ser Ile Val Ser Val Gly Asp Pro Lys Lys Tyr Thr Arg
            260                 265                 270
```

-continued

```
Phe Glu Lys Ile Gly Gln Gly Ala Ser Gly Thr Val Tyr Thr Ala Met
            275                 280                 285
Asp Val Ala Thr Gly Gln Glu Val Ala Ile Lys Gln Met Asn Leu Gln
        290                 295                 300
Gln Gln Pro Lys Lys Glu Leu Ile Ile Asn Glu Ile Leu Val Met Arg
305                 310                 315                 320
Glu Asn Lys Asn Pro Asn Ile Val Asn Tyr Leu Asp Ser Tyr Leu Val
                325                 330                 335
Gly Asp Glu Leu Trp Val Val Met Glu Tyr Leu Ala Gly Gly Ser Leu
            340                 345                 350
Thr Asp Val Val Thr Glu Thr Cys Met Asp Glu Gly Gln Ile Ala Ala
        355                 360                 365
Val Cys Arg Glu Cys Leu Gln Ala Leu Glu Phe Leu His Ser Asn Gln
370                 375                 380
Val Ile His Arg Asp Ile Lys Ser Asp Asn Ile Leu Leu Gly Met Asp
385                 390                 395                 400
Gly Ser Val Lys Leu Thr Asp Phe Gly Phe Cys Ala Gln Ile Thr Pro
                405                 410                 415
Glu Gln Ser Lys Arg Ser Thr Met Val Gly Thr Pro Tyr Trp Met Ala
            420                 425                 430
Pro Glu Val Val Thr Arg Lys Ala Tyr Gly Pro Lys Val Asp Ile Trp
        435                 440                 445
Ser Leu Gly Ile Met Ala Ile Glu Met Ile Glu Gly Glu Pro Pro Tyr
450                 455                 460
Leu Asn Glu Asn Pro Leu Arg Ala Leu Tyr Leu Ile Ala Thr Asn Gly
465                 470                 475                 480
Thr Pro Glu Leu Gln Asn Pro Glu Lys Leu Ser Ala Ile Phe Arg Asp
                485                 490                 495
Phe Leu Asn Arg Cys Leu Glu Met Asp Val Glu Lys Arg Gly Ser Ala
            500                 505                 510
Lys Glu Leu Leu Gln His Gln Phe Leu Lys Ile Ala Lys Pro Leu Ser
        515                 520                 525
Ser Leu Thr Pro Leu Ile Ala Ala Ala Lys Glu Ala Thr Lys Asn Asn
530                 535                 540
His
545
```

<210> SEQ ID NO 17
<211> LENGTH: 43
<212> TYPE: DNA
<213> ORGANISM: Artificial Sequence
<220> FEATURE:
<223> OTHER INFORMATION: Primer

<400> SEQUENCE: 17
ataagaatgc ggccgcaagt atatcccgat acatcatgct ctc          43

<210> SEQ ID NO 18
<211> LENGTH: 37
<212> TYPE: DNA
<213> ORGANISM: Artificial Sequence
<220> FEATURE:
<223> OTHER INFORMATION: Primer

<400> SEQUENCE: 18
ataagaatgc ggccgcgctt cacaaaaccg gagtccg                 37

```
<210> SEQ ID NO 19
<211> LENGTH: 30
<212> TYPE: DNA
<213> ORGANISM: Artificial Sequence
<220> FEATURE:
<223> OTHER INFORMATION: Primer

<400> SEQUENCE: 19
ctctcttcta gataaaggag caaaagtata                                    30

<210> SEQ ID NO 20
<211> LENGTH: 51
<212> TYPE: DNA
<213> ORGANISM: Artificial Sequence
<220> FEATURE:
<223> OTHER INFORMATION: Primer

<400> SEQUENCE: 20
ataagaatgc ggccgccata tggattacct tataagtaat tttagttctc c            51

<210> SEQ ID NO 21
<211> LENGTH: 44
<212> TYPE: DNA
<213> ORGANISM: Artificial Sequence
<220> FEATURE:
<223> OTHER INFORMATION: Primer

<400> SEQUENCE: 21
atcatcctgc agtgattata atataattac ctatattagc tctg                    44

<210> SEQ ID NO 22
<211> LENGTH: 33
<212> TYPE: DNA
<213> ORGANISM: ATCATCGAGCTCCTTGCCCCCAAAGATACCACA
<220> FEATURE:
<223> OTHER INFORMATION: Primer

<400> SEQUENCE: 22
atcatcgagc tccttgcccc caaagatacc aca                                33

<210> SEQ ID NO 23
<211> LENGTH: 40
<212> TYPE: DNA
<213> ORGANISM: Artificial Sequence
<220> FEATURE:
<223> OTHER INFORMATION: Primer

<400> SEQUENCE: 23
ataagaatgc ggccgcggat cccatcgatt taaagctatg                         40

<210> SEQ ID NO 24
<211> LENGTH: 40
<212> TYPE: DNA
<213> ORGANISM: Artificial Sequence
<220> FEATURE:
<223> OTHER INFORMATION: Primer

<400> SEQUENCE: 24
ctagtctaga ctgcagttag gtgaggtcgc ccaagctctc                         40

<210> SEQ ID NO 25
<211> LENGTH: 41
<212> TYPE: DNA
<213> ORGANISM: Artificial Sequence
<220> FEATURE:
<223> OTHER INFORMATION: Primer
```

-continued

```
<400> SEQUENCE: 25
ccggaattcc atatgattaa caatgtttct tcactttttc c                    41

<210> SEQ ID NO 26
<211> LENGTH: 33
<212> TYPE: DNA
<213> ORGANISM: Artificial Sequence
<220> FEATURE:
<223> OTHER INFORMATION: Primer

<400> SEQUENCE: 26
cgcggatccc gagcgcttag atgtattaat gcc                             33
```